(12) United States Patent
Tateishi et al.

(10) Patent No.: US 8,703,935 B2
(45) Date of Patent: *Apr. 22, 2014

(54) METHOD OF PRODUCING A METAL PHTHALOCYANINE COMPOUND, AND METHOD OF PRODUCING A PHTHALOCYANINE COMPOUND AND AN ANALOGUE THEREOF

(75) Inventors: Keiichi Tateishi, Minami-ashigara (JP); Masahiko Taniguchi, Minami-ashigara (JP); Hideo Hanawa, Minami-ashigara (JP); Nobuo Seto, Minami-ashigara (JP); Kazufumi Omura, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/620,046

(22) Filed: Sep. 14, 2012

(65) Prior Publication Data

US 2013/0012697 A1    Jan. 10, 2013

Related U.S. Application Data

(62) Division of application No. 12/088,412, filed as application No. PCT/JP2006/310280 on May 17, 2006, now Pat. No. 8,299,240.

(30) Foreign Application Priority Data

Sep. 28, 2005  (JP) .................. 2005-283002
Sep. 28, 2005  (JP) .................. 2005-283032

(51) Int. Cl.
*C07D 487/22* (2006.01)
*C07B 47/00* (2006.01)

(52) U.S. Cl.
USPC .......................................... 540/145

(58) Field of Classification Search
USPC .......................................... 540/145
See application file for complete search history.

(56) References Cited

U.S. PATENT DOCUMENTS 2,910,482 A    10/1959  Gottlieb
8,299,240 B2 *  10/2012  Tateishi et al. ............. 540/145

FOREIGN PATENT DOCUMENTS

EP    1 428 859 A1   6/2004
GB    2343187 A      5/2000

(Continued)

OTHER PUBLICATIONS

Hirofusa Shirai, et al.; "Phthalocyanie-Kaguku to Kino-"; Industrial Publishing & Consulting, Inc. (1997).

(Continued)

*Primary Examiner* — Paul V. Ward
(74) *Attorney, Agent, or Firm* — Sughrue Mion, PLLC

(57) ABSTRACT

A method of producing a metal phthalocyanine compound, which contains: conducting a reaction between at least two compounds selected from among Compounds A to F of formula (I), and a metal compound, in a buffer solution of an organic base or an inorganic base and an acid, in the presence of a dehydrating agent:

Formula (I)

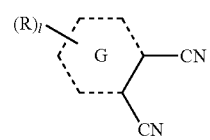

Compound A

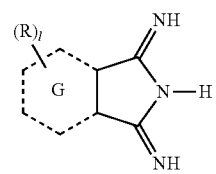

Compound B

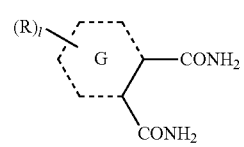

Compound C

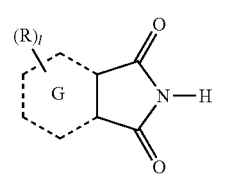

Compound D

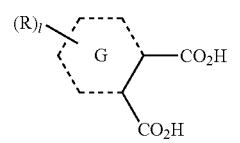

Compound E

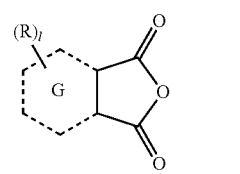

Compound F wherein R is a hydrogen atom or a substituent; l is an integer of 0 to 4; a plurality of Rs may be the same or different from each other when l is 2 to 4; and G is a group of atoms necessary for forming at least one of a 5- or 6-membered aromatic ring and a 5- or 6-membered hetero ring.

12 Claims, 2 Drawing Sheets

(56) References Cited

FOREIGN PATENT DOCUMENTS

| | | |
|---|---|---|
| JP | 2520476 | 5/1996 |
| JP | 11-116835 | 4/1999 |
| JP | 11-116836 A | 4/1999 |
| JP | 11-209380 | 8/1999 |
| JP | 11-263919 | 9/1999 |
| JP | 11-269399 | 10/1999 |
| JP | 2000-169743 | 6/2000 |
| JP | 2001-64283 A | 3/2001 |
| JP | 2003-12952 | 1/2003 |
| JP | 2004-331734 | 11/2004 |
| JP | 2005-41856 | 2/2005 |
| WO | 99/23096 A1 | 5/1999 |

OTHER PUBLICATIONS

S.A. Mikhalenko, et al.; "Phthalocyanines and Related Compounds. XIX. Tetra- and Octaamino-Substituted Phthalocyanines"; Journal of General Chemistry USSR; Consultants Bureau; New York; NY; US; vol. 51; No. 7; Jan. 1, 1981; pp. 1405-1411; XP-002078329.

John P. Linsky, et al.; "Studies of a Series of Haloaluminum, -gallium, and -indium Phthalocyanines"; Inorg. Chem.; vol. 19; 1980; pp. 3131-3135; XP-002598121.

Chinese Office Action dated Nov. 1, 2011 for corresponding Chinese Patent Application No. 200680041694.7.

Korean Intellectual Property Office, "Notice of Submission of Opinion," issued in connection with Korean Patent Application No. 10-2008-7009563, dated Mar. 20, 2013.

* cited by examiner

METHOD OF PRODUCING A METAL PHTHALOCYANINE COMPOUND, AND METHOD OF PRODUCING A PHTHALOCYANINE COMPOUND AND AN ANALOGUE THEREOF

CROSS-REFERENCE TO RELATED APPLICATIONS

This is a Divisional of application Ser. No. 12/088,412 filed Mar. 27, 2008, which is a 371 of PCT Application No. PCT/JP2006/310280 filed May 17, 2006, which claims benefit to Japanese Patent Application No. 2005-283002 filed Sep. 28, 2005 and Japanese Patent Application No. 2005-283032 filed Sep. 28, 2005. The above-noted applications are incorporated herein by reference in their entirety.

TECHNICAL FIELD

The present invention relates to a novel method of producing a metal phthalocyanine compound. The present invention more specifically relates to a method of producing a metal phthalocyanine compound in high yield constantly under mild conditions.

Further, the present invention relates to a method of producing a phthalocyanine compound having a variety of substituents and an analogue thereof.

BACKGROUND ART

A metal phthalocyanine compound is a useful compound as a material for paint, printing ink, colorant, electrophotosensitive material or body, or optical disc, and hitherto a great many compound have been synthesized and produced. Industrial production of the metal phthalocyanine compound is described in detail in "Phthalocyanine-Kagaku to Kino-", written by Hirofusa Shirai and Nagao Kobayashi, published by Industrial Publishing & Consulting, Inc. (1997). The industrial production of the metal phthalocyanine compound is roughly classified into two methods.

1) Weyler Method:

This method employs phthalic anhydride or phthalic anhydride imide as a raw material and involves a reaction of urea and a metal salt at 160° C. to 180° C. in the presence of a condensation agent for production of a metal phthalocyanine compound. An arsenic-series inorganic salt has been heretofore used as a condensation agent, but in recent years, a molybdate is generally used. This method includes, as a solid phase method, a method in which a urea melt is used as a solvent. However, the solid phase method is not preferred as a method for mass production, because of risk of foaming, disadvantages due to solidification during temperature decrease, low yield, and formation of large amounts of impurities in a product.

Meanwhile, a liquid phase method employing an inert organic solvent, such as nitrobenzene or polyhalogenated benzene, provides higher yield and tends to provide more stable quality than those of the solid phase method. The liquid phase method is the main stream of a current method for industrial production of phthalocyanine. However, this liquid phase method requires complex unit operations such as separation and recovery of a reaction solvent. Further, the liquid phase method has problems in safety in that nitrobenzene is toxic and polyhalogenated benzene forms small amounts of toxic substances such as halogenated biphenyl as by-products. Thus, selection of an appropriate high-boiling-point solvent is one of tasks to be solved by the method for industrial production of phthalocyanine.

2) Phthalonitrile Method:

This method employs highly reactive phthalonitrile as a starting material. This method includes: a method referred to as a solid phase method or a baking method, which involves heating of a mixture of phthalonitrile and a metal salt and using molten urea as a solvent; and a liquid phase method, which involves heat condensation of phthalonitrile and a metal salt in an appropriate high boiling point solvent. In this case, quinoline or the like has been preferably used as a basic solvent for its condensation acceleration function, but industrial use of quinoline or the like must be avoided at present from a viewpoint of safety. Selection of a solvent is also one task in this method, similar to that in the liquid phase method of the Weyler method. A price of phthalonitrile is about ten times that of phthalic anhydride, and this method has a disadvantage in that a raw material cost of this method is much higher than that of the Weyler method. However, this method is an optimal method for recent production of functional phthalocyanine having high added value when emphasis is placed on various merits in production, even in consideration of terminal price of a product.

Further, JP-A-49-49759 ("JP-A" means unexamined published Japanese patent application) discloses a method of relaxing reaction conditions in this phthalonitrile method by using a base. For example, JP-A-49-49759 describes that copper phthalocyanine can be obtained in high yield through a reaction of phthalonitrile and cuprous chloride in ethylene glycol under ammonia bubbling at a temperature of about 100° C. Further, various phthalocyanines are industrially produced by using as a condensation agent of a high-boiling-point amine, such as a secondary or tertiary amine, instead of ammonia as a base. The specification of Japanese Patent No. 2,520,476 discloses a general method for industrial production of nonmetal phthalocyanine, and this method employs, as a condensation agent, a high-boiling-point amine, such as tributylamine, diazabicycloundecene, and diazobicyclononene, as an amine, in addition to an alcholate.

However, use of such a relatively strong base may cause decomposition of some kinds of phthalonitrile, and provides a disadvantage of degrading yield of a target phthalocyanine compound. For example, phthalonitrile having an electron withdrawing group substituted causes a concerted reaction of an intended condensation reaction and a decomposition reaction due to attack on phthalonitrile by a nucleophilic reagent such as a hydroxide ion, and thus a condensation rate of a metal phthalocyanine compound is not improved. Further, in production of a metal phthalocyanine compound by using a metal chloride, hydrochloric acid is produced with progress of condensation, and hydrochloric acid inhibits the attack by a nucleophilic species serving as a catalyst for condensation. Thus, the progress of the condensation reaction gradually slows down, and the reaction eventually stops even if the raw material remains. In this case, a target substance alone is hardly isolated from a reaction mixture through a recrystallization or reprecipitation method, which may appropriately be used for production, and a purification method involving column chromatography which has low production efficiency is required. Thus, this method has a disadvantage of an extended production process, leading to cost increase from an industrial viewpoint.

There are known: a method involving a reaction by using a high-boiling-point alcohol (such as n-butanol) solvent in the presence of a strong base such as DBU, as disclosed in JP-A-11-269399; and a method involving use of a metal alkoxide, as disclosed in JP-A-11-209380. However, a reaction system in each of the methods is strongly basic, and a substrate having a substituent that is easily decomposed under basic conditions cannot be used. Further, a reaction substrate may decompose owing to water contained in the reaction substrate or solvent, and a yield may be reduced significantly.

Further, there are also known: a method involving a reaction in the presence of a dehydrating agent, as disclosed in JP-A-11-116835; and a method involving a reaction in the presence of a metal oxide and an acid having a pKa of 7.0 or less in combination, as disclosed in JP-A-11-263919. Those methods provide improved yield, but the yield is currently not at a satisfying level. JP-A-2000-169743 discloses a method of producing a phthalocyanine compound in the presence of an alkali earth metal compound, but this method has problems in yield and purity.

There is known an economic production method, as disclosed in JP-A-2005-41856, with significantly improved reactivity and purity for solving the above-mentioned problems, but there is a need for further improvement in yield and a method of improving operability (reduction in reaction time, crystallinity, filtration property, or the like) on a production scale.

Further, a phthalocyanine compound and an analogue thereof each find use in a wide variety of applications including a dye or pigment having high fastness and a functional colorant. In recent years, introduction of various substituents into the phthalocyanine compound has been demanded strongly for providing enhanced functions, but such a demand cannot necessarily be met through currently known synthesis methods.

For example, there are known: a method involving a reaction by using a high-boiling-point alcohol (such as n-butanol) solvent in the presence of a strong base such as DBU, as disclosed in JP-A-11-269399; and a method involving use of a metal alkoxide, as disclosed in JP-A-11-209380. However, a reaction system in each of the methods is strongly basic, and a substrate having a substituent that is easily decomposed under basic conditions cannot be used. Further, a reaction substrate may decompose owing to water contained in the reaction substrate or solvent, and a yield may be reduced significantly. Further, there are also known: a method involving a reaction in the presence of a dehydrating agent, as disclosed in JP-A-11-116835; and a method involving a reaction in the presence of a metal oxide and an acid having a pKa of 7.0 or less in combination, as disclosed in JP-A-11-263919. Those methods provide improved yield, but the yield is currently not at a satisfying level.

DISCLOSURE OF INVENTION

The present invention has been made in view of solving conventional problems in the method of producing a metal phthalocyanine compound as described above. The present invention is contemplated for providing a method of producing a metal phthalocyanine compound with high yield, high purity, favorable operability, and industrial stability, through a reaction under heating of at least two specific compounds selected from Compounds A to F represented by Formula (I) shown below, and a metal compound, in the presence of a dehydrating agent.

Further, the present invention is contemplated for providing a method of producing a phthalocyanine compound efficiently in high yield, by using any of phthalonitrile compounds having various substituents, as a starting material.

According to the present invention, there is provided the following means:

(1) A method of producing a metal phthalocyanine compound, comprising:

conducting a reaction between at least two compounds selected from the group consisting of Compounds A to F represented by formula (I), and a metal compound, in a buffer solution of an organic base or an inorganic base and an acid, in the presence of a dehydrating agent:

Formula (I)

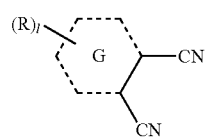

Compound A

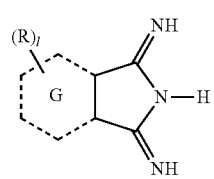

Compound B

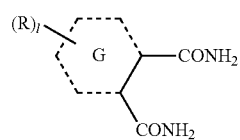

Compound C

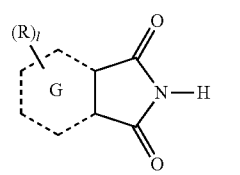

Compound D

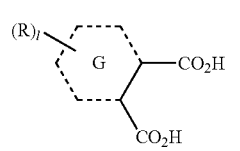

Compound E

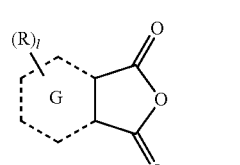

Compound F wherein R represents a hydrogen atom or a substituent; l represents an integer of 0 to 4; a plurality of Rs may be the same or different from each other when l is 2 to 4; and G represents a group of atoms necessary for forming at least one of a 5- or 6-membered aromatic ring and a 5- or 6-membered hetero ring.

(2) The method of producing a metal phthalocyanine compound according to the above item (1), wherein the compounds (Compounds A to F) represented by formula (I) are compounds (Compounds G to L) represented by formula (II):

Formula (II)

Compound G
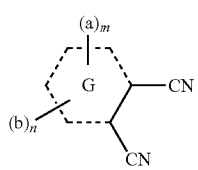

Compound H
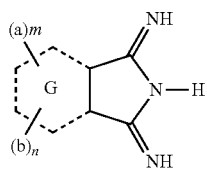

Compound I
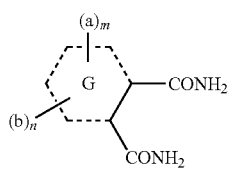

Compound J
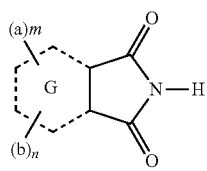

Compound K
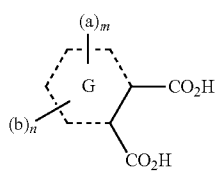

Compound L
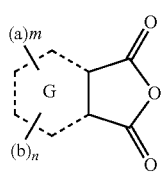

Formula (III)

Compound M
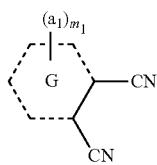

Compound N
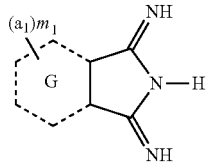

Compound O
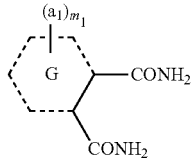

Compound P
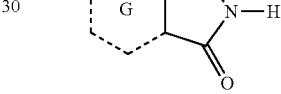

Compound Q

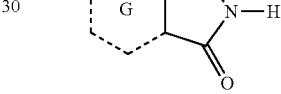

Compound R wherein a and b each independently represent a substituent; a total Hammett's constant σp value of the substituents is 0.20 or more; m and n each represent an integer satisfying $0 \leq m \leq 4$, $0 \leq n \leq 3$, and $0 \leq (m+n) \leq 4$; and G represents a group of atoms necessary for forming at least one of a 5- or 6-membered aromatic ring and a 5- or 6-membered hetero ring.

(3) The method of producing a metal phthalocyanine compound according to the above item (1) or (2), wherein the compounds (Compounds A to F) represented by formula (I) or the compounds (Compounds G to L) represented by formula (II) are compounds (Compounds M to R) represented by formula (III):

wherein $a_1$s each independently represent a sulfinyl group, a sulfonyl group, a sulfamoyl group, an acyl group, or a carbamoyl group, each of which may have a substituent; $m_1$ represents an integer of 0 to 2; and G represents a group of atoms necessary for forming at least one of a 5- or 6-membered aromatic ring and a 5- or 6-membered hetero ring.

(4) The method of producing a metal phthalocyanine compound according to any one of the above items (1) to (3), wherein the compounds (Compounds A to F) represented by formula (I), the compounds (Compounds G to L) represented by formula (II), or the compounds (Compounds M to R) represented by formula (III) are compounds (Compounds S to X) represented by formula (IV):

Formula (IV)

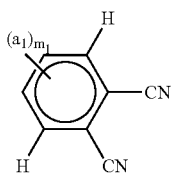
Compound S

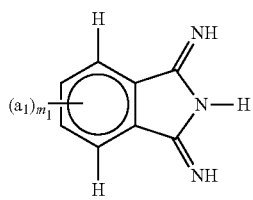
Compound T

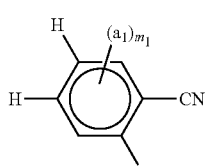
Compound U

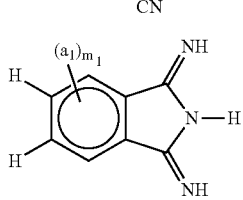
Compound V

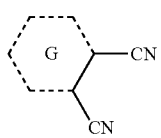
Compound W

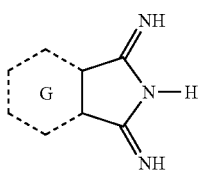
Compound X wherein $a_1$s each independently represent a sulfinyl group, a sulfonyl group, a sulfamoyl group, an acyl group, or a carbamoyl group, each of which may have a substituent; $m_1$ represents an integer of 0 to 2; and G represents a group of atoms necessary for forming a 6-membered nitrogen-containing hetero ring.

(5) The method of producing a metal phthalocyanine compound according to any one of the above items (1) to (4), wherein at least one selected from the group consisting of compounds represented by formula (V) and glycerin is used as a reaction solvent:

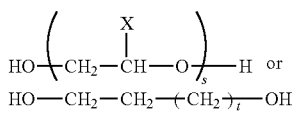
Formula (V)

wherein s and t each independently represent a positive integer; and X represents a hydrogen atom or a methyl group.

(6) The method of producing a metal phthalocyanine compound according to any one of the above items (1) to (5), wherein the dehydrating agent is selected from the group consisting of an acetal compound, an orthoester compound, an alkenyl ether compound, an alkenyl ester compound, an epoxide compound, and an oxetane compound.

(7) The method of producing a metal phthalocyanine compound according to any one of the above items (1) to (6), wherein at least one salt selected from the group consisting of an alkali metal salt, ammonium salt, or tertiary amine salt of a carboxylic acid is used as the base.

(8) The method of producing a metal phthalocyanine compound according to any one of the above items (1) to (6), wherein at least one compound selected from among compounds represented by formula (VI) is used as the base:

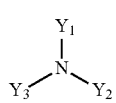
Formula (VI)

wherein $Y_1$, $Y_2$, and $Y_3$ each independently represent a hydrogen atom, an alkyl group, an alkenyl group, an alkynyl group, a cycloalkyl group, a cycloalkenyl group, an aryl group, or a hetero ring; $Y_1$, $Y_2$, and $Y_3$ may bond to form a condensed cyclic organic base; and $Y_1$, $Y_2$, and $Y_3$ may each further have a substituent.

(9) A method of producing a phthalocyanine compound represented by formula (13) or (14), or a phthalocyanine analogue, comprising:

conducting a reaction of a compound represented by formula (11) or (12), in the presence of a dehydrating agent and an ammonium salt compound in combination, thereby producing the phthalocyanine compound represented by formula (13) or (14), or the phthalocyanine analogue:

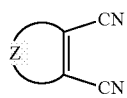
Formula (11)

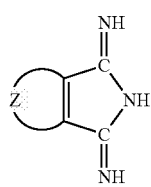
Formula (12)

wherein Z represents an organic moiety for forming a 6-membered aromatic ring structure together with the two carbon atoms bonded to the Z;

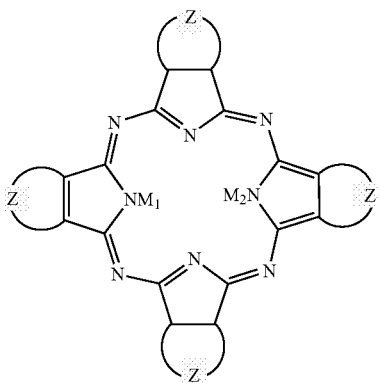

Formula (13)

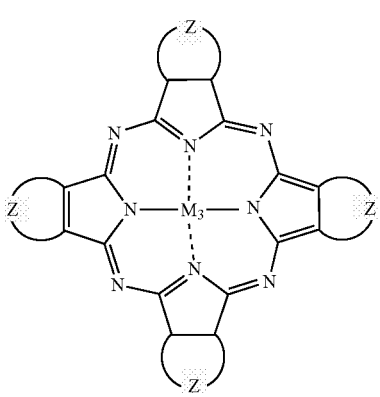

Formula (14)

wherein Z has the same meaning as defined in formulae (11) and (12); $M_1$ and $M_2$ each independently represent an atom in the Group 1 of the periodic table; and $M_3$ represents a metal atom or a metal compound thereof, except an atom in the Group 1 of the periodic table.

(10) A method of producing a phthalocyanine compound represented by formula (13) or (14) shown above, or a phthalocyanine analogue, comprising:

conducting a reaction of a phthalonitrile compound represented by formula (15), in the presence of a dehydrating agent and an ammonium salt compound in combination, thereby producing the phthalocyanine compound represented by formula (13) or (14), or the phthalocyanine analogue:

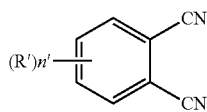

Formula (15)

wherein R' represents a hydrogen atom or a substituent; n' represents an integer of 1 to 4; and when n' is 2 to 4, a plurality of R's may be the same or different from each other or may be bonded to each other to form a ring.

(11) The producing method according to the above item (9) or (10), wherein the ammonium salt compound is an ammonium carboxylate.

(12) The producing method according to any one of the above items (9) to (11), wherein the dehydrating agent is selected from the group consisting of an acetal compound, an orthoester compound, an alkenyl ether compound, an alkenyl ester compound, an epoxide compound, and an oxetane compound.

(13) The producing method according to any one of the above items (9) to (11), wherein the dehydrating agent is an organic compound providing a distillate containing water, after distillation of a mixture of the organic compound and water under atmospheric pressure or reduced pressure.

(14) The producing method according to any one of the above items (9) to (13), further comprising conducting a reaction in the presence of an acid in combination.

(15) The producing method according to the above item (14), wherein the acid is a carboxylic acid.

Hereinafter, a first embodiment of the present invention means to include the methods of producing a metal phthalocyanine compound, as described in the items (1) to (8) above.

Further, a second embodiment of the present invention means to include the methods of producing the phthalocyanine compound or phthalocyanine analogue, as described in the items (9) to (15) above.

Herein, the present invention means to include both of the above first and second embodiments, unless otherwise specified.

Other and further features and advantages of the invention will appear more fully from the following description, taken in connection with the accompanying drawings.

BEST MODE FOR CARRYING OUT INVENTION

Figure 1:
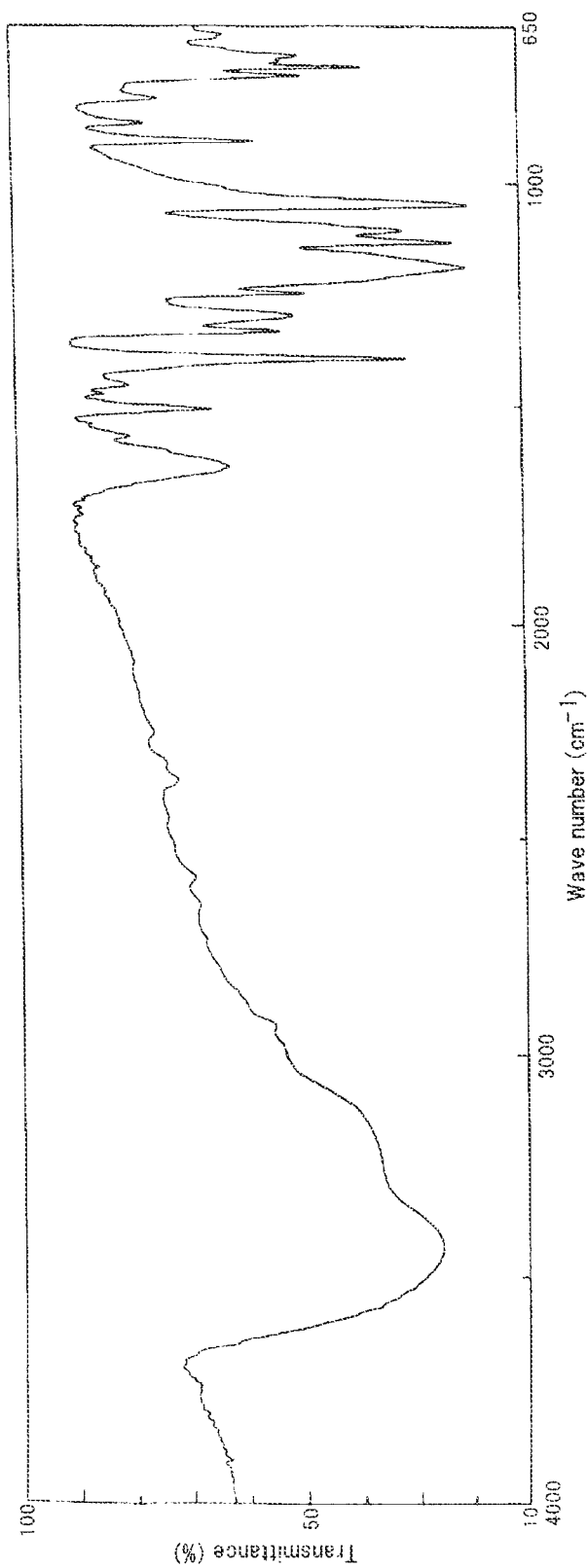
FIG. 1 is an IR spectrum of the phthalocyanine compound 211 obtained in Example 11.

The inventors of the present invention, having conducted detailed studies on a production method providing a high reaction yield under mild conditions, found that it is useful to conduct a reaction in a buffer solution, in the presence of a dehydrating agent, in order to solve the above-mentioned problems; and we attained the present invention based of the finding.

Further, the inventors of the present invention have conducted intensive studies on methods of producing phthalocyanine compounds having various substituents, efficiently, in high yields, and we attained the present invention.

The present invention is described in detail hereinafter.

First, the compound represented by formula (I) is described.

In formula (I), R represents a hydrogen atom or a substituent. Specific examples of the substituent include: a halogen atom (a fluorine atom, a chlorine atom, a bromine atom, or an iodine atom); an alkyl group (a linear or branched, substituted or unsubstituted alkyl group preferably having 1 to 30 carbon atoms, e.g. a methyl group, ethyl group, n-propyl group, isopropyl group, t-butyl group, n-octyl group, eicosyl group, 2-chloroethyl group, 2-cyanoethyl group, 2-ethylhexyl group, or 3-(2,4-di-t-amylphenoxy)propyl group); an aralkyl group (preferably a substituted or unsubstituted aralkyl group having 7 to 30 carbon atoms, e.g. a benzyl group or phenethyl group); a cycloalkyl group (preferably a substituted or unsubstituted cycloalkyl group having 3 to 30 carbon atoms, e.g. a cyclohexyl group, cyclopentyl group, or 4-n-dodecylcyclohexyl group); an alkenyl group (a linear or branched, substituted or unsubstituted alkenyl group preferably having 2 to 30 carbon atoms, e.g. a vinyl group, allyl group, prenyl group, geranyl group, or oleyl group); a cycloalkenyl group (preferably a substituted or unsubstituted cycloalkenyl group having 3 to 30 carbon atoms, e.g. a 2-cyclopenten-1-yl group or 2-cyclohexen-1-yl group); an alkynyl group (a linear or branched, substituted or unsubstituted alkynyl group preferably having 2 to 30 carbon atoms, e.g. an ethynyl group, propargyl group, or trimethylsilylethynyl group); an aryl group (preferably a substituted or unsubstituted aryl group having 6 to 30 carbon atoms, e.g. a phenyl group, p-tolyl group, naphthyl group, m-chlorophenyl group, or o-hexadecanoylaminophenyl group); a heterocyclic group [preferably a 5- to 7-membered, substituted or unsubstituted, saturated or unsaturated, aromatic or non-aromatic, monocyclic or condensation heterocyclic group; more preferably a heterocyclic group which is composed of an atom selected from the group consisting of a carbon atom, a nitrogen atom, an oxygen atom, and a sulfur atom, and which has at least one hetero atom selected from a nitrogen atom, an oxygen atom, and a sulfur atom; further preferably a 5- or 6-membered aromatic heterocyclic group having 3 to 30 carbon atoms (e.g. a 2-furyl group, 2-thienyl group, 2-pyridyl group, 4-pyridyl group, 2-pyrimidinyl group, or 2-benzothiazolyl group); still further preferably a heterocyclic group containing a quaternarized nitrogen atom (e.g. a pyridinio group, imidazolio group, quinolinio group, or isoquinolinio group)]; an acyl group (preferably a formyl group, a substituted or unsubstituted alkylcarbonyl group having 2 to 30 carbon atoms, or a substituted or unsubstituted arylcarbonyl group having 7 to 30 carbon atoms, e.g. an acetyl group, pivaloyl group, 2-chloroacetyl group, stearoyl group, benzoyl group, or p-n-octyloxyphenyl carbonyl group); an alkoxycarbonyl group (preferably a substituted or unsubstituted alkoxycarbonyl group having 2 to 30 carbon atoms, e.g. a methoxycarbonyl group, ethoxycarbonyl group, t-butoxycarbonyl group, or n-octadecyloxycarbonyl group); an aryloxycarbonyl group (preferably a substituted or unsubstituted aryloxycarbonyl group having 7 to 30 carbon atoms, e.g. a phenoxycarbonyl group, o-chlorophenoxycarbonyl group, m-nitrophenoxycarbonyl group, or p-t-butylphenoxycarbonyl group); a carbamoyl group (preferably a substituted or unsubstituted carbamoyl group having 1 to 30 carbon atoms, e.g. a carbamoyl group, N-methylcarbamoyl group, N,N-dimethylcarbamoyl group, N,N-di-n-octylcarbamoyl group, or N-(methylsulfonyl)carbamoyl group); a carboxyl group or a salt thereof; a sulfonylcarbamoyl group (preferably a substituted or unsubstituted sulfonylcarbamoyl group having 2 to 30 carbon atoms, e.g. a methanesulfonylcarbamoyl group, octanesulfonylcarbamoyl group, or benzenesulfonylcarbamoyl group); an acylcarbamoyl group (preferably an acylcarbamoyl group having 2 to 30 carbon atoms, e.g. a formylcarbamoyl group, methylcarbamoyl group, or phenylcarbamoyl group); a sulfamoylcarbamoyl group (preferably a sulfamoylcarbamoyl group having 1 to 30 carbon atoms, e.g. a methylsulfamoylcarbamoyl group or phenylsulfamoylcarbamoyl group); a carbazoyl group (preferably a carbazoyl group having 1 to 30 carbon atoms, e.g. a carbazoyl group, 3-ethylcarbazoyl group, 3,3-dimethylcarbazoyl group, or 2-ethyl-3-phenylcarbazoyl group); an oxalyl group (preferably an oxalyl group having 2 to 30 carbon atoms, e.g. a methyloxalyl group, phenyloxalyl group, ethoxyoxalyl group, or phenoxyoxalyl group); an oxamoyl group (preferably an oxamoyl group having 2 to 30 carbon atoms, e.g. an oxamoyl group, N-ethyloxamoyl group, N-phenyloxamoyl group, or N,N-diethyloxamoyl group); a cyano group; a thiocarbamoyl group (preferably a thiocarbamoyl group having 1 to 30 carbon atoms, e.g. a thiocarbamoyl group, N-ethylthiocarbamoyl group, or N-phenylthiocarbamoyl group); a hydroxy group; an alkoxy group (which may include a group containing repeated ethyleneoxy group units or propyleneoxy group units, the alkoxy group preferably having 1 to 30 carbon atoms, e.g. a methoxy group, ethoxy group, octyloxy group, or hexadecyloxy group); an aryloxy group (preferably a substituted or unsubstituted aryloxy group having 6 to 30 carbon atoms, e.g. a phenyloxy group or naphtyloxy group); a heterocyclicoxy group (preferably a heterocyclicoxy group of the above-described heterocyclic group, e.g. a pyridyloxy group, imidazoyloxy group, or piperidyloxy group); an acyloxy group (preferably an acyloxy group having 1 to 30 carbon atoms, e.g. a formyloxy group, acetyloxy group, or benzoyloxy group); an (alkoxy or aryloxy) carbonyloxy group (preferably an alkoxycarbonyloxy group having 1 to 30 carbon atoms or an aryloxycarbonyloxy group having 6 to 30 carbon atoms, e.g. a methoxycarbonyloxy group or phenoxycarbonyloxy group); a carbamoyloxy group (preferably a carbamoyloxy group having 1 to 30 carbon atoms, e.g. a carbamoyloxy group, ethylcarbamoyloxy group, or phenylcarbamoyloxy group); a sulfonyloxy group (preferably a sulfonyloxy group having 2 to 30 carbon atoms, e.g. a methanesulfonyloxy group or benzenesulfonyloxy group); an amino group; an (alkyl-, aryl-, or heterocyclic)amino group [preferably an amino group which is substituted by any of (an alkyl group having 1 to 30 carbon atoms, an aryl group having 6 to 30 carbon atoms, or a heterocycle of the above-described heterocyclic group), e.g. a methylamino group, diethylamino group, phenylamino group, or pyridylamino group]; an acylamino group (preferably an acylamino group having 1 to 30 carbon atoms, e.g. a formylamino group, acetylamino group, or benzoylamino group); a sulfonamido group (preferably a sulfonamido group having 1 to 30 carbon atoms, e.g. an ethanesulfonamido group or benzenesulfoneamido group); a ureido group (preferably a ureido group having 1 to 30 carbon atoms, e.g. a ureido group, methylureido group, or phenylureido group); a thioureido group (preferably a thioureido group having 1 to 30 carbon atoms, e.g. a methylthioureido group or phenylthioureido group); an imido group (preferably a substituted or unsubstituted imido group having 2 to 30 carbon atoms, e.g. an N-succinimido group or N-phthalimido group); an (alkoxy or aryloxy) carbonylamino group (preferably an alkoxycarbonylamino having 2 to 30 carbon atoms or aryloxycarbonylamino group having 7 to 30 carbon atoms, e.g. a methoxycarbonylamino group or phenoxycarbonylamino group); a sulfamoylamino group (preferably a sulfamoylamino group having 1 to 30 carbon atoms, e.g. a methanesulfamoylamino group or benzenesulfamoylamino group); a semicarbazido group (preferably a semicarbazido group having 1 to 30 carbon atoms, e.g. a semicarbazido group, N-ethylsemicarbazido group, or N-phenylsemicarbazido group); a thiosemicarbazido group (preferably a thiosemicarbazido group having 1 to 30 carbon atoms, e.g. a thiosemicarbazido group, N-butylthiosemicarbazido group, or N-phenylthiosemicarbazido group); a hydrazino group (preferably a hydrazino group having 1 to 30 carbon atoms, e.g. a hydrazino group, ethylhydrazino group, or phenylhydrazino group); an ammonio group; an oxamoylamino group (preferably an oxamoylamino group having 2 to 30 carbon atoms, e.g. an oxamoyl group, ethyloxamoyl group, or phenyloxamoyl group); an (alkyl or aryl) sulfonylureido group (preferably an alkylsulfonylureido group having 2 to 30 carbon atoms or an arylsulfonylureido group having 7 to 30 carbon atoms, e.g. a methanesulfonylureido group or benzenesulfonylureido group); an acylureido group (preferably an acylureido group having 2 to 30 carbon atoms, e.g. a formylureido group, acetylureido group, or benzoylureido group); an acylsulfamoylamino group (preferably an acylsulfamoylamino group having 1 to 30 carbon atoms, e.g. an acetylsulfamoylamino group or benzoylsulfamoylamino group); a nitro group; a mercapto group; an (alkyl-, aryl-, or heterocyclic)thio group [preferably a thio group which is substituted by any of (an alkyl group having 1 to 30 carbon atoms, an aryl group having 6 to 30 carbon atoms, or a heterocycle of the above-described heterocyclic group), e.g. a methylthio group, phenylthio group, or pyridylthio group]; an (alkyl-, aryl-, or heterocyclic)sulfonyl group [preferably a sulfonyl group which is substituted by any of (an alkyl group having 1 to 30 carbon atoms, an aryl group having 6 to 30 carbon atoms, or a heterocycle of the above-described heterocyclic group), e.g. a methylsulfonyl group, phenylsulfonyl group, or pyridylsulfonyl group]; an (alkyl-, aryl-, or heterocyclic)sulfinyl group [preferably a sulfinyl group which is substituted by any of (an alkyl group having 1 to 30 carbon atoms, an aryl group having 6 to 30 carbon atoms, or a heterocycle of the above-described heterocyclic group), e.g. a methylsulfinyl group, phenylsulfinyl group, or pyridylsulfinyl group]; a sulfo group or a salt thereof, a sulfamoyl group (preferably a sulfamoyl group having 0 to 30 carbon atoms, e.g. a sulfamoyl group, ethanesulfamoyl group, or benzenesulfamoyl group); an acylsulfamoyl group (preferably an acylsulfamoyl group having 1 to 30 carbon atoms, e.g. a formylsulfamoyl group, acetylsulfamoyl group, or benzoylsulfamoyl group); a sulfonylsulfamoyl group or a salt thereof (preferably a sulfonylsulfamoyl group of a salt thereof having 0 to 30 carbon atoms, e.g. a methanesulfonylsulfamoyl group or benzenesulfonylsulfamoyl group); a group containing a phosphoric acid amide or phosphoric acid ester structure (preferably a group containing a phosphoric acid amide or phosphoric acid ester structure having 0 to 30 carbon atoms, e.g. a phosphoric acid amido group, methylphosphoric acid amido group, phenylphosphoric acid amido group, ethoxyphosphoric acid amido group, or phenoxyphosphoric acid amido group); a silyloxy group (preferably a silyloxy group having 1 to 30 carbon atoms, e.g. a trimethylsilyloxy group or t-butyldimethylsilyloxy group); and a silyl group (preferably a silyl group having 1 to 30 carbon atoms, e.g. a trimethylsilyl group, t-butyldimethylsilyl group, or phenyldimethylsilyl group).

When R represents a substituent, preferably use can be made of any of: a halogen atom, an alkyl group, an alkenyl group, an alkynyl group, an aryl group, a heterocyclic group, an acyl group, an alkoxycarbonyl group, a carbamoyl group, a carboxyl group or a salt thereof, an oxalyl group, an oxamoyl group, a cyano group, a hydroxy group, an alkoxy group, an aryloxy group, a heterocyclic-oxy group, a sulfonyloxy group, an (alkyl-, aryl-, or heterocyclic)amino group, an acylamino group, a sulfonamido group, a mercapto group, an (alkyl-, aryl-, or heterocyclic)thio group, an (alkyl-, aryl-, or heterocyclic)sulfonyl group, an (alkyl-, aryl-, or heterocyclic) sulfinyl group, a sulfo group or a salt thereof, a sulfamoyl group, or a group containing a phosphoric acid amide or phosphoric acid ester structure. More preferably, use can be made of any of a halogen atom, an alkyl group, an aryl group, a heterocyclic group, an acyl group, a carbamoyl group, a carboxyl group or a salt thereof, an oxamoyl group, an alkoxy group, an aryloxy group, a heterocyclic-oxy group, an (alkyl-, aryl-, or heterocyclic)amino group, an acylamino group, a sulfonamido group, an (alkyl-, aryl-, or heterocyclic)thio group, an (alkyl-, aryl-, or heterocyclic)sulfonyl group, an (alkyl-, aryl-, or heterocyclic)sulfinyl group, a sulfo group or a salt thereof, or a sulfamoyl group. Further preferably, use can be made of any of: a halogen atom, an alkyl group, an aryl group, a heterocyclic group, an acyl group, a carbamoyl group, an oxamoyl group, an alkoxy group, an aryloxy group, a heterocyclic-oxy group, an (alkyl-, aryl-, or heterocyclic) amino group, an acylamino group, a sulfonamido group, an (alkyl-, aryl-, or heterocyclic)thio group, an (alkyl-, aryl-, or heterocyclic)sulfonyl group, or a sulfamoyl group.

When R is a substituent, R is particularly preferably a halogen atom, an acyl group, a carbamoyl group, a sulfamoyl group, a sulfinyl group, or a sulfonyl group; more preferably a carbamoyl group, a sulfamoyl group, a sulfinyl group, or a sulfonyl group; further preferably a sulfamoyl group, or a sulfonyl group; and most preferably a sulfonyl group.

The substituent represented by R may be further substituted. Such a substituted further substituted may include a substituent substituted by any group, and is preferably a substituent substituted by an ionic hydrophilic group. Specifically, preferable examples thereof include those substituted by an ionic hydrophilic group, e.g. a carboxyl group, a sulfo group, a phosphoric acid group, a group having a quaternary salt structure of nitrogen, or a group having a quaternary salt structure of phosphorus.

In the case where the substituent has a carboxyl group, a sulfo group, or a phosphoric acid group as an ionic hydrophilic group, the ionic hydrophilic group may have a counter cation as required. Examples of the counter cation that may be used include a metal ion, a group having a quaternary salt structure of nitrogen, and a group having a quaternary salt structure of phosphorus.

In the case where the substituent has a group having a quaternary salt structure of nitrogen, or a group having a quaternary salt structure of phosphorus as an ionic hydrophilic group, the ionic hydrophilic group may have a counter anion as required. Examples of the counter anion include a halogen ion, a sulfate ion, a nitrate ion, a phosphate ion, an oxalate ion, an alkanesulfonate ion, an arylsulfonate ion, an alkanecarboxylate ion, and an arylcarboxylate ion.

Preferred examples of the ionic hydrophilic group include a carboxyl group, a sulfo group, and a phosphoric acid group, and more preferred examples thereof include a carboxyl group and a sulfo group. In this case, preferred examples of the counter cation that can be used include cations of Li, Na, K, and $NH_4$. More preferred examples thereof include cations of Li and Na, and a particularly preferred example thereof is a cation of Li.

A particularly preferred example of the counter cation for the phthalocyanine compound in the present invention, preferably in the first embodiment of the present invention, is a lithium ion. All cations need not be lithium ions, but it is preferable that counter cation substantially in the highest abundance ratio is lithium ion.

Under conditions of such an abundance ratio, a hydrogen ion, an alkali metal ion (e.g. sodium ion or potassium ion), an alkali earth metal ion (e.g. magnesium ion or calcium ion), a quaternary ammonium ion, a quaternary phosphonium ion, a sulfonium ion, and the like may be contained as other counter cations.

The types and ratios of the counter cations in the phthalocyanine compound are described in detailed sections on analysis method and elements in "Shin Jikken Kagaku Koza 9, Bunseki Kagaku", edited by The Chemical Society of Japan (1977, published by Maruzen Co., Ltd.) and "Jikken Kagaku Koza 15, Bunseki, 4th edition", edited by The Chemical Society of Japan (1991, published by Maruzen Co., Ltd.). Thus, with reference to those books, the analysis method may be selected for analysis and quantitative determination of the counter cations. Of those, an analysis method, e.g. ion chromatography, atomic absorption method, or inductively coupled plasma-atomic emission spectroscopy (ICP) may be used for easy determination of the types and ratios of the counter cations in the phthalocyanine compound.

The ratio of the lithium ion in the phthalocyanine compound, to the total counter ions, is preferably 50% or more, more preferably 60% or more, further preferably 80% or more, particularly preferably 90% or more, and an upper limit thereof is preferably 100%.

In the case where R represents a group having a carbon atom(s), the total number of carbon atom(s) is preferably 1 to 100, more preferably 1 to 80, furthermore preferably 1 to 50, and particularly preferably 1 to 20.

l represents an integer of 0 to 4. l is preferably 1 to 3, and more preferably 1 or 2. In the case where l is 2 to 4, a plurality of Rs exist, and the plurality of Rs may be the same or different from each other.

In production of a phthalocyanine compound from the compound represented by formula (I), four molecules of the compound(s) represented by formula (I) are stoichiometrically required for production of one molecule of the phthalocyanine compound.

Herein, the required four molecules of the compounds represented by formula (I) need not be the same, and a plurality of compounds represented by formula (I) having different Rs may be used in an arbitrary ratio. In the present invention, the four molecules of the compounds represented by formula (I) particularly preferably have at least two different Rs.

When the plurality of compounds represented by formula (I) having different Rs may be used in an arbitrary ratio, the compounds (i.e. Compounds A to F) represented by formula (I) according to the present invention may be selected from the compounds of Compound A in an arbitrary ratio for use, or may be selected from the compounds of Compounds A to F in an arbitrary ratio for use. Of those, it is preferable to select, as the plurality of compounds represented by formula (I) having different Rs, from those of Compound A in an arbitrary ratio for use among the compounds represented by formula (I), from the viewpoint of arbitrarily control of a mixed distribution of different Rs in production of the phthalocyanine compound.

A mixed ratio of the plurality of compounds represented by formula (I) having different Rs to be used has no upper limit or lower limit in accordance with the corresponding phthalocyanine compound. The four molecules of the compounds represented by formula (I) required in production of the phthalocyanine compound are more preferably used in the following ratios:
(1) Two different Rs may be selected: (R1+R2=4).
   R1:R2=0.01~3.99 (eq/eq): 3.99~0.01 (eq/eq)
(2) Three different Rs may each independently be selected arbitrarily from the minimum values to the maximum values of R1 to R3 described below and satisfying an equation (R1+R2+R3=4).
   R1=0.01 to 3.98 (eq)
   R2=0.01 to 3.98 (eq)
   R3=0.01 to 3.98 (eq)
(3) Four different Rs may each independently be selected arbitrarily from the minimum values to the maximum values of R1 to R4 described below and satisfying an equation (R1+R2+R3+R4=4).
   R1=0.01 to 3.97 (eq)
   R2=0.01 to 3.97 (eq)
   R3=0.01 to 3.97 (eq)
   R4=0.01 to 3.97 (eq)

A substitution position of R in the compounds represented by formula (I) may be at any position as long as the substitution is possible, but is preferably at a 4- or 5-position.

G in the compound represented by formula (I) represents a group of atoms necessary for forming at least one of a 5- or 6-membered aromatic ring and a 5- or 6-membered hetero ring, and preferably a 6-membered aromatic ring or a 6-membered hetero ring containing nitrogen. Of those, G in the compound represented by formula (I) preferably represents a group of atoms necessary for forming a 6-membered aromatic ring, a pyridine ring, a pyrazine ring, a pyrimidine ring, or a pyridazine ring, particularly preferably a 6-membered aromatic ring or a pyridine ring, and most preferably a 6-membered aromatic ring.

Of Compounds A to F represented by formula (I), Compounds A, B, and F are preferred. Compounds A and B are more preferred, and Compound A is particularly preferred.

With regard to a combination of preferred substituents for the compounds represented by formula (I) in the present invention, the compounds preferably have at least one preferred substituent of the various substituents. The compounds more preferably have a larger number of preferred substituents of the various substituents. Most preferably, the compounds are those having the substituents that each are the preferred substituents.

The preferred combination of the compounds represented by formula (I) in the present invention includes the following conditions (a1) to (f1):
(a1) R represents a hydrogen atom or a substituent. Preferable examples of the substituent include: a halogen atom, an acyl group, a carbamoyl group, a sulfamoyl group, a sulfinyl group, or a sulfonyl group; more preferably a carbamoyl group, a sulfamoyl group, a sulfinyl group, or a sulfonyl group; particularly preferably a sulfamoyl group, or a sulfonyl group; and most preferably a sulfonyl group.

The substituent represented by R may be further substituted, and a preferred example of the substituent for the further substitution is a substituent substituted by an ionic hydrophilic group.

Specifically, the substituent is preferably substituted by a hydrophilic group, e.g. a carboxyl group, a sulfo group, a phosphoric acid group, a group having a quaternary salt structure of nitrogen, or a group having a quaternary salt structure of phosphorus, more preferably by a carboxyl group or a sulfo group, and particularly preferably by a sulfo group.

In the case where the substituent is substituted by an ionic hydrophilic group, e.g. a carboxyl group, a sulfo group, or a phosphoric acid group, the ionic hydrophilic group may have a counter cation as required. Preferred examples of the counter cation include metal ions, a group having a quaternary salt structure of nitrogen, and a group having a quaternary salt structure of phosphorus. More preferred examples thereof include cations of Li, Na, K, and $NH_4$. Further preferred examples thereof include cations of Li and Na, and a particularly preferred example thereof is a cation of Li.

The ratio of the lithium ion to the total counter ions is preferably 50% or more, more preferably 60% or more, further preferably 80% or more, and particularly preferably 90% or more, and an upper limit thereof is preferably 100%.
(b1) G preferably represents a 6-membered aromatic ring or a 6-membered hetero ring containing nitrogen, more preferably a 6-membered aromatic ring, a pyridine ring, a pyrazine ring, a pyrimidine ring, or a pyridazine ring, particularly preferably a 6-membered aromatic ring or a pyridine ring, and most preferably a 6-membered aromatic ring.
(c1) l represents an integer of 0 to 4, preferably an integer of 0 to 3, more preferably an integer of 0 to 2, and particularly preferably an integer of 0 or 1. A plurality of Rs may be the same or different from each other when l is 2 to 4.

(d1) A substitution position of R in the compounds represented by formula (I) may be at any position as long as the substitution is possible, but is preferably at a 4- or 5-position.

(e1) Of Compounds A to F represented by formula (I), Compounds A, B, and F are preferred. Compounds A and B are more preferred, and Compound A is particularly preferred.

(f1) When the plurality of compounds represented by formula (I) having different Rs may be used in an arbitrary ratio, the compounds represented by formula (I) according to the present invention may be selected from the compounds of Compound A in an arbitrary ratio for use, or may be selected from the compounds of Compounds A to F in an arbitrary ratio for use. Of those, it is preferable to select, as the plurality of compounds represented by formula (I) having different Rs, from those of Compound A in an arbitrary ratio for use among the compounds represented by formula (I), from the viewpoint of arbitrarily control of a mixed distribution of different Rs in production of the phthalocyanine compound.

Of Compounds A to F represented by formula (I), Compounds G to L represented by formula (II) are particularly preferred.

Next, the compounds represented by formula (II) will be described.

In Compounds G to L represented by formula (II): a and b each independently represent a substituent; the sum total of Hammett's constant $\sigma_p$ value of the substituents is 0.20 or more; m and n each represent an integer satisfying: 0≤m≤4, 0≤n≤3, and 0≤m+n≤4; and G represents a group of atoms necessary for forming at least one of 5- or 6-membered aromatic ring and 5- or 6-membered hetero ring.

Herein, the Hammett' constants of substitution $\sigma_p$ values, which are utilized, for example, in the definition of formula (II) in the present specification and claims, are described. The Hammett's rule is an empirical rule proposed by L. P. Hammett in 1935 to quantitatively describe the effect of a substituent on the reaction or equilibrium of a benzene derivative. Presently, the appropriateness of this rule is widely acknowledged. There are $\sigma_p$ and $\sigma_m$ as constants of substitution obtained by the Hammett's rule. These values are described in many common books. For example, details of these values are described in "Lange's Handbook of Chemistry", edited by J. A. Dean, 12th edition, 1979 (McGraw-Hill), and "Extra issue of Kagakuno Ryoiki", No. 122, pp. 96-103, 1979(Nankodo Publishing Co., Ltd.). In the present invention, substituents are defined and explained using Hammett's constant of substitution $\sigma_p$. However, it must be noted that substituents are not necessarily limited to the substituents having Hammett's constants which are known and described in the literature. Therefore, needless to say, even if the Hammett's constant of a substituent is not described in the literature, the substituent whose Hammett's constant falls within the range when measured based on the Hammett's rule is included in the scope of the present invention. Further, as a scale for showing the electron effect of a substituent in interest, the $\sigma_p$ value is utilized regardless of its substituting position. In the present invention, the $\sigma_p$ value is used in the above meaning.

In Compounds G to L represented by formula (II), the substituent represented by a or b preferably represents a halogen atom, an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

Such a group preferably has a substituent, e.g. an ionic hydrophilic group, and/or an alkyl group or aryl group having an ionic hydrophilic group as a substituent thereon.

Examples of the ionic hydrophilic group as a substituent in formula (II) has the same meaning as the ionic hydrophilic group described for formula (I), and preferred examples thereof are also the same as those for formula (I).

G in formula (II) has the same meaning as G described for formula (I), and preferred examples thereof are the same as those for formula (I).

m in formula (II) represents an integer of 0 to 4, preferably an integer of 0 to 2, more preferably 1 or 2, and most preferably 1.

n in formula (II) represents an integer of 0 to 3, preferably an integer of 0 to 2, more preferably 0 or 1, and most preferably 0.

Of Compounds G to L represented by formula (II), Compounds G, H, and L are preferred. Compounds G and H are more preferred, and Compound G is particularly preferred.

Of the compounds represented by formula (II) according to the present invention, at least two compounds of the compounds (Compounds G to L) represented by formula (II) may be selected from the compounds of Compound G in an arbitrary ratio, or may be selected from the compounds of Compounds G to L in an arbitrary ratio. Of those, it is preferable to select, as the at least two compounds, from those of Compound G in an arbitrary ratio for use among the compounds represented by formula (II), from the viewpoint of arbitrarily control of a mixed distribution of different dyes in production of the phthalocyanine compound.

With regard to a combination of preferred substituents for the compounds represented by formula (II) in the present invention, the compounds preferably have at least one preferred substituent of the various substituents. The compounds more preferably have a larger number of preferred substituents of the various substituents. Most preferably, the compounds are those having the substituents that each are the preferred substituents.

The preferred combination of the compounds represented by formula (II) in the present invention includes the following conditions (a2) to (g2):

(a2) Preferable examples of the substituent represented by a or b include: a halogen atom, an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

The substituent represented by a or b may be further substituted, and a preferred example of the substituted substituent is a substituent substituted by an ionic hydrophilic group.

Examples of the ionic hydrophilic group has the same meaning as the ionic hydrophilic group described for formula (I), and preferred examples thereof are also the same as those for formula (I).

(b2) G preferably represents a 6-membered aromatic ring or a 6-membered hetero ring containing nitrogen, more preferably a 6-membered aromatic ring, a pyridine ring, a pyrazine ring, a pyrimidine ring, or a pyridazine ring, particularly preferably a 6-membered aromatic ring or a pyridine ring, and most preferably a 6-membered aromatic ring.

(c2) m represents an integer of 0 to 4, preferably 0 to 2, more preferably 1 or 2, and most preferably 1.

(d2) n represents an integer of 0 to 3, preferably 0 to 2, more preferably 0 or 1, and most preferably 0.

(e2) A substitution position of a and/or b in the compounds represented by formula (II) may be at any position as long as the substitution is possible, but is preferably at a 4- or 5-position.

(f2) Of Compounds G to L, Compounds G, H, and L are preferred; Compounds G and H are more preferred; and Compound G is particularly preferred.

(g2) Of the compounds represented by formula (II) according to the present invention, at least two compounds of the compounds (Compounds G to L) represented by formula (II) may be selected from the compounds of Compound G in an arbitrary ratio, or may be selected from the compounds of Compounds G to L in an arbitrary ratio. Of those, it is preferable to select, as the at least two compounds, from those of Compound G in an arbitrary ratio for use among the compounds represented by formula (II), from the viewpoint of arbitrarily control of a mixed distribution of different dyes in production of the phthalocyanine compound.

Of Compounds G to L represented by formula (II), Compounds M to R represented by formula (III) are particularly preferred.

Next, the compounds represented by formula (III) will be described.

In Compounds M to R represented by formula (III), the substituent represented by $a_1$ preferably represents an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

Such a group preferably has a substituent, e.g. an ionic hydrophilic group, and/or an alkyl group or aryl group having an ionic hydrophilic group as a substituent thereon.

Examples of the ionic hydrophilic group as a substituent in formula (III) has the same meaning as the ionic hydrophilic group described for formula (I), and preferred examples thereof are also the same as those for formula (I).

G in formula (III) has the same meaning as G described for formula (I), and preferred examples thereof are the same as those for formula (I).

$m_1$ in formula (III) represents an integer of 0 to 2, more preferably 1 or 2, and most preferably 1.

Of Compounds M to R represented by formula (III), Compounds M, N, and R are preferred. Compounds M and N are more preferred, and Compound M is particularly preferred.

Of the compounds represented by formula (III) according to the present invention, at least two compounds of the compounds (Compounds M to R) represented by formula (III) may be selected from the compounds of Compound M in an arbitrary ratio, or may be selected from the compounds of Compounds M to R in an arbitrary ratio. Of those, it is preferable to select, as the at least two compounds, from those of Compound M in an arbitrary ratio for use among the compounds represented by formula (III), from the viewpoint of arbitrarily control of a mixed distribution of different dyes in production of the phthalocyanine compound.

With regard to a combination of preferred substituents for the compounds represented by formula (III) in the present invention, the compounds preferably have at least one preferred substituent of the various substituents. The compounds more preferably have a larger number of preferred substituents of the various substituents. Most preferably, the compounds are those having the substituents that each are the preferred substituents.

The preferred combination of the compounds represented by formula (III) in the present invention includes the following conditions (a3) to (f3):

(a3) Preferable examples of the substituent represented by $a_1$ include: an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

The substituent represented by $a_1$ may further have a substituent. Such a substituted substituent is preferably a group having an ionic hydrophilic group as a substituent thereon.

Examples of the ionic hydrophilic group has the same meaning as that described for formula (I), and preferred examples thereof are also the same as those for formula (I).

(b3) G preferably represents a 6-membered aromatic ring or a 6-membered hetero ring containing nitrogen, more preferably a 6-membered aromatic ring, a pyridine ring, a pyrazine ring, a pyrimidine ring, or a pyridazine ring, particularly preferably a 6-membered aromatic ring or a pyridine ring, and most preferably a 6-membered aromatic ring.

(c3) $m_1$ represents an integer of 0 to 2, more preferably 1 or 2, and most preferably 1.

(d3) A substitution position of $a_1$ in the compounds represented by formula (III) may be at any position as long as the substitution is possible, but is preferably at a 4- or 5-position.

(e3) Of Compounds M to R, Compounds M, N, and R are preferred; Compounds M and N are more preferred; and Compound M is particularly preferred.

(f3) Of the compounds represented by formula (III) according to the present invention, at least two compounds of the compounds (Compounds M to R) represented by formula (III) may be selected from the compounds of Compound M in an arbitrary ratio, or may be selected from the compounds of Compounds M to R in an arbitrary ratio. Of those, it is preferable to select, as the at least two compounds, from those of Compound M in an arbitrary ratio for use among the compounds represented by formula (III), from the viewpoint of arbitrarily control of a mixed distribution of different dyes in production of the phthalocyanine compound.

Of Compounds M to R represented by formula (III), Compounds S to X represented by formula (IV) are particularly preferred.

Next, the compounds represented by formula (IV) will be described.

In Compounds S to X represented by formula (IV), the substituent represented by $a_1$ preferably represents an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

Such a group preferably has a substituent, e.g. an ionic hydrophilic group, and/or an alkyl group or aryl group having an ionic hydrophilic group as a substituent thereon.

Examples of the ionic hydrophilic group as a substituent in formula (IV) has the same meaning as the ionic hydrophilic group described for formula (I), and preferred examples thereof are also the same as those for formula (I).

G in formula (IV) has the same meaning as G described for formula (I), and preferred examples thereof are the same as those for formula (I).

$m_1$ in formula (IV) represents an integer of 0 to 2, more preferably 1 or 2, and most preferably 1.

Of Compounds S to X represented by formula (IV), Compounds S, U, and W are preferred. Compounds S and W are more preferred, and Compound S is particularly preferred.

Of the compounds represented by formula (IV) according to the present invention, at least two compounds of the compounds (Compounds S to X) represented by formula (IV) may be selected from the compounds of Compound S in an arbitrary ratio, or may be selected from the compounds of Compounds S to X in an arbitrary ratio. Of those, it is preferable to select, as the at least two compounds, from those of Compound S in an arbitrary ratio for use among the compounds represented by formula (IV), from the viewpoint of arbitrarily control of a mixed distribution of different dyes in production of the phthalocyanine compound.

With regard to a combination of preferred substituents for the compounds represented by formula (IV) in the present invention, the compounds preferably have at least one preferred substituent of the various substituents. The compounds more preferably have a larger number of preferred substituents of the various substituents. Most preferably, the compounds are those having the substituents that each are the preferred substituents.

The preferred combination of the compounds represented by formula (IV) in the present invention includes the following conditions (a4) to (e4):

(a4) Preferable examples of the substituent represented by $a_1$ include: an acyl group, a carbamoyl group, a sulfamoyl group, a sulfinyl group, or a sulfonyl group, more preferably a carbamoyl group, a sulfamoyl group, a sulfinyl group, or a sulfonyl group, particularly preferably a sulfamoyl group or sulfonyl group, and most preferably a sulfonyl group.

The substituent represented by $a_1$ may further have a substituent. Such a substituted substituent is preferably a group having an ionic hydrophilic group as a substituent thereon.

Examples of the ionic hydrophilic group has the same meaning as that described for formula (I), and preferred examples thereof are also the same as those for formula (I).

(b4) G preferably represents a 6-membered hetero ring containing nitrogen, more preferably a pyridine ring, a pyrazine ring, a pyrimidine ring, or a pyridazine ring, and most preferably a pyridine ring.

(c4) $m_1$ represents an integer of 0 to 2, more preferably 1 or 2, and most preferably 1.

(d4) Of Compounds S to X, Compounds S, T, and W are preferred; Compounds S and W are more preferred; and Compound S is particularly preferred.

(e4) Of the compounds represented by formula (IV) according to the present invention, at least two compounds of the compounds (Compounds S to X) represented by formula (IV) may be selected from the compounds of Compound S in an arbitrary ratio, or may be selected from the compounds of Compounds S to X in an arbitrary ratio. Of those, it is preferable to select, as the at least two compounds, from those of Compound S in an arbitrary ratio for use among the compounds represented by formula (IV), from the viewpoint of arbitrarily control of a mixed distribution of different dyes in production of the phthalocyanine compound.

Next, the dehydrating agent, that can be used in the present invention, preferably in the first embodiment of the present invention, will be described.

Examples of the dehydrating agent include: a dehydrating agent absorbing water molecules (e.g. Molecular sieves (registered trademark), Drierite (registered trademark), magnesium sulfate, or sodium sulfate); a dehydrating agent boiling together with water and exhibiting a dehydration effect (e.g. benzene, toluene, xylene, ethanol, methanol, or acetonitrile); and a dehydrating agent causing a chemical reaction with water [e.g. an organometallic compound (e.g. a Grignard reaction agent, an organolithium reaction agent, or an organozinc reaction agent), an acid anhydride (a carboxylic anhydride, a sulfonic anhydride, or a mixed acid anhydride), an acid halide, polyphosphoric acid, phosphorus pentaoxide, phosphorus oxychloride, phosphorus pentachloride, phosphorus trichloride, an orthoester compound, an acetal compound, an alkenyl ether compound, an alkenyl ester compound, an oxirane compound, or an oxetane compound].

The dehydrating agent to be used is preferably a dehydrating agent causing a chemical reaction with water. The dehydrating agent to be used is more preferably an acetal compound, an orthoester compound, an alkenyl ether compound, an alkenyl ester compound, an epoxide compound, or an oxetane compound, furthermore preferably an acetal compound, an orthoester compound, or an alkenyl ether compound. In the case where the dehydrating agent to be used is a substance containing a carbon atom(s), the total number of carbon atom(s) is generally 1 to 50, preferably 1 to 30, and more preferably 1 to 20.

Next, specifically preferred examples of the dehydrating agent will be shown below, but the present invention is not limited to these.

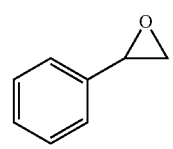

D-1

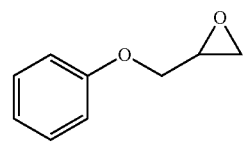

D-2

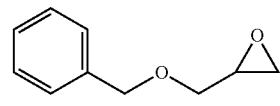

D-3

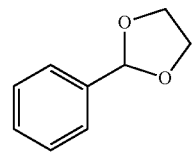

D-4

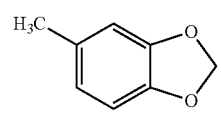

D-5

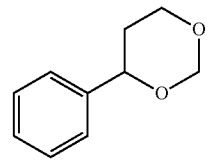

D-6

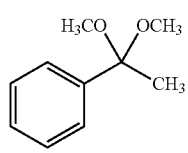
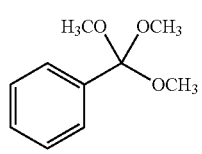
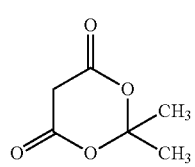
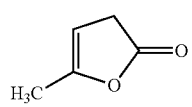
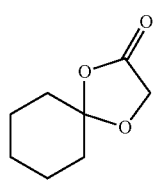
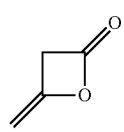
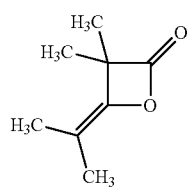
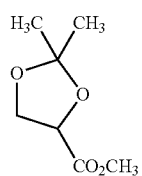
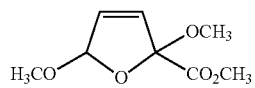
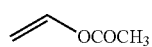
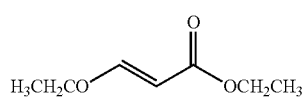
D-7
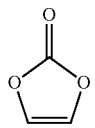
D-8
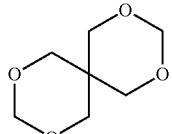
D-9
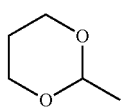
D-10
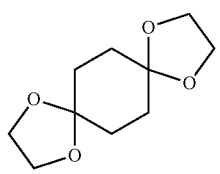
D-11
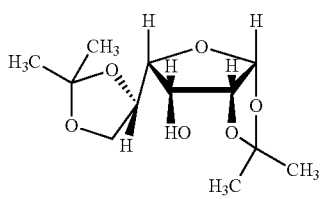
D-12
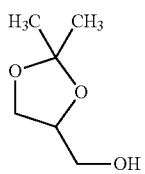
D-13
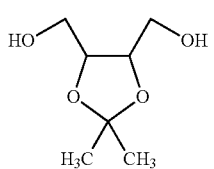
D-14
D-15
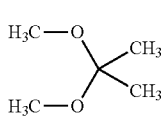
D-16
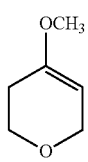
D-17

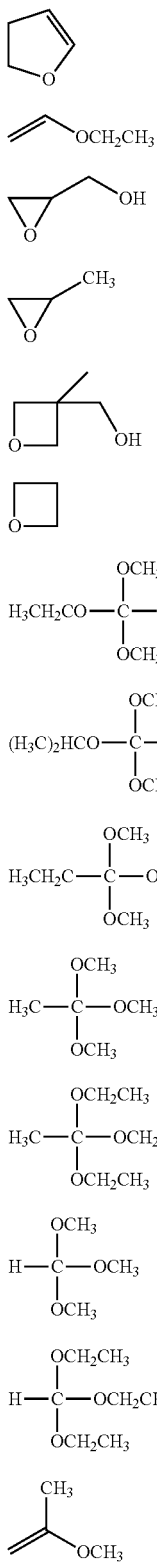

It is necessary to add the dehydrating agent in an amount capable of removing water in a reaction mixture to a level providing no effect on a phthalocyanine production reaction, and a necessary amount of the dehydrating agent is determined by the amount of water in the reaction mixture and the dehydration efficiency of the dehydrating agent to be used. Thus, the necessary amount of the dehydrating agent is determined case by case, and cannot be defined uniformly. The amount of the dehydrating agent to be added is preferably 0.1 to 500 equivalents with respect to the amounts of the compounds represented by any of formulae (I) to (IV).

The dehydrating agent may be added at any stage of the reaction, but is preferably added before starting the reaction, i.e. at the time when placing reaction substrates in a reaction vessel. In the case where operations, e.g. heating, conducting pressure reduction, and conducting reaction in a stream of an inert gas, are required, as auxiliary operations for improving the dehydration efficiency of the dehydrating agent, any appropriate operations may be performed.

The base that can be used in this reaction include an inorganic base including alkali metal, or an organic base.

Examples of the preferable inorganic base include lithium carbonate, sodium carbonate, potassium carbonate, sodium hydrogen carbonate, lithium hydroxide, sodium hydroxide, and potassium hydroxide.

Other examples of the base include lithium acetate, potassium acetate, lithium benzoate, ammonium benzoate, sodium oxalate, and disodium ethylene diaminetetraacetate.

Those alkali metal salts of organic acids are also defined as inorganic bases in the present invention.

Of those, an ammonium salt of a carboxylic acid is particularly preferred.

Preferred examples of the ammonium salt of a carboxylic acid that can be used in the present invention include: an ammonium salt of an aliphatic carboxylic acid; an ammonium salt of an aromatic carboxylic acid; and an ammonium salt of a heterocyclic carboxylic acid. A carboxylic acid in those salts may be a monocarboxylic acid, or a dicarboxylic acid or polycarboxylic acid having two or more carboxyl groups, but is preferably a monocarboxylic acid.

A preferred example of the ammonium salt of an aliphatic carboxylic acid is an ammonium salt of a saturated or unsaturated, linear, branched, or cyclic, and substituted or unsubstituted aliphatic carboxylic acid having 1 to 30 carbon atoms (more preferably 1 to 10 carbon atoms). Specific examples thereof include ammonium formate, diammonium oxalate, ammonium acetate, ammonium propionate, ammonium butanoate, ammonium butyrate, ammonium acrylate, and ammonium cyclohexanecarboxylate.

A preferred example of the ammonium salt of an aromatic carboxylic acid is an ammonium salt of a substituted or unsubstituted aromatic carboxylic acid having 7 to 30 carbon atoms. Specific examples thereof include ammonium benzoate, ammonium toluate, and diammonium phthalate. A preferred example of the ammonium salt of a heterocyclic carboxylic acid is an ammonium salt of a saturated or unsaturated, and substituted or unsubstituted heterocyclic carboxylic acid having 1 to 30 carbon atoms (more preferably 3 to 10 carbon atoms). Specific examples thereof include ammonium nicotinate, ammonium isonicotinate, and ammonium 1-pyrrolecarboxylate.

Of those, the ammonium salt of a carboxylic acid is preferably an ammonium salt of an aliphatic carboxylic acid, or an ammonium salt of an aromatic carboxylic acid; more preferably an ammonium salt of a saturated aliphatic carboxylic acid having 1 to 6 carbon atoms, or an ammonium salt of an aromatic carboxylic acid having 7 to 10 carbon atoms; further preferably ammonium acetate, ammonium propionate, or ammonium benzoate; and particularly preferably ammonium acetate or ammonium benzoate.

Examples of the organic base that can be preferably used include amines, e.g. triethylamine, tributylamine, diisopropylethylamine, pyridine, and dimethylaminopyridine.

Preferred examples thereof include at least one selected from the compounds represented by formula (VI).

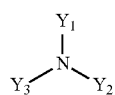

Formula (VI)

In formula (VI), $Y_1$, $Y_2$, and $Y_3$ each independently represent a hydrogen atom, an alkyl group, an alkenyl group, an alkynyl group, a cycloalkyl group, a cycloalkenyl group, an aryl group, or a heterocyclic group, each of which may have a substituent. Examples of the substituent include: a linear or branched alkyl group preferably having 1 to 30 carbon atoms (more preferably 1 to 12 carbon atoms); an aralkyl group preferably having 7 to 30 carbon atoms (more preferably 7 to 18 carbon atoms); an alkenyl group preferably having 2 to 30 carbon atoms (more preferably 2 to 12 carbon atoms); a linear or branched alkynyl group preferably having 2 to 30 carbon atoms (more preferably 2 to 12 carbon atoms); a cycloalkyl group preferably having 3 to 30 carbon atoms (more preferably 3 to 12 carbon atoms), which may have a side chain; a cycloalkenyl group preferably having 3 to 30 carbon atoms (more preferably 3 to 12 carbon atoms), which may have a side chain (specific examples of the above-described groups include a methyl group, ethyl group, propyl group, isopropyl group, t-butyl group, 2-methanesulfonylethyl group, 3-phenoxypropyl group, trifluoromethyl group, or cyclopentyl group); an aryl group (preferably a substituted or unsubstituted aryl group having 6 to 30 carbon atoms (more preferably 6 to 18 carbon atoms), e.g. a phenyl group, 4-t-butylphenyl group, or 2,4-di-t-amylphenyl group); a heterocyclic group (preferably a monovalent group obtained by removing one hydrogen atom from a 5- or 6-membered, substituted or unsubstituted, aromatic or non-aromatic heterocyclic compound, more preferably a 5- or 6-membered aromatic heterocyclic group having 3 to 30 carbon atoms, e.g. an imidazolyl group, pirazolyl group, triazolyl group, 2-furyl group, 2-thienyl group, 2-pyrimidinyl group, or 2-benzothiazolyl group), and the like. Further, two or more of $Y_1$, $Y_2$, and $Y_3$ may form a ring. Preferred examples of the ring include pyridine, imidazole, diazabicycloundecene, piperidine, morpholine, and azacrown; more preferably pyridine, imidazole, piperidine, and morpholine; and further preferably pyridine, piperidine, and morpholine.

Preferably, the group represented by any of $Y_1$, $Y_2$, and $Y_3$ is an alkyl group, a cycloalkyl group, an aryl group, or a heterocyclic group; more preferably an alkyl group, an aryl group, or a heterocyclic group; and most preferably an alkyl group, each of which group may further have a substituent. Examples of the substituent include: a linear or branched alkyl group preferably having 1 to 30 carbon atoms (more preferably 1 to 12 carbon atoms); an aralkyl group preferably having 7 to 30 carbon atoms (more preferably 7 to 18 carbon atoms); an alkenyl group preferably having 2 to 30 carbon atoms (more preferably 2 to 12 carbon atoms); a linear or branched alkynyl group preferably having 2 to 30 carbon atoms (more preferably 2 to 12 carbon atoms); a cycloalkyl group preferably having 3 to 30 carbon atoms (more preferably 3 to 12 carbon atoms), which may have a side chain; a cycloalkenyl group preferably having 3 to 30 carbon atoms (more preferably 3 to 12 carbon atoms), which may have a side chain (specific examples of the above-described groups include a methyl group, ethyl group, propyl group, isopropyl group, t-butyl group, 2-methanesulfonylethyl group, 3-phenoxypropyl group, trifluoromethyl group, or cyclopentyl group); an aryl group (preferably a substituted or unsubstituted aryl group having 6 to 30 carbon atoms (more preferably 6 to 18 carbon atoms), e.g. a phenyl group, 4-t-butylphenyl group, or 2,4-di-t-amylphenyl group); a heterocyclic group (preferably a monovalent group obtained by removing one hydrogen atom from a 5- or 6-membered, substituted or unsubstituted, aromatic or non-aromatic heterocyclic compound, more preferably a 5- or 6-membered aromatic heterocyclic group having 3 to 30 carbon atoms, e.g. an imidazolyl group, pirazolyl group, triazolyl group, 2-furyl group, 2-thienyl group, 2-pyrimidinyl group, or 2-benzothiazolyl group); a halogeno group (i.e. a halogen atom; e.g. a fluorine atom, a chlorine atom, or a bromine atom); an alkyloxy group (preferably a substituted or unsubstituted alkyloxy group having 1 to 30 carbon atoms, more preferably having 1 to 12 carbon atoms, e.g. a methoxy group, ethoxy group, 2-methoxyethoxy group, or 2-methanesulfonylethoxy group); an aryloxy group (preferably a substituted or unsubstituted aryloxy group having 6 to 30 carbon atoms, more preferably having 6 to 18 carbon atoms, e.g. a phenoxy group, 2-methylphenoxy group, 4-t-butylphenoxy group, 3-nitrophenoxy group, 3-t-butyloxycarbamoylphenoxy group, or 3-methoxycarbamoylphenoxy group); an acylamino group (preferably, a formylamino group, a substituted or unsubstituted alkylcarbonylamino group having 1 to 30 carbon atoms (more preferably 1 to 12 carbon atoms), a substituted or unsubstituted arylcarbonylamino group having 6 to 30 carbon atoms (more preferably 6 to 18 carbon atoms), e.g. a formamido group, acetamido group, benzamido group, or 4-(3-t-butyl-4-hydroxyphenoxy)butanamido group); an alkylamino group (preferably a substituted or unsubstituted alkylamino group having 1 to 30 carbon atoms (more preferably 1 to 12 carbon atoms), e.g. a methylamino group, butylamino group, diethylamino group, or methylbutylamino group); an arylamino group (preferably a substituted or unsubstituted arylamino group having 6 to 30 carbon atoms (more preferably 6 to 18 carbon atoms), e.g. a phenylamino group or 2-chloroanilino group); a ureido group (preferably a substituted or unsubstituted ureido group having 1 to 30 carbon atoms (more preferably 1 to 12 carbon atoms), e.g. a phenylureido group, methylureido group, or N,N-dibutylureido group); a sulfamoylamino group (preferably a substituted or unsubstituted sulfamoylamino group having 0 to 30 carbon atoms (more preferably 0 to 18 carbon atoms), e.g. an N,N-dipropylsulfamoylamino group); an alkylthio group (preferably a substituted or unsubstituted alkylthio group having 1 to 30 carbon atoms (more preferably 1 to 12 carbon atoms), e.g. a methylthio group, octylthio group, or 2-phenoxyethylthio group); an arylthio group (preferably a substituted or unsubstituted arylthio group having 6 to 30 carbon atoms (more preferably 6 to 18 carbon atoms), e.g. a phenylthio group, 2-butoxy-5-t-octylphenylthio group, or 2-carboxyphenylthio group); an alkyloxycarbonylamino group (preferably a substituted or unsubstituted alkyloxycarbonylamino group having 2 to 30 carbon atoms (more preferably 2 to 12 carbon atoms), e.g. a methoxycarbonylamino group); a sulfonamido group (preferably, a substituted or unsubstituted alkylsulfonylamino group having 1 to 30 carbon atoms (more preferably 1 to 12 carbon atoms), or a substituted or unsubstituted arylsulfonylamino group having 6 to 30 carbon atoms (more preferably 6 to 18 carbon atoms), e.g. a methanesulfonamido group, benzenesulfonamido group, p-toluenesulfonamido group, or octadecanesulfonamido group); a carbamoyl group (preferably a substituted or unsubstituted carbamoyl group having 1 to 30 carbon atoms (more preferably 1 to 12 carbon atoms), e.g. an N-ethylcarbamoyl group, N,N-dibutylcarbamoyl group, or 3-methoxycarbamoyl group); a sulfamoyl group (preferably a substituted or unsubstituted sulfamoyl group having 0 to 30 carbon atoms, e.g. an N-ethylsulfamoyl group, N,N-dipropylsulfamoyl group, or N,N-diethylsulfamoyl group); a sulfonyl group (preferably, a substituted or unsubstituted alkylsulfonyl group having 1 to 30 carbon atoms (more preferably 1 to 12 carbon atoms), or a substituted or unsubstituted arylsulfonyl group having 6 to 30 carbon atoms (more preferably 6 to 18 carbon atoms), e.g. a methanesulfonyl group, octanesulfonyl group, benzenesulfonyl group, or toluenensulfonyl group); an alkyloxycarbonyl group (preferably a substituted or unsubstituted alkyloxycarbonyl group having 2 to 30 carbon atoms (more preferably 2 to 12 carbon atoms), e.g. a methoxycarbonyl group or butyloxycarbonyl group); a heterocyclicoxy group (preferably a substituted or unsubstituted heterocyclicoxy group having 2 to 30 carbon atoms (more preferably 2 to 12 carbon atoms), e.g. a 1-phenyltetrazol-5-oxy group or 2-tetrahydropyranyloxy group); an azo group (preferably, a substituted or unsubstituted arylazo group having 6 to 30 carbon atoms (more preferably 6 to 18 carbon atoms), or a substituted or unsubstituted heterocyclic azo group having 3 to 30 carbon atoms, e.g. a phenylazo group, 4-methoxyphenylazo group, 4-pivaloylaminophenylazo group, or 2-hydroxy-4-propanoylphenylazo group); an acyloxy group (preferably, a formyloxy group, a substituted or unsubstituted alkyl carbonyloxy group having 2 to 30 carbon atoms (more preferably 2 to 12 carbon atoms), or a substituted or unsubstituted arylcarbonyloxy group having 7 to 30 carbon atoms (more preferably 7 to 18 carbon atoms), e.g. an acetoxy group); a carbamoyloxy group (preferably a substituted or unsubstituted carbamoyloxy group having 1 to 30 carbon atoms (more preferably 1 to 12 carbon atoms), e.g. an N-methylcarbamoyloxy group or N-phenylcarbamoyloxy group); a silyloxy group (preferably a silyloxy group having 3 to 20 carbon atoms (more preferably 3 to 12 carbon atoms), e.g. a trimethylsilyloxy group or dibutylmethylsilyloxy group); an aryloxycarbonylamino group (preferably a substituted or unsubstituted aryloxycarbonylamino group having 7 to 30 carbon atoms (more preferably 7 to 18 carbon atoms), e.g. a phenoxycarbonylamino group); an imido group (e.g. an N-succinimido group or N-phthalimido group); a heterocyclic thio group (preferably a substituted or unsubstituted heterocyclic thio group having 2 to 30 carbon atoms (more preferably 2 to 12 carbon atoms), e.g. a 2-benzothiazolylthio group, 2,4-di-phenoxy-1,3,5-triazol-6-thio group, or 2-pyridylthio group); a sulfinyl group (preferably, a substituted or unsubstituted alkylsulfinyl group having 1 to 30 carbon atoms (more preferably 1 to 12 carbon atoms), or a substituted or unsubstituted arylsulfinyl group having 6 to 30 carbon atoms (more preferably 6 to 18 carbon atoms), e.g. a 3-phenoxypropylsulfinyl group); a phosphonyl group (e.g. a phenoxyphosphonyl group, octyloxyphosphonyl group, or phenylphosphonyl group); an aryloxycarbonyl group (preferably a substituted or unsubstituted aryloxycarbonyl group having 7 to 30 carbon atoms (more preferably 7 to 18 carbon atoms), e.g. a phenoxycarbonyl group); an acyl group (preferably, a formyl group, a substituted or unsubstituted alkyl carbonyl group having 2 to 30 carbon atoms (more preferably 2 to 12 carbon atoms), a substituted or unsubstituted arylcarbonyl group having 7 to 30 carbon atoms (more preferably 7 to 18 carbon atoms), or a substituted or unsubstituted heterocyclic carbonyl group having 4 to 30 carbon atoms (more preferably 4 to 12 carbon atoms) in which the carbonyl group bonds to a carbon atom in the heterocycle, e.g. an acetyl group, 3-phenylpropanoyl group, or benzoyl group); and an ionic hydrophilic group (e.g. a carboxyl group, a phosphono group, a sulfo group, or a quaternary ammonium group); as well as a cyano group, a hydroxyl group, a nitro group, and an amino group. Examples of a preferable substituent include a heterocyclic group, an alkyloxy group, an aryloxy group, an alkylamino group, an arylamino group, an alkylthio group, an arylthio group, an acyl group, an alkylcarbonyl group, an arylcarbonyl group, a heterocyclic carbonyl group, an ionic hydrophilic group, a hydroxyl group, and an amino group. More preferable examples thereof include a heterocyclic group, an alkyloxy group, an aryloxy group, an alkylamino group, an arylamino group, an acyl group, an alkylcarbonyl group, an arylcarbonyl group, a heterocyclic carbonyl group, an ionic hydrophilic group, a hydroxyl group, and an amino group. Still more preferable examples thereof include an alkylcarbonyl group, an arylcarbonyl group, a heterocyclic carbonyl group, an ionic hydrophilic group, a hydroxyl group, and an amino group.

Particularly preferable examples of $Y_1$, $Y_2$, and $Y_3$ include an alkyl group, a cycloalkyl group, an aryl group, and a heterocyclic group, each having a preferable substituent. More preferable examples thereof include an alkyl group, an aryl group, and a heterocyclic group. A still more preferable example thereof is an alkyl group. In addition to the above, amines having chelating ability to metals are preferable.

Most preferable examples of the organic base include triethylamine, tributylamine, diisopropylethylamine, pyridine, dimethylaminopyridine, ethanolamine, diethanolamine, triethanolamine, oxine, ethylenediamine, triethylenetriamine, glycine, iminoacetic acid, and ethylenediaminetetraacetic acid. More preferable examples thereof include triethylamine, pyridine, ethanolamine, diethanolamine, triethanolamine, oxine, ethylenediamine, triethylenetriamine, glycine, iminoacetic acid, and ethylenediaminetetraacetic acid. Most preferable examples thereof include ethanolamine, diethanolamine, triethanolamine, ethylenediamine, triethylenetriamine, and ethylenediaminetetraacetic acid.

In the present invention, preferably in the first embodiment of the present invention, any of the organic base and inorganic base may be used singly, or they may be used in combination. Since the base is dissolved in a reaction solvent to serve as a buffer solution, a base high in solubility is preferred. An ammonium salt of a carboxylic acid as an inorganic base, and an organic base are more preferred, and an organic acid salt containing an alkali metal ion or ammonium ion as a cation is further preferred.

Of the ammonium salts of carboxylic acids, an aliphatic ammonium salt and an aromatic ammonium salt are particularly preferred, and an aromatic ammonium salt is most preferred.

The amount of the base to be used in the present invention, preferably in the first embodiment of the present invention, is generally 0.05 to 30.0 equivalents, and preferably 0.5 to 15.0 equivalents, with respect to the amount to be used of the compound represented by any of formulae (I) to (IV).

The amount to be used of the ammonium salt of a carboxylic acid is more preferably in the range of 0.01 to 2,000 equivalents with respect to the amounts to be used of the compound represented by any of formula (I) to (IV). The amount to be used of the ammonium salt of a carboxylic acid is preferably in the range of 1 to 1,000 equivalents, more preferably in the range of 20 to 500 equivalents, and further preferably in the range of 50 to 400 equivalents.

As described above, in production of a metal phthalocyanine compound by using at least one compound selected from Compounds A to F represented by formula (I), and a metal compound, use of a base as a catalyst for condensation of phthalocyanine may advance the reaction efficiently.

However, decomposition of phthalonitrile accelerates in the case where Compounds A to F represented by formula (I) are compounds each having an electron withdrawing group, and more specifically in the case where Compounds G to L represented by formula (II) are bases, and in the case where Compounds A and/or G are used, for example. In particular, decomposition is significant in the case where a metal phthalocyanine compound having an electron withdrawing group high in a $\sigma_p$ value as a group substituted thereon is used.

However, the decomposition can be controlled by allowing an acid to be coexistent in the reaction system. That is, the reaction system consequently becomes a buffer solution containing an acid and a base, and thus the reaction advances in high yield without decomposition of Compounds A to F represented by any of formula (I) to (IV).

Further, it is found that an acid to be formed as a by-product of the reaction does not affect the pH and the pH is maintained because the reaction is performed in the buffer solution, and that the reaction advances stably.

The term "buffer solution" means a solution having a large buffer action to change in a concentration of a component in interest in the solution. For example, a mixed solution of a weak acid (AH) such as acetic acid and the conjugate base thereof ($A^-$) can control the change in pH to a minimal level even when a small amount of $H^+$ or $OH^-$ be added. The system containing a weak base (B) and the conjugate acid thereof (BH also shows the same action. Practical pH buffer solutions can be found in a large number of common documents. For example, there is a detailed description in "Rikagaku Jiten, the fifth edition," (1999, Iwanami Shoten, Publishers), edited by Saburou Nagakura.

The acid that can be used in the present invention, preferably in the first embodiment of the present invention, has no particular restriction, and any of organic compounds and inorganic compounds are preferred so long as they have a dissociation exponent pKa in an aqueous solution at 25° C. of 7.0 or less. pKa represents the logarithmic value of the inverse of the acid dissociation constant, and indicates the value determined at an ionic strength of 0.1 at 25° C. The acids with a pKa of 0.0 to 7.0 may be any of inorganic acids such as phosphoric acid, and organic acids such as acetic acid, malonic acid, and citric acid. The acids having a pKa of 0.0 to 7.0 producing effects by the foregoing improvement are organic acids. Further, even for the organic acids, an organic acid having a carboxyl group is most preferred. The organic acids having a pKa of 0.0 to 7.0 may be either monobasic organic acids or polybasic organic acids. For the polybasic organic acids, when the pKa falls within the range of 0.0 to 7.0, the acids can be used in the form of a metal salt (e.g., sodium or potassium salt), or an ammonium salt. Whereas, the organic acids having a pKa of 0.0 to 7.0 can also be used in mixture of two or more thereof.

Preferred specific examples of the organic acid having a pKa 0.0 to 7.0 that can be used in the present invention, preferably in the first embodiment of the present invention, may include various organic acids, including aliphatic-series monobasic organic acids, e.g. formic acid, acetic acid, monochloroacetic acid, monobromoacetic acid, glycolic acid, propionic acid, monochloropropionic acid, lactic acid, pyruvic acid, acrylic acid, butyric acid, isobutyric acid, pivalic acid, aminobutyric acid, valeric acid, and isovaleric acid; amino acid-series compounds, e.g. asparagine, alanine, arginine, ethionine, glycine, glutamine, cysteine, serine, methionine, and leucine; aromatic-series monobasic organic acids, e.g. benzoic acid, and mono-, such as chloro- or hydroxy-, substituted benzoic acid, and nicotinic acid; aliphatic-series dibasic organic acids, e.g. oxalic acid, malonic acid, succinic acid, tartaric acid, malic acid, maleic acid, fumaric acid, oxalacetic acid, glutaric acid, and adipic acid; amino acid-series dibasic organic acids, e.g. aspartic acid, glutamic acid, glutaric acid, cystine, and ascorbic acid; aromatic dibasic organic acids, e.g. phthalic acid, and terephthalic acid; and tribasic organic acids, e.g. citric acid.

The acid that can be preferably used in the present invention, particularly in the first embodiment of the present invention, is a carboxylic acid.

Preferred examples of the carboxylic acid include an aliphatic carboxylic acid, an aromatic carboxylic acid, and a heterocyclic carboxylic acid. The carboxylic acid may be a monocarboxylic acid or a polycarboxylic acid having two ore more carboxyl groups, but is preferably a monocarboxylic acid.

A preferred example of the aliphatic carboxylic acid is a saturated or unsaturated, linear, branched, or cyclic, and substituted or unsubstituted aliphatic carboxylic acid having 1 to 30 carbon atoms (more preferably 1 to 10 carbon atoms). Specific examples thereof include formic acid, oxalic acid, acetic acid, propionic acid, butanoic acid, butyric acid, acrylic acid, and cyclohexanecarboxylic acid. A preferred example of the aromatic carboxylic acid is a substituted or unsubstituted aromatic carboxylic acid having 7 to 30 carbon atoms. Specific examples thereof include benzoic acid, toluic acid, and phthalic acid. A preferred example of the heterocyclic carboxylic acid is a saturated or unsaturated, and substituted or unsubstituted heterocyclic carboxylic acid having 1 to 30 carbon atoms (more preferably 3 to 10 carbon atoms). Specific examples thereof include nicotinic acid, isonicotinic acid, and 1-pyrrolecarboxylic acid.

Of these, the carboxylic acid is preferably an aliphatic carboxylic acid or an aromatic carboxylic acid, more preferably a saturated aliphatic carboxylic acid having 1 to 6 carbon atoms or an aromatic carboxylic acid having 7 to 10 carbon atoms, and furthermore preferably a saturated aliphatic carboxylic acid having 1 to 6 carbon atoms.

In the present invention, particularly in the first embodiment of the present invention, preferred examples of the organic acid include aliphatic-series monobasic organic acids, and most preferred examples thereof include formic acid, acetic acid, and propionic acid.

The compound (acid) with a pKa of 7.0 or less is generally used in an amount of 0.05 to 20 equivalents based on the total amount of the Compounds A to F represented by formula (I), and preferably charged in a 0.1 to 10-fold amount. This provides the effect of inhibiting the decomposition of the compound represented by formula (I). When the acid with a pKa of 7.0 or less is used in a too small amount as compared to the total amount of Compounds A to F represented by formula (I) to be used, the decomposition of the compounds represented by formula (I) is insufficiently inhibited. On the other hand, when the acid with a pKa of 7.0 or less is used in a too much amount to the total amount of the compounds represented by formula (I) to be used, the reaction system shifts to the acid side, so that the reaction becomes less likely to proceed. Whereas, a base is excessively used until a buffer solution occurs, so that a salt of the acid and the base may occur in the form of a crystal, which is not preferable.

With the method of the present invention, particularly of the first embodiment of the present invention, for producing a metal phthalocyanine compound, at least one of Compounds A to F represented by formula (I) is desirably allowed to react with the aforementioned metal compound, in the presence of the aforementioned base and the acid with a pKa of 7.0 or less.

As the reaction conditions in this case, the reaction temperature is generally 30 to 220° C., preferably 40 to 200° C., and further preferably 50 to 180° C. When the reaction temperature is too low, the reaction rate conspicuously decreases, uneconomically resulting in a marked increase in length of period of time required for the synthesis. Whereas, when the production is carried out at a too high temperature, the amount of by-products unfavorably increases.

As the metal compound to be added for the reaction of the present invention, particularly in the first embodiment of the present invention, in addition to a metal, a metal oxide, or a metal hydroxide, use can be made of a metal chloride, a metal acetate, or, as a complex, a metal aquo complex or ammine complex. As metals or metal oxides capable of being introduced, mention may be made of VO, TiO, Mn, Fe, Co, Ni, Cu, Zn, Pd, Cd, Mg, and the like. Out of these, Fe, Ni, Cu, and Zn are preferred, and Ni, Cu, and Zn are further more preferred. Whereas, the salt is in particular preferably in the form of chloride (e.g. copper chloride), acetate, aquo complex, with the chloride and acetate being most preferred. The amount of it to be used is preferably 0.01- to 10-fold equivalents, more preferably 0.05- to 5-fold equivalents, and particularly preferably 0.1- to 3-fold equivalents, based on the total amount of Compounds A to F represented by formula (I).

Further, in the present invention, particularly in the first embodiment of the present invention, a catalyst may be used simultaneously. As the catalysts that can be used in the present invention, particularly in the first embodiment of the present invention, any of the catalysts which are commonly used in the production of a metal phthalocyanine compound, may be used. Examples thereof may include molybdenum compounds, e.g. ammonium molybdate, molybdic acid, ammonium phosphomolybdate, and molybdenum oxide; tungsten compounds, e.g. ammonium tungstate, and ammonium phosphotungstate; arsenic-vanadium compounds; boric acid; or halides or oxyhalides of titanium, tin or antimony. Out of these, ammonium molybdate is excellent.

As the solvent that can be used in the method of the present invention, preferably of the first embodiment of the present invention, any of the common organic solvents may be used. Out of these, organic solvents having a hydroxyl group, and polar solvents (e.g., acetonitrile, formamide, N,N-dimethylformamide, N,N-dimethylacetamide, dimethylsulfoxide, sulfolane, propylenecarbonate, N-methyl-2-pyrrolidone, N-vinyl-2-pyrrolidone, and N,N-diethyldodecanamide) are preferred. More preferred examples of alcohol may include methanol, ethanol, pentanol, heptanol, octanol, cyclohexanol, benzyl alcohol, phenethyl alcohol, phenylpropyl alcohol, furfuryl alcohol, and anise alcohol.

Further, not only mono- but also oligo- (particularly, di- and tri-), and poly-$C_2$ to $C_4$-alkylene glycols (in brief, "glycols"), and mono-$C_1$ to $C_8$-alkyl- and monoaryl ethers thereof (in brief, "glycol monoether") are also preferred. Further, ethylene-based compounds are also advantageous. Examples thereof may include ethylene glycol, 1,2- or 1,3-propylene glycol, diethylene glycol, butylene glycol, di-, tri-, or tetraethylene glycol, di-, tri-, or tetra-propylene glycol, polyethylene- or polypropylene glycol, ethylene glycol monomethyl-, -monoethyl-, -monopropyl-, -monobutyl- or -monohexyl ether, propylene glycol monomethyl-, -monoethyl-, -monopropyl-, -monobutyl- or -monohexyl ether, di-, tri-, or tetra-ethylene glycol monomethyl-, -monoethyl- or -monobutyl ether, di-, tri-, or tetra-propylene glycol monomethyl-, -monoethyl- or -monobutyl ether, or ethylene- or propylene glycol monophenyl ether. Further, in the present invention, particularly in the first embodiment of the present invention, an industrially applicable inactive solvent may also be used. Examples thereof may include nitrobenzene, trichlorobenzene, chloronaphthalene, methylnaphthalene, naphthalene, alkylbenzene, paraffin, naphthene, and kerosine.

These may be used alone, or in an appropriate mixture of two or more thereof so long as the mixture is a combination of the solvents not affecting one another. The amount of the solvents to be used is generally 1 to 100 times by mass, preferably 1 to 20 times by mass, and further preferably 1 to 5 times by mass, based on the total amount to be used of the Compounds A to F represented by formula (I).

Further, a more preferred solvent in the method of the present invention, particularly in the first embodiment of the present invention, is at least one selected from glycerin and compounds represented by formula (V), and the solvent may contain the polar solvent or organic solvent having a hydroxyl group described in the above section mixed appropriately in a combination providing no effect on each other. In formula (V), s and t each independently represent a positive integer, and s and t each independently represent preferably an integer of 1 to 10, and more preferably an integer of 1 to 5. X represents a hydrogen atom or a methyl group. More preferred examples of the solvent include: ethylene glycol; diethylene glycol; triethylene glycol; polypropylene glycol; propylene glycol; dipropylene glycol; a 1:2 (v/v) mixed solvent of ethylene glycol and diethylene glycol; a 3:1 (v/v) mixed solvent of propylene glycol and triethylene glycol; and a 1:5 (v/v) mixed solvent of methanol and triethylene glycol. The amount of the solvent to be used is generally 1 to 100 times by mass, preferably 1 to 20 times by mass, and more preferably 1 to 5 times by mass of the total amounts to be used of Compounds A to F represented by formula (I).

For this reaction, the execution of the reaction for a long time entails a concern about the stability of the objective product and the occurrence of the side reaction, and is uneconomical. The reaction time is preferably less than 10 hours, further preferably less than 5 hours, and still further preferably less than 4 hours.

In summary, the method for producing the metal phthalocyanine compound, according to the present invention, preferably to the first embodiment of the present invention, is preferably a production method including the combination of the following (a5) to (h7).

(a5) The acid that can be used in the present invention has no particular restriction, but any of organic compounds and inorganic compounds are preferred so long as they have a dissociation exponent pKa of 7.0 or less for the acid or conjugate acid in an aqueous solution at 25° C. Out of these, an organic acid that is an acid of pKa 0.0 to 7.0 is preferred, and an organic acid having a carboxyl group is most preferred. Out of the organic acids, aliphatic-series monobasic organic acids are preferred, and formic acid, acetic acid, and propionic acid are most preferred.

(b5) As the base, an organic base or inorganic base including an alkali metal may be used. As the inorganic base, for example, an inorganic base, e.g. lithium carbonate, sodium carbonate, potassium carbonate, sodium hydrogencarbonate, lithium hydroxide, and potassium hydroxide, may be used. The carboxylate or organic base is preferably at least one compound selected from the compounds represented by formula (IV), and particularly preferred examples thereof include ethanolamine, diethanolamine, and triethanolamine. Other examples of the organic base include lithium acetate, potassium acetate, sodium oxalate, and disodium ethylenediaminetetraacetate.

In the present invention, any of the organic base and the inorganic base may be used alone, or they may be used in combination. Since the base is dissolved in a reaction solvent to serve as a buffer solution, a base having high solubility is preferred. An ammonium salt of a carboxylic acid as an inorganic base, and an organic base are more preferred, and an organic salt containing an ammonium ion or an alkali metal ion as a cation is particularly preferred.

Out of the ammonium salts of carboxylic acids, an aliphatic ammonium salt and an aromatic ammonium salt are particularly preferable, and an aromatic ammonium salt is most preferable. Out of them, ammonium benzoate is most preferable.

(c5) As for the reaction conditions, the reaction temperature is generally 30 to 220° C., preferably 40 to 200° C., and particularly preferably 50 to 180° C.

(d5) As a metal or metal oxide capable of being introduced, use may be made of VO, TiO, Mn, Fe, Co, Ni, Cu, Zn, Pd, Cd, Mg, and the like. Out of these, Ni, Cu, and Zn are preferred. Further, the salt is particularly preferably in the form of chloride (e.g. copper chloride) or acetate. The amount of it to be used is particularly preferably 0.1- to 3-fold equivalents, to the total amount to be used of Compounds A to F represented by formula (I).

(e5) Examples of the most preferable solvent include: ethylene glycol; diethylene glycol; triethylene glycol; polypropylene glycol; propylene glycol; dipropylene glycol; a 1:2 (v/v) mixed solvent of ethylene glycol and diethylene glycol; and a 4:1 (v/v) mixed solvent of propylene glycol and triethylene glycol. A particularly preferable amount to be used is 1 to 5 times by mass, to the total amount to be used of Compounds A to F represented by formula (I).

(f5) The reaction time is particularly preferably less than 4 hours.

(g5) Of Compounds A to F represented by formula (I) according to the present invention, Compounds G to L represented by formula (II) are preferred. Compounds M to R represented by formula (III) are more preferred, and Compounds S to X represented by formula (IV) are furthermore preferred. Of those, Compounds S and W are particularly preferred, and Compound S is most preferred.

(h5) In formulas (III) and (IV), $a_1$ preferably represents a sulfinyl group, a sulfonyl group, a sulfamoyl group, an acyl group, or a carbamoyl group, particularly preferably a sulfonyl group, a sulfamoyl group, or a carbamoyl group, and most preferably a sulfonyl group. $m_1$ is preferably 1 or 2, and most preferably 1.

The combination satisfies preferably at least one condition described above, more preferably a larger number of conditions described above, and most preferably all conditions described above.

Next, specific examples (1) to (54) of the compound represented by formulas (I) to (IV) that can be used in the present invention will be shown below, but the present invention is not limited to these.

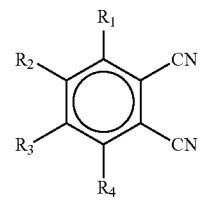

| Compound No. | $R_1$ | $R_2$ | $R_3$ | $R_4$ |
|---|---|---|---|---|
| 1 | $-SO_2(CH_2)_3SO_3Na$ | $-H$ | $-H$ | $-H$ |
| 2 | $-H$ | $-SO_2(CH_2)_3SO_3Li$ | $-H$ | $-H$ |
| 3 | $-H$ | $-SO_2(CH_2)_3SO_3Li$ | $-Cl$ | $-H$ |
| 4 | $-H$ | $-SO_2(CH_2)_3SO_3Li$ | $-SO_2(CH_2)_3SO_3Li$ | $-H$ |
| 5 | $-H$ | $-SO_2(CH_2)_3SO_2NHCH_2CH(OH)CH_3$ | $-H$ | $-H$ |
| 6 | $-H$ | $-SO_2(CH_2)_3SO_2NHCH_2CH(OH)CH_2SO_3Li$ | $-H$ | $-H$ |
| 7 | $-H$ | $-SO_2(CH_2)_3SO_2NHCH_2CH(OH)CH_2CO_2Na$ | $-H$ | $-H$ |
| 8 | $-H$ | $-SO_2(CH_2)_3CO_2Na$ | $-H$ | $-H$ |
| 9 | $-H$ | $-SO_2(CH_2)_3SO_2NH(CH_2)_3OCH(CH_3)_2$ | $-H$ | $-H$ |
| 10 | $-H$ | $-SO_2(CH_2)_3CO_2CH(CH_3)CH_2OCH_3$ | $-H$ | $-H$ |
| 11 | $-H$ | $-SO_2(CH_2)_3SO_3NH(CH_2)_3N(CH_3)_2$ | $-H$ | $-H$ |
| 12 | $-H$ | $-SO_2(CH_2)_4SO_3Li$ | $-H$ | $-H$ |
| 13 | $-H$ | $-SO_2(CH_2)_2CH(CH_3)SO_3K$ | $-H$ | $-H$ |
| 14 | $-H$ | $-SO_2(CH_2CH_2O)_2CH_2CH_2SO_3Li$ | $-H$ | $-H$ |
| 15 | $-H$ | $-SO_2(CH_2)_2NHSO_2-\langle\text{phenyl}\rangle-SO_3Li$ | $-H$ | $-H$ |
| 16 | $-SO_2NH(CH_2)_2SO_3Li$ | $-H$ | $-H$ | $-H$ |
| 17 | $-H$ | $-SO_2NH(CH_2)_2SO_3Li$ | $-H$ | $-H$ |
| 18 | $-H$ | $-CO_2NH(CH_2)_3SO_3Li$ | $-H$ | $-H$ |
| 19 | $-H$ | $-SO(CH_2)SO_3K$ | $-H$ | $-H$ |
| 20 | $-H$ | $-SO(CH_2)SO_3Li$ | $-SO_2(CH_2)_3SO_3Li$ | $-H$ |

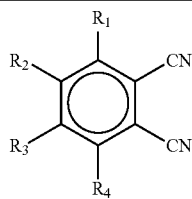

| Compound No. | R₁ | R₂ | R₃ | R₄ |
|---|---|---|---|---|
| 21 | —H | —SO$_2$NH$_2$ | —H | —H |
| 22 | —COPh | —H | —H | —H |
| 23 | —H | —S—(CH$_2$)SO$_3$Li | —H | —H |
| 24 | —O—C$_2$H$_5$ | —H | —H | —H |
| 25 | —S—C$_4$H$_9$(n) | —H | —H | —H |
| 26 | —SOC$_4$H$_9$(n) | —H | —H | —H |
| 27 | —SO$_2$C$_4$H$_9$(n) | —H | —H | —H |
| 28 | —SO$_2$(CH$_2$)$_3$SO$_2$NH$_2$ | —H | —H | —H |
| 29 | —O—C$_2$H$_5$ | —H | —H | —O—C$_2$H$_5$ |
| 30 | —S—C$_4$H$_9$(n) | —H | —H | —S—C$_4$H$_9$(n) |
| 31 | —S(CH$_2$)SO$_3$Na | —H | —H | —H |
| 32 | —SO$_2$NHPh | —H | —H | —H |
| 33 | —HNSO$_2$Ph | —H | —H | —H |
| 34 | —S—Ph | —H | —H | —H |
| 35 | —H | —NHSO$_2$C$_8$H$_{17}$(n) | —H | —H |
| 36 | —H | —NHCOCH(CH$_3$)$_2$ | —H | —H |
| 37 | —H | —O—C$_4$H$_9$(n) | —O—C$_4$H$_9$(n) | —H |
| 38 | —H | —SO$_3$Li | —H | —H |
| 39 | —H | —SO$_2$(CH$_2$)$_3$SO$_2$NLiSO$_2$Ph | —H | —H |
| 40 | —H | —SO$_2$(CH$_2$)$_3$SO$_2$NH—C$_6$H$_4$-SO$_3$Li | —H | —H |

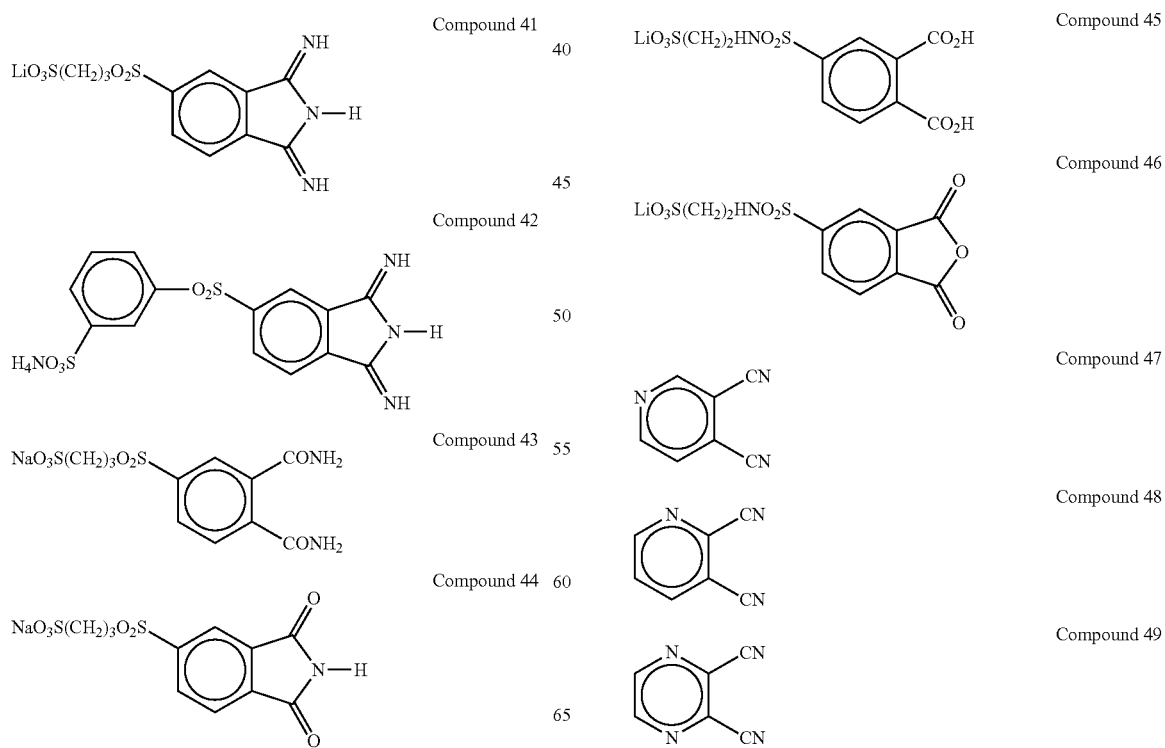

-continued

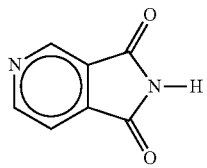

Compound 50

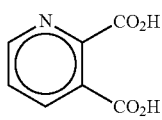

Compound 51

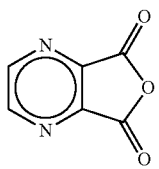

Compound 52

Hereinafter, the metal phthalocyanine compound that can be produced through the production method of the present invention, particularly of the first embodiment of the present invention, will be described.

The metal phthalocyanine compound to be produced through the production method of the present invention, particularly of the first embodiment of the present invention, is represented by formula (VII).

Formula (VII)

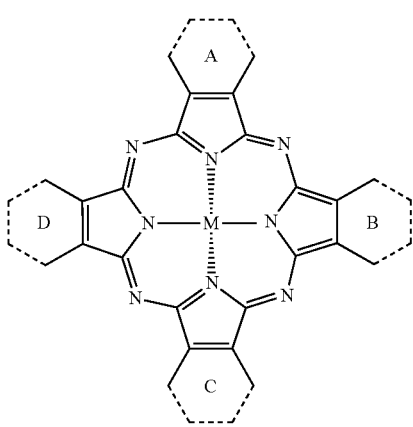

In formula (VII), the rings A, B, C, and D each have the same meaning as G as described for formula (I), and preferable examples of those are also similar to those described for formula (I).

M represents a metal atom. When M represents a metal atom, any metal can be used as long as the metal may form a stable complex, and examples of the metal include Li, Na, K, Mg, Ti, Zr, V, Nb, Ta, Cr, Mo, W, Mn, Fe, Co, Ni, Ru, Rh, Pd, Os, Ir, Pt, Cu, Ag, Au, Zn, Cd, Hg, Al, Ga, In, Si, Ge, Sn, Pb, Sb, and Bi. In addition, the metal atom may form a complex with a phthalocyanine compound in a state where the metal atom is an oxide, a hydroxide, or a halide. Examples of the oxide include VO and GeO. Examples of the hydroxide include $Si(OH)_2$, $Cr(OH)_2$, or $Sn(OH)_2$. Examples of the halide include AlCl, $SiCl_2$, VCl, $VCl_2$, VOCl, FeCl, GaCl, or ZrCl. Mg, Ca, Co, Zn, Pd, or Cu is preferably used as the metal atom. Co, Pd, Zn, or Cu is more preferably used. Cu is particularly preferably used.

Specific examples of the phthalocyanine compound to be produced by the method of the present invention, particularly of the first embodiment of the present invention, are shown below, but the present invention is not limited thereto. The following examples each correspond to the case where M represents Cu.

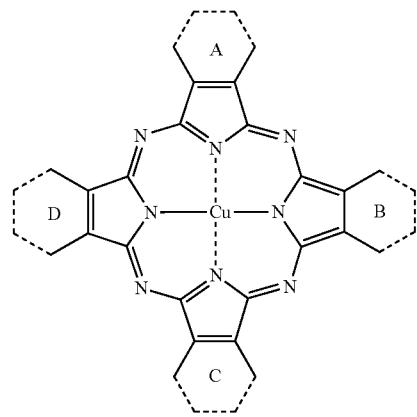

One of the rings A to D is

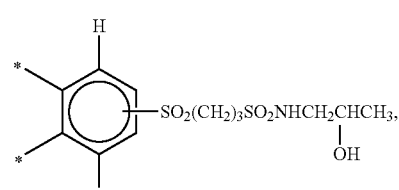

and the other three rings are

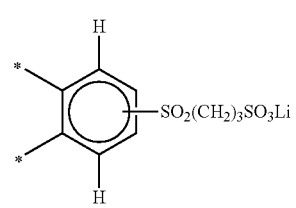

"*" represents the binding site to the phthalocyanine ring.

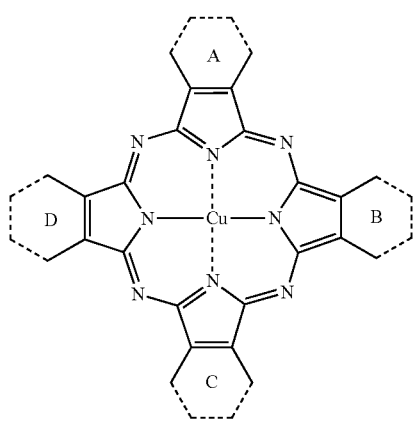

One of the rings A to D is

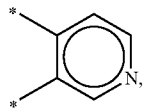

and
the other three rings are

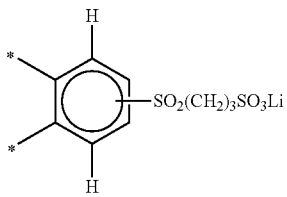

"*" represents the binding site to the phthalocyanine ring.

In production of the phthalocyanine compound according to the present invention, particularly to the first embodiment of the present invention, in the case where theoretically required four molecules of the compounds represented by formula (I) are used such that they would have two different Rs (R1+R2=4) in a ratio of R1:R2=3:1 (eq/eq), the reaction advances according to, for example, the following scheme.

Asymmetric reaction scheme (Exemplified example: $R_1$=3, $R_2$=1:Compound A)

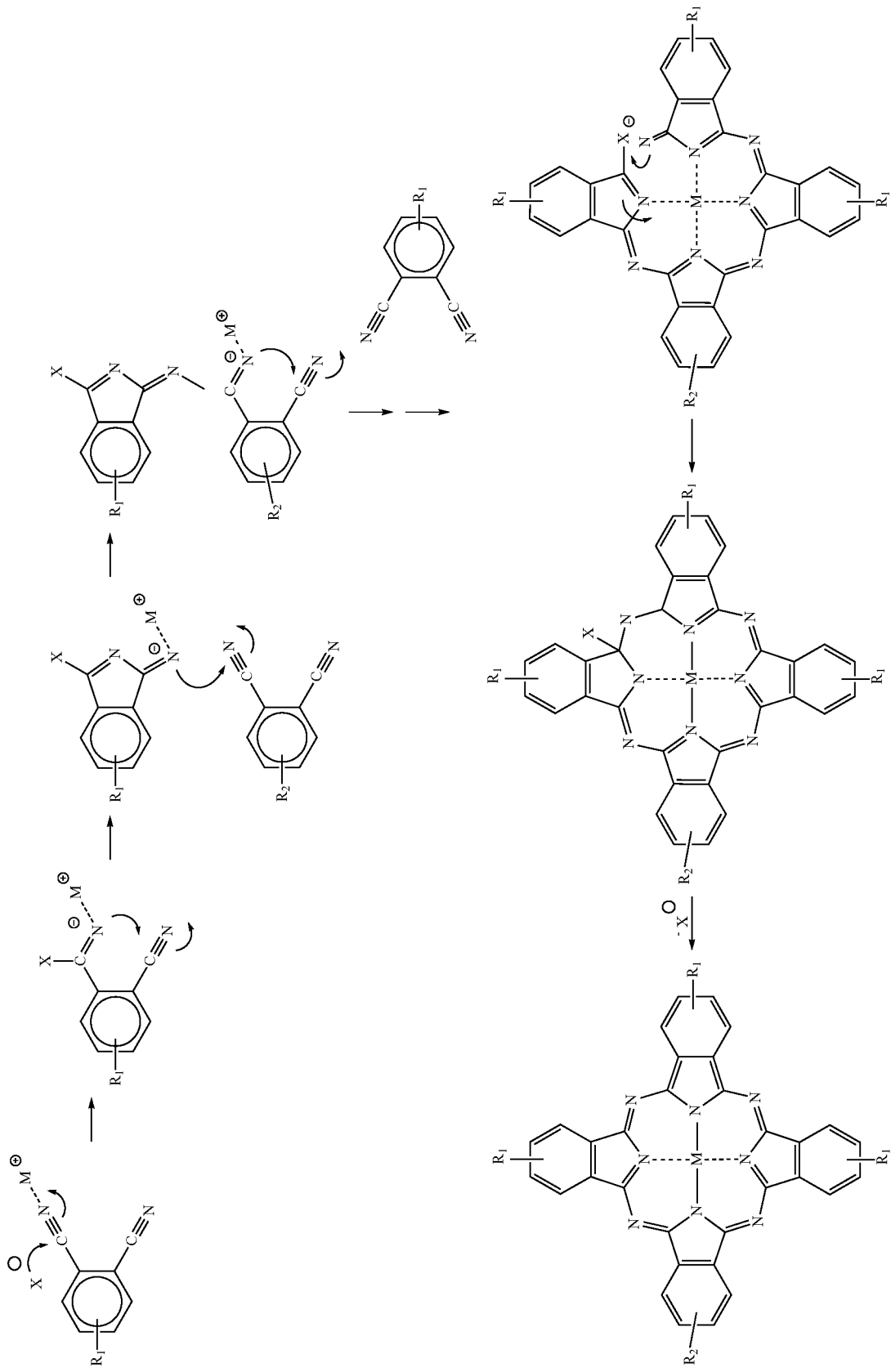

Further, production of the metal phthalocyanine compound by using Compound B, C, D, E, or F may be performed by combining methods described in or referred to, for example, in "Kinoseishikiso toshiteno Phthalocyanine (Kiso-hen, Oyo-hen)", edited by Ryo Hirohashi, Keiichi Sakamoto, and Eiko Okumura, published by Industrial Publishing & Consulting, Inc. (2004), p. 30-33, "Phthalocyanines-Properties and Applications", written by C. C. Leznoff and A. B. P. Lever, published by VCH, p. 1-54, or the like, or by combining methods similar thereto.

Next, the compound represented by formula (11) or (12) is described.

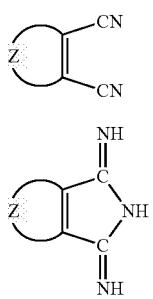

Formula (11)

Formula (12)

In formulae (11) and (12), Z represents an organic moiety for forming a 6-membered aromatic ring structure together with the two carbon atoms bonded to the Z. This aromatic structure may have a single ring structure or a condensed ring structure with a ring fused thereto. The 6-membered aromatic ring structure formed by Z may have: an alicyclic structure, e.g. a benzene ring or a naphthalene ring; or a nitrogen-containing aromatic hetero ring structure, e.g. a pyridine ring, a pyrazine ring, a pyridazine ring, a pyrimidine ring, a triazine ring, a quinoline ring, or a phthalazine ring. A pyrrole-2,5-diylidenediamine compound represented by formula (12) may be in the form represented by formula (12) or may be used in the form of its tautomer. Preferred examples of the 6-membered aromatic ring formed by Z include a benzene ring, a naphthalene ring, a pyridine ring, and a pyridazine ring. More preferred examples thereof include a benzene ring, a naphthalene ring, and a pyridine ring, and a particularly preferred example thereof is a benzene ring. The aromatic structure may have a substituent. The substituent may be a group selected from groups that a compound represented by formula (15) described below may have thereon.

Of the compounds represented by formulae (11) and (12), the compound represented by formula (II) is preferred.

A preferred example of the compound represented by formula (11) may be represented by formula (15).

Hereinafter, a phthalonitrile compound represented by formula (15) will be described.

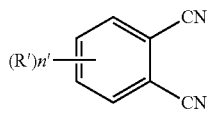

Formula (15)

In formula (15), R' represents a hydrogen atom or a substituent, and the specific examples and preferable examples thereof are the same as those for R in formula (I).

The substituent represented by R' may be further substituted. Such a substituent further substituted may include a substituent substituted by any group, and is preferably a substituent substituted by an ionic hydrophilic group. Specifically, preferable examples thereof include those substituted by a hydrophilic group, e.g. a carboxyl group, a sulfo group, a phosphoric acid group, a group having a quaternary salt structure of nitrogen, or a group having a quaternary salt structure of phosphorus. In the case where the substituent has a carboxyl group, a sulfo group, or a phosphoric acid group as a hydrophilic group, the hydrophilic group may have a counter cation as required. Examples of the counter cation that may be used include a metal ion, a group having a quaternary salt structure of nitrogen, and a group having a quaternary salt structure of phosphorus. In the case where the substituent has a group having a quaternary salt structure of nitrogen, or a group having a quaternary salt structure of phosphorus as a hydrophilic group, the hydrophilic group may have a counter anion as required. Examples of the counter anion include a halogen ion, a sulfate ion, a nitrate ion, a phosphate ion, an oxalate ion, an alkanesulfonate ion, an arylsulfonate ion, an alkanecarboxylate ion, and an arylcarboxylate ion.

Preferred examples of the hydrophilic group include a carboxyl group, a sulfo group, and a phosphoric acid group, and more preferred examples thereof include a carboxyl group and a sulfo group. In this case, preferred examples of the counter cation that can be used include cations of Li, Na, K, Mg, and Ca. More preferred examples thereof include cations of Li, Na, and K, and particularly preferred examples thereof are cations of Li and Na.

In the case where R' represents a group having a carbon atom(s), the total number of carbon atom(s) is preferably 1 to 100, more preferably 1 to 80, furthermore preferably 1 to 50, and particularly preferably 1 to 20.

n' represents an integer of 1 to 4, preferably an integer of 1 to 3, and more preferably an integer of 1 or 2. In the case where n' is 2 to 4, a plurality of R's exist, and the plurality of R's may be the same or different from each other or may be bonded to each other to form a ring. The plurality of R's are preferably not bonded to together.

In synthesis of a phthalocyanine compound from a phthalonitrile compound, four molecules of the phthalonitrile compound are required for synthesis of one molecule of the phthalocyanine compound. Herein, the required four molecules of the phthalonitrile compound represented by formula (15) need not be the same each other, and a plurality of phthalonitriles having different R's may be used in an arbitrary ratio. In the present invention, particularly in the second embodiment of the present invention, the four molecules of the phthalonitrile compound are preferably the same.

A substitution position of R' in the phthalonitrile compound represented by formula (15) may be at any position as long as the substitution is possible, but the substitution position is preferably at a 3- or 6-position, which is at an ortho-position to the cyano group(s), or at a 4- or 5-position.

Examples of the phthalonitrile compound represented by formula (15) that can be used in the present invention, particularly in the second embodiment of the present invention, are shown below, but the present invention is not limited to those.

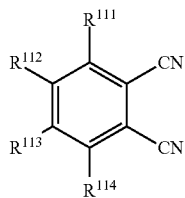

| Compound | R¹¹¹ | R¹¹² | R¹¹³ | R¹¹⁴ |
|---|---|---|---|---|
| 101 | —OEt | H | H | H |
| 102 | —S—ⁿBu | H | H | H |
| 103 | —SO—ⁿBu | H | H | H |
| 104 | —SO₂—ⁿBu | H | H | H |
| 105 | —SO₂—(CH₂)₃—SO₃Na | H | H | H |
| 106 | —SO₂—(CH₂)₃—SO₃Li | H | H | H |
| 107 | —SO₂—(CH₂)₃—SO₂NH₂ | H | H | H |
| 108 | —S—Ph | H | H | H |
| 109 | —SO₂—Ph | H | H | H |
| 110 | —SO₂—(CH₂)₃—CO₂Et | H | H | H |
| 111 | —SO₂—(CH₂)₄—SO₃Na | H | H | H |
| 112 | —SO₂—(CH₂)₂—SO₃Na | H | H | H |
| 113 | —SO₂—(CH₂)₅—SO₃Li | H | H | H |
| 114 | —SO₂—CH₂CH₂—O—CH₂CH₂—SO₃Na | H | H | H |
| 115 | —SO₂—CH₂CH₂—(O—CH₂CH₂)₂—SO₃Na | H | H | H |
| 116 | —SO₂—CH₂CH₂—(O—CH₂CH₂)₃—SO₃Na | H | H | H |
| 117 | —SO₂—CH₂CH₂—(O—CH₂CH₂)₄—SO₃Na | H | H | H |
| 118 | —SO₂—CH₂CH₂—(O—CH₂CH₂)₅—SO₃Na | H | H | H |
| 119 | H | —OEt | H | H |
| 120 | H | —S—ⁿBu | H | H |
| 121 | H | —CONH₂ | H | H |
| 122 | H | —SO₂NHPh | H | H |
| 123 | H | —SO₂—(CH₂)₃—SO₃Li | H | H |
| 124 | H | —SO₂—(CH₂)₃—SO₂NH₂ | H | H |
| 125 | H | —S—C₆H₄—CO₂Et | H | H |
| 126 | H | —S-(3-Py) | H | H |
| 127 | H | —SO₂—(CH₂CH₂O)₄—H | H | H |
| 128 | H | —SO₂—(CH₂)₄—SO₃Na | H | H |
| 129 | —OEt | H | H | —OEt |
| 130 | —S—ⁿBu | H | H | —S—ⁿBu |
| 131 | —SO₂NHPh | H | H | H |
| 132 | —S—(CH₂)₃—SO₃Na | H | H | H |
| 133 | —SO₂—(CH₂)₃—SO₃K | H | H | H |
| 134 | —O—ⁱPr | H | H | —O—ⁱPr |
| 135 | H | —O—ⁿBu | —O—ⁿBu | H |
| 136 | H | —S—ⁿHex | Cl | H |
| 137 | H | —O—(CH₂CH₂O)₅—H | —O—(CH₂CH₂O)₅—H | H |
| 138 | —CO—Ph | H | H | H |
| 139 | —SO₂—Bu⁻ˢ | H | H | H |
| 140 | —S—C₆H₄—C(O)N(CH₂CH₂OC₂H₅)₂ | H | H | H |
| 141 | —S—C₆H₄—C(O)N(CH₂CH₂OCH₃)₂ | H | H | H |
| 142 | —S—C₆H₄—C(O)N(CH₂CH₂OC₂H₅)(CH(CH₃)COOH) | H | H | H |
| 143 | —S—C₆H₄—C(O)N(CH₂CH₂OC₂H₄OC₂H₅)(CH₂CH₂COOH) | H | H | H |

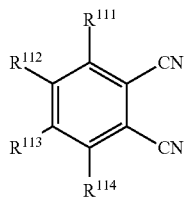

| Compound | $R^{111}$ | $R^{112}$ | $R^{113}$ | $R^{114}$ |
|---|---|---|---|---|
| 144 | —S—C₆H₄—C(=O)—N(CH₂CH₂OC₂H₄OC₂H₅)(CH₂CH₂CH₂SO₃Na) [with CN substituent on the phenyl ring] | H | H | H |
| 145 | —S—C₆H₄—CO₂Et | H | H | H |

Herein, in the table and description, Et represents ethyl; Bu represents butyl; Hex represents hexyl; Ph represents phenyl; Pr represents propyl; and Py represents pyridyl.

Next, the compound represented by formula (13) or (14) will be described.

The phthalocyanine compound and phthalocyanine analogue, as represented by formula (13) or (14), according to the present invention, particularly to the second embodiment of the present invention, will be described.

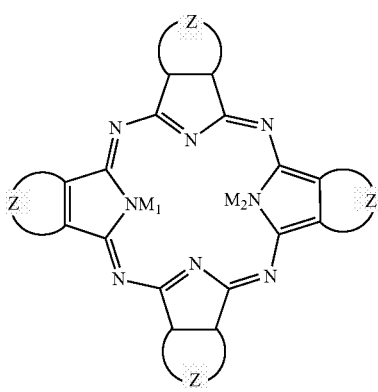

Formula (13)

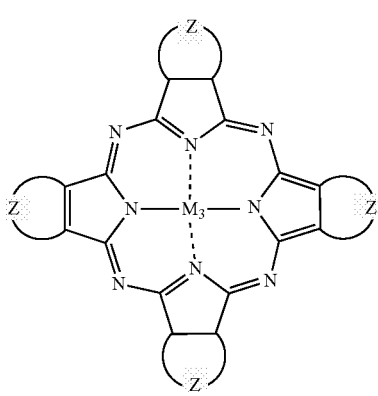

Formula (14)

In formulae (13) and (14), Z has the same meaning as defined in formulae (II) and (12); $M_1$ and $M_2$ each independently represent an atom in the Group 1 of the periodic table; and $M_3$ represents a metal atom or a metal compound thereof, except an atom in the Group 1 of the periodic table.

Z has the same preferable range as that of Z in each of formulae (11) and (12).

The four aromatic rings each formed by Z may be the same or different from each other. Aromatic rings having the same aromatic ring skeleton may have the same substituent(s) or different substituent(s). Further, even the substituent(s) is/are the same as each other in the respective aromatic rings, the substituent(s) may substitute on different substitution position(s) in the respective aromatic rings.

Further, the phthalocyanine compound or analogue may be a mixture of the above-mentioned compounds, or a mixture of structural isomers thereof.

$M_1$ and $M_2$ each preferably represent H, Li, Na, or K. $M_3$ preferably represents a metal atom in Periods 3 to 6 of Groups 2 to 15 of the periodic table, or a metal atom in lanthanide series.

Examples of $M_3$ include Mg, Ti, Zr, V, Nb, Ta, Cr, Mo, W, Mn, Fe, Co, Ni, Ru, Rh, Pd, Os, Ir, Pt, Cu, Ag, Au, Zn, Cd, Hg, Al, Ga, In, Si, Ge, Sn, Pb, Sb, and Bi. Of these, preferred are Mg, Ca, Co, Zn, Pd, and Cu, more preferred are Co, Pd, Zn, and Cu, and particularly preferred is Cu. The metal atom may be a metal compound. Examples thereof include a metal oxide, a metal hydroxide, and a metal halide, and the metal compound may be in the form of a complex with the phthalocyanine compound. Examples of the oxide include VO and GeO. Examples of the hydroxide include $Si(OH)_2$, $Cr(OH)_2$, and $Sn(OH)_2$. Examples of the halide include AlCl, $SiCl_2$, VCl, $VCl_2$, VOCl, FeCl, GaCl, and ZrCl. In the present invention, particularly in the second embodiment of the present invention, the metal atom is preferable.

Preferred examples of the compound represented by formula (13) or (14) are represented by formula (13A) or (14A), respectively.

Formula (13A)

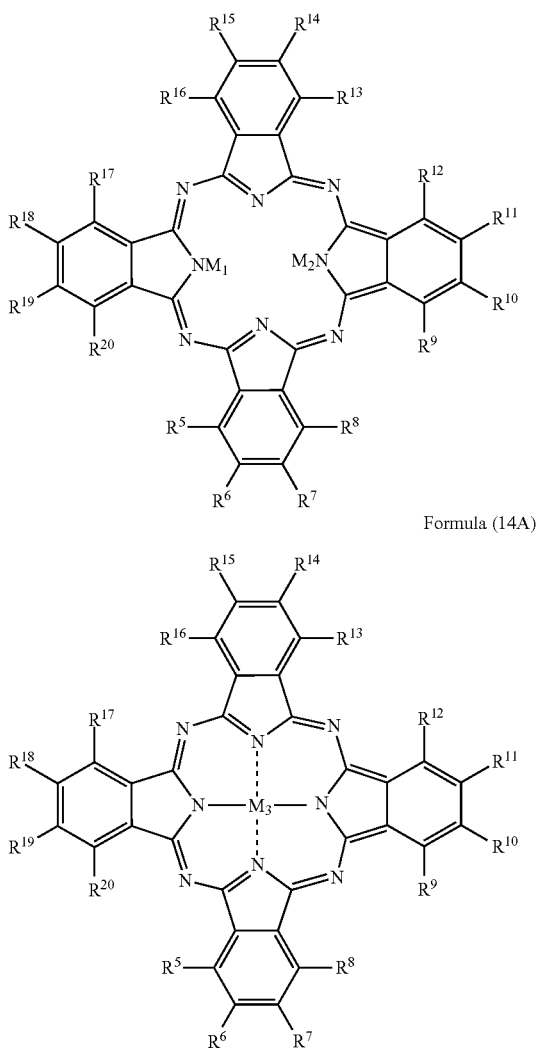

Formula (14A)

In formulae (13A) and (14A), $M_1$ to $M_3$ have the same meanings as formulae (13) and (14), and preferred ranges thereof are also the same as those described for formulae (13) and (14).

$R^5$ to $R^{20}$ each independently represent a hydrogen atom or a substituent. The substituent is a group selected from the same range of group for R' in formula (15), and preferred examples thereof are also the same as those described for formula (15).

Further, in the case where $R^5$ to $R^{20}$ are each substituted by a hydrophilic group as a substituent, e.g. a carboxyl group, a sulfo group, a phosphoric acid group, a group having a quaternary salt structure of nitrogen, or a group having a quaternary salt structure of phosphorus, a counter cation(s) thereof may be the same or different from a corresponding counter cation(s) of the phthalonitrile compound represented by formula (15), which is a precursor of the phthalocyanine compound. In the case where $R^5$ to $R^{20}$ are each substituted by a substituent, e.g. a group having a quaternary nitrogen or phosphorus salt structure, a counter anion(s) thereof may be the same or different from a corresponding counter anion(s) of the phthalonitrile compound represented by formula (15), which is a precursor of the phthalocyanine compound. In each case of the above, when the counter ion(s) differs from that of the phthalonitrile compound represented by formula (15), an appropriate ion-exchange method may be employed during a phthalocyanine compound synthesis reaction or post-treatment thereof, to thereby allow synthesis of a phthalocyanine compound having a target counter ion(s).

As described above, the phthalocyanine compound to be produced through the present invention, particularly through the second embodiment of the present invention, also includes a mixture (mixture containing structural isomers) of compounds having R's of four benzene rings of phthalocyanine at different substitution positions.

Hereinafter, examples of a phthalocyanine derivative that can be synthesized through the present invention, particularly through the second embodiment of the present invention, are shown, but the present invention is not limited to the examples. In the following examples of the compound, a mixture of stereoisomers is depicted as one compound.

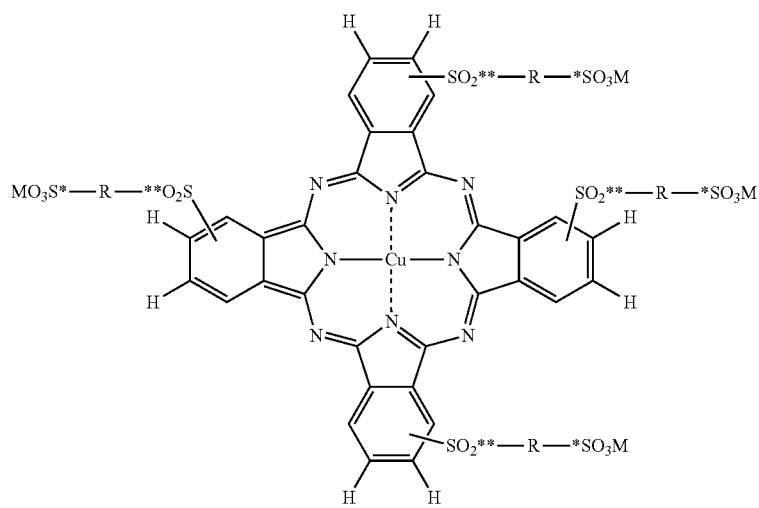

-continued

| **—R—* = | | M = Li | M = Na | M = K |
|---|---|---|---|---|
| **—CH$_2$CH$_2$—* | | 201 | 210 | 219 |
| **—CH$_2$CH$_2$CH$_2$—* | | 202 | 211 | 220 |
| **—CH$_2$CH$_2$CH$_2$CH$_2$—* | | 203 | 212 | 221 |
| **—CH$_2$CH$_2$CH$_2$CH$_2$CH$_2$—* | | 204 | 213 | 222 |
| **—CH$_2$CH$_2$—(OCH$_2$CH$_2$)$n$—* | | | | |
| n = 1 | | 205 | 214 | 223 |
| 2 | | 206 | 215 | 224 |
| 3 | | 207 | 216 | 225 |
| 4 | | 208 | 217 | 226 |
| 5 | | 209 | 218 | 227 |
| **—C$_6$H$_4$—* (para) | | 228 | 231 | |
| **—C$_6$H$_4$—* (meta) | | 229 | 232 | |
| **—C$_6$H$_4$—* (ortho) | | 230 | 233 | |
| **—C$_6$H$_4$—CONHCH$_2$CH$_2$—* (para) | | 234 | 237 | |
| **—C$_6$H$_4$—CONHCH$_2$CH$_2$OCH$_2$CH$_2$—* (meta) | | 235 | 238 | |
| **—C$_6$H$_4$—CONHCH$_2$CH$_2$—* (ortho) | | 236 | 239 | |

[Structure: Cu phthalocyanine tetrasulfonamide with four SO$_2$**—R—*SO$_3$M substituents]

| **—R—* = **—CH$_2$CH$_2$—* | 240 | M = Li & NH$_4$ (Li/NH$_4$ = 3/1) |
|---|---|---|
| | 241 | M = Li & NH$_4$ (Li/NH$_4$ = 2/2) |
| | 242 | M = Na & NH$_4$ (Na/NH$_4$ = 3/1) |
| | 243 | M = Na & NH$_4$ (Na/NH$_4$ = 2/2) |
| | 244 | M = Na & NH$_4$ (Na/NH$_4$ = 1/3) |

-continued

| | | |
|---|---|---|
| **—CH$_2$CH$_2$CH$_2$—* | 245 | M = Li & NH$_4$ (Li/NH$_4$ = 3/1) |
| | 246 | M = Li & NH$_4$ (Li/NH$_4$ = 2/2) |
| | 247 | M = Li & NH$_4$ (Li/NH$_4$ = 1/3) |
| | 248 | M = Na & NH$_4$ (Na/NH$_4$ = 3/1) |
| | 249 | M = Na & NH$_4$ (Na/NH$_4$ = 2/2) |
| | 250 | M = Na & NH$_4$ (Na/NH$_4$ = 1/3) |
| | 251 | M = K & NH$_4$ (K/NH$_4$ = 3/1) |
| | 252 | M = K & NH$_4$ (K/NH$_4$ = 2/2) |
| | 253 | M = K & NH$_4$ (K/NH$_4$ = 1/3) |
| | 254 | M = Et$_4$N |
| **—CH$_2$CH$_2$CH$_2$CH$_2$—* | 255 | M = Li & NH$_4$ (Li/NH$_4$ = 3/1) |
| | 256 | M = Li & NH$_4$ (Li/NR$_4$ = 2/2) |
| | 257 | M = Na & NH$_4$ (Na/NH$_4$ = 3/1) |
| | 258 | M = Na & NH$_4$ (Na/NH$_4$ = 2/2) |
| | 259 | M = Na & NH$_4$ (Na/NH$_4$ = 1/3) |

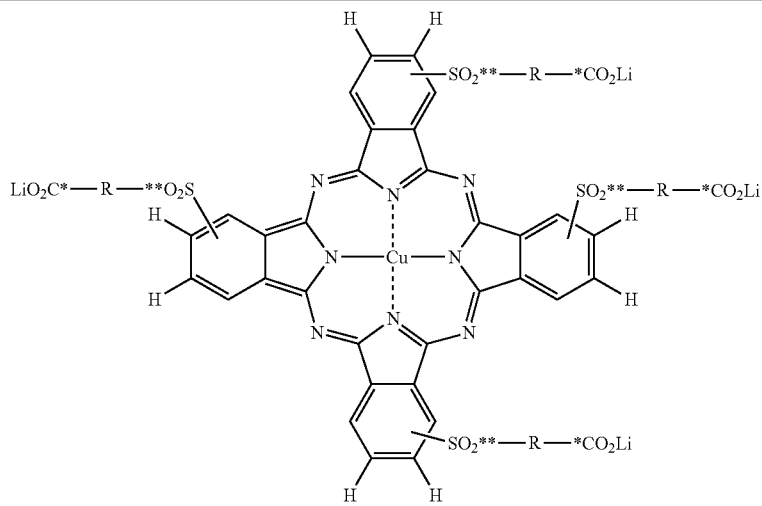

| | | Exemplified compound |
|---|---|---|
| **—R—* = | **—CH$_2$CH$_2$—* | 260 |
| | **—CH$_2$CH$_2$CH$_2$—* | 261 |
| | **—CH$_2$CH$_2$CH$_2$CH$_2$—* | 262 |
| | **—CH$_2$CH$_2$CH$_2$CH$_2$CH$_2$—* | 263 |
| | **—CH$_2$CH$_2$—(OCH$_2$CH$_2$)$n$—* | 264 |
| | $n = 1$ | 265 |
| | 2 | 266 |
| | 3 | 267 |
| | 4 | 268 |
| | 5 | 269 |
| |  | 270 |
| |  | 271 |
| |  | 272 |
| |  | 273 |

-continued
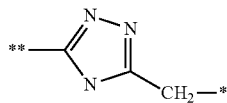
274
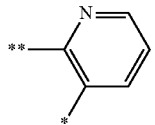
275
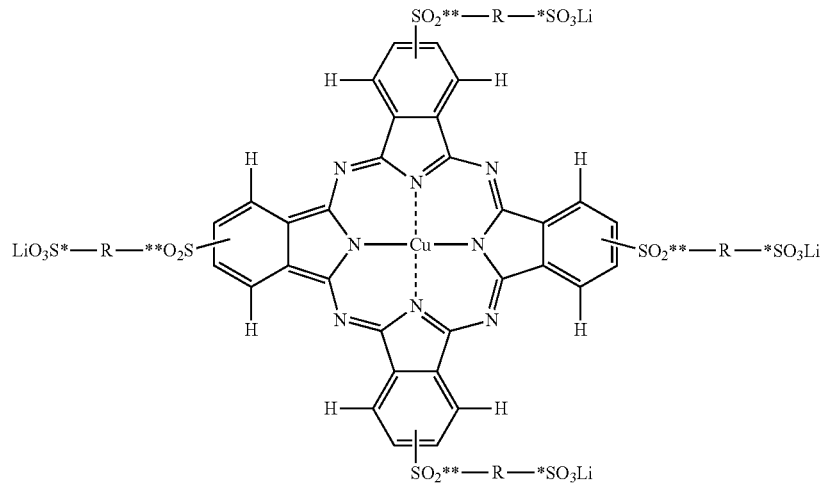
|  | Exemplified compound |
|---|---|
| **—R—* = | |
| **—CH$_2$CH$_2$—* | 276 |
| **—CH$_2$CH$_2$CH$_2$—* | 277 |
| **—CH$_2$CH$_2$CH$_2$CH$_2$—* | 278 |
| **—CH$_2$CH$_2$CH$_2$CH$_2$CH$_2$—* | 279 |
| **—CH$_2$CH$_2$—(OCH$_2$CH$_2$)$n$—* | |
| $n = 1$ | 280 |
| 2 | 281 |
| 3 | 282 |
| 4 | 283 |
| 5 | 284 |
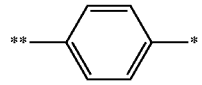
285
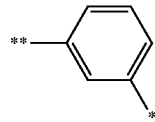
286
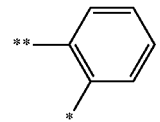
287
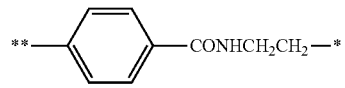
288
289

-continued
| | | 290 |
|---|---|---|
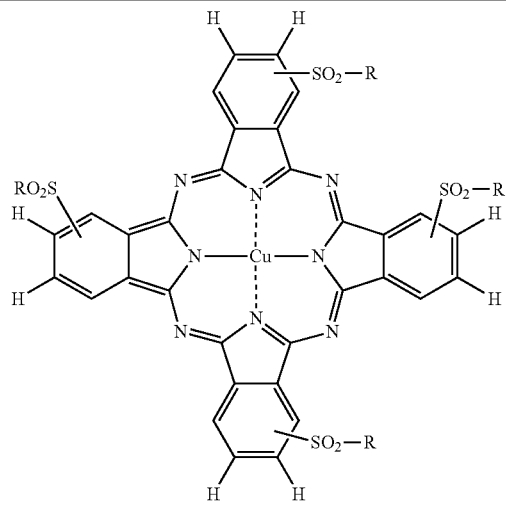
| | | Exemplified compound |
|---|---|---|
| R = | CH₃ | 291 |
| | C₂H₅ | 292 |
| | n-Pr | 293 |
| | i-Pr | 294 |
| | n-Bu | 295 |
| | s-Bu | 296 |
| | t-Bu | 297 |
| | i-Bu | 298 |
| | n-C₅H₁₁ | 299 |
| | cyclohexyl | 300 |
| | 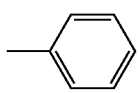 | 301 |
| | 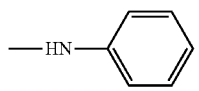 | 302 |
| | 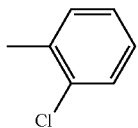 | 303 |
| | 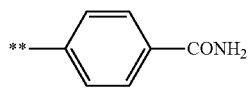 | 304 |
| | 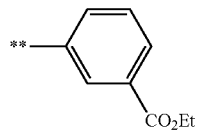 | 305 |
| | 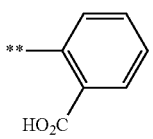 | 306 |

-continued
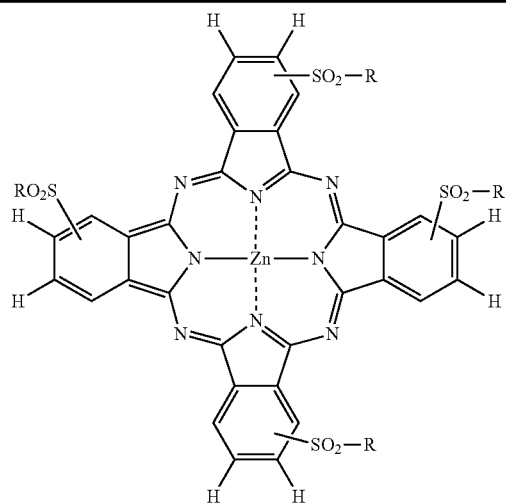
| R = | | |
|---|---|---|
| | n-Pr | 307 |
| | i-Pr | 308 |
| | n-Bu | 309 |
| | s-Bu | 310 |
| | t-Bu | 311 |
| | i-Bu | 312 |("
| 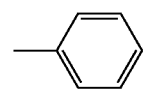 | | 313 |
| 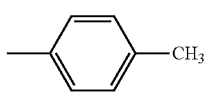 | | 314 |
| 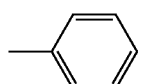 | | 315 |
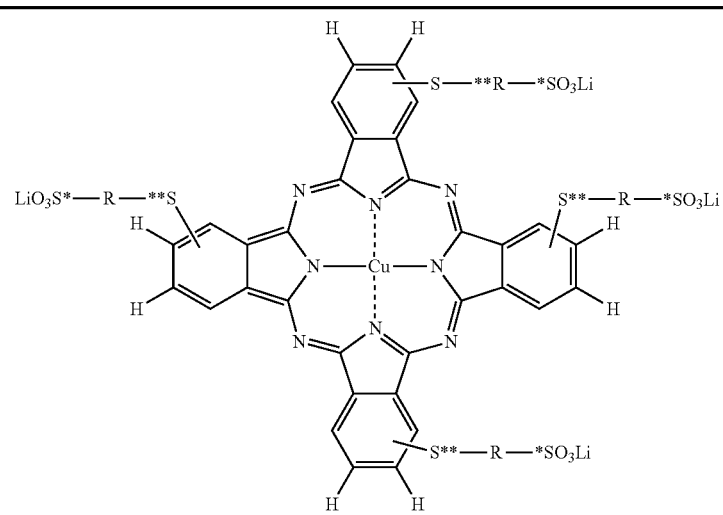
| | | Exemplified compound |
|---|---|---|
| **—R—* = | **—CH$_2$CH$_2$—* | 316 |
| | **—CH$_2$CH$_2$CH$_2$—* | 317 |
| | **—CH$_2$CH$_2$CH$_2$CH$_2$—* | 318 |
| | **—CH$_2$CH$_2$CH$_2$CH$_2$CH$_2$—* | 319 |
| | **—CH$_2$CH$_2$—(OCH$_2$CH$_2$)$n$—* | |

-continued
| | | |
|---|---|---|
| n = 1 | | 320 |
| 2 | | 321 |
| 3 | | 322 |
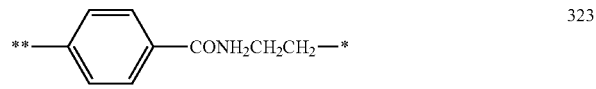 323
 324
 325
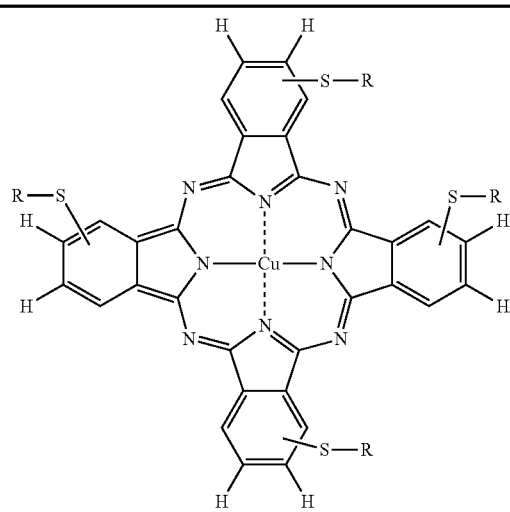
| | | Exemplified compound |
|---|---|---|
| R = | $CH_3$ | 326 |
| | $C_2H_5$ | 327 |
| | n-Pr | 328 |
| | i-Pr | 329 |
| | n-Bu | 330 |
| | s-Bu | 331 |
| | t-Bu | 332 |
| | i-Bu | 333 |
| | n-$C_5H_{11}$ | 334 |
| | cyclohexyl | 335 |
| |  | 336 |
| | 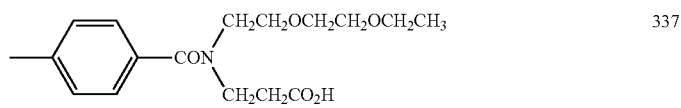 | 337 |
| | 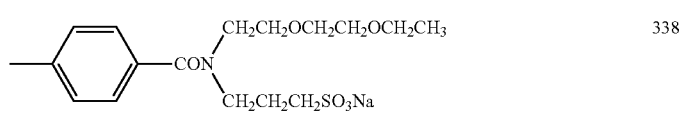 | 338 |
| | 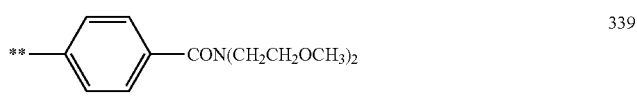 | 339 |

-continued
| | | |
|---|---|---|
|  | | 340 |
| 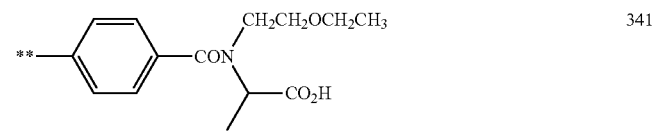 | | 341 |
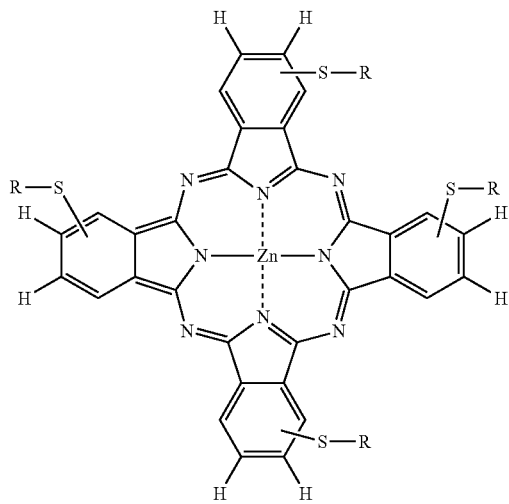
| | | Exemplified compound |
|---|---|---|
| R = | n-Bu | 342 |
| | s-Bu | 343 |
| | t-Bu | 344 |
| | i-Bu | 345 |
| | n-C$_5$H$_{11}$ | 346 |
| |  | 347 |
| | 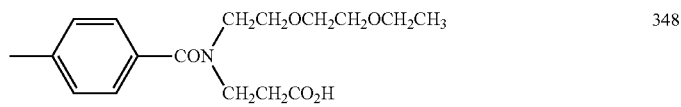 | 348 |
| | 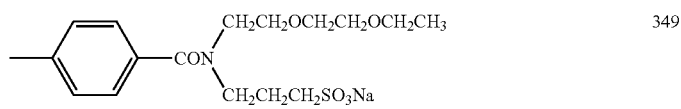 | 349 |
| 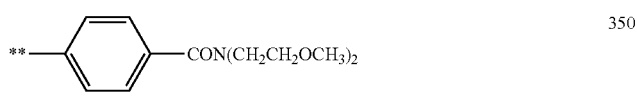 | | 350 |
| 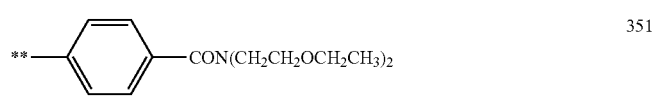 | | 351 |
| 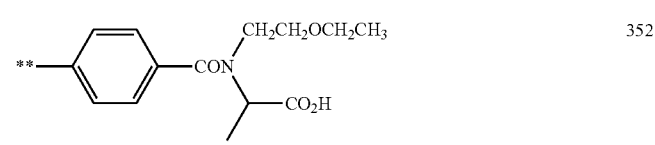 | | 352 |

-continued
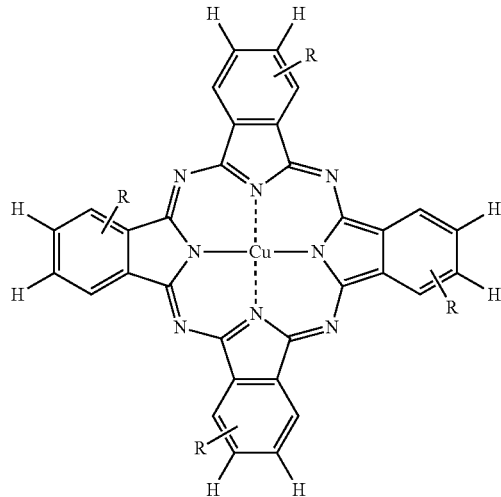
353
R: 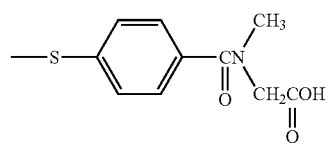 1
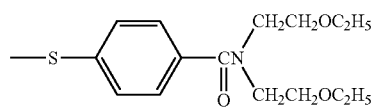 3
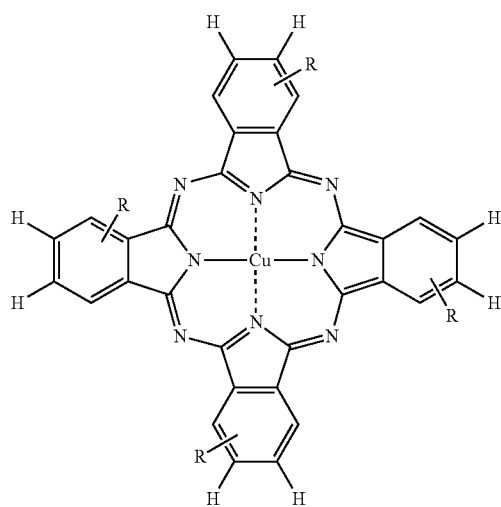
354
—R: 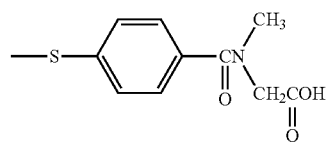 2
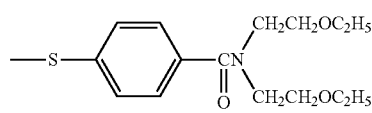 2

-continued
355
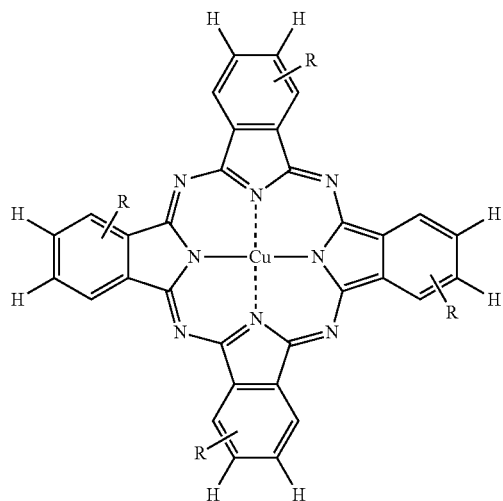
R:
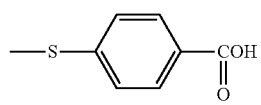 1
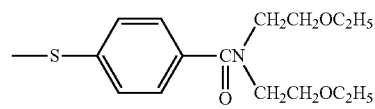 3
356
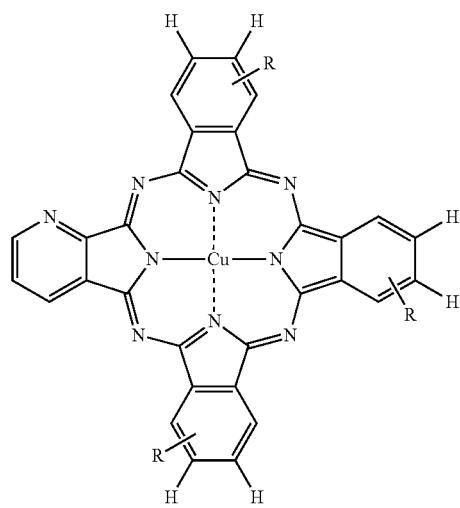
R:
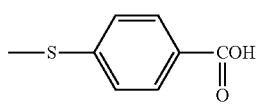 1
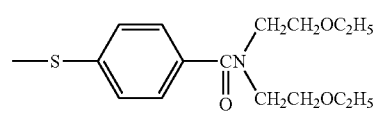 2

357

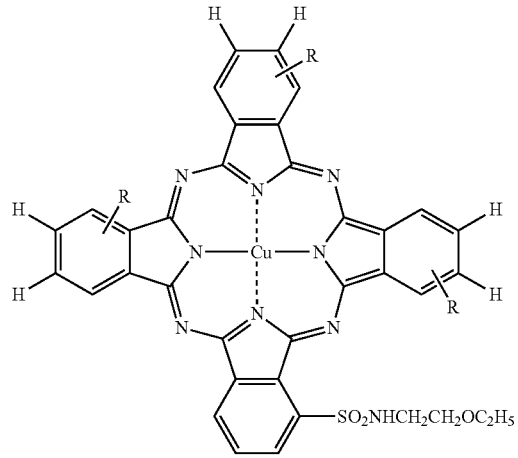

R:

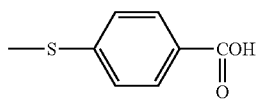 1

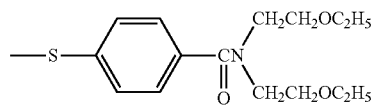 2

Next, the dehydrating agent, that can be used in the present invention, preferably in the second embodiment of the present invention, will be described.

Examples of the dehydrating agent include: a dehydrating agent absorbing water molecules (e.g. Molecular sieves (registered trademark), Drierite (registered trademark), magnesium sulfate, or sodium sulfate); an organic compound that gives a distillate containing water, when distilling a mixture of it and water under atmospheric pressure or reduced pressure (e.g. benzene, toluene, xylene, ethanol, methanol, or acetonitrile); and a dehydrating agent causing a chemical reaction with water [e.g. an organometallic compound (e.g. a Grignard reaction agent, an organolithium reaction agent, or an organozinc reaction agent), an acid anhydride (a carboxylic anhydride, a sulfonic anhydride, or a mixed acid anhydride), an acid halide, polyphosphoric acid, phosphorus pentaoxide, phosphorus oxychloride, phosphorus pentachloride, phosphorus trichloride, an orthoester compound, an acetal compound, an alkenyl ether compound, an alkenyl ester compound, an oxirane compound, or an oxetane compound].

The dehydrating agent to be used is preferably a dehydrating agent causing a chemical reaction with water. The dehydrating agent to be used is more preferably an acetal compound, an orthoester compound, an alkenyl ether compound, an alkenyl ester compound, an epoxide compound, or an oxetane compound, furthermore preferably an acetal compound, an orthoester compound, or an alkenyl ether compound. In the case where the dehydrating agent to be used is a substance containing a carbon atom(s), the total number of carbon atom(s) is generally 1 to 50, preferably 1 to 30, and more preferably 1 to 20.

The dehydrating agent causing a chemical reaction with water is particularly preferably the aforesaid dehydrating agent that can be preferably used in the first embodiment of the present invention, but the present invention is not limited to these.

It is necessary to add the dehydrating agent causing a chemical reaction with water in an amount capable of removing water in a reaction mixture to a level providing no effect on a phthalocyanine production reaction, and a necessary amount of the dehydrating agent is determined by the amount of water in the reaction mixture and the dehydration efficiency of the dehydrating agent to be used. Thus, the necessary amount of the dehydrating agent is determined case by case, and cannot be defined uniformly. The amount of the dehydrating agent to be added is preferably 0.1 to 500 mol % with respect to the phthalonitrile. The dehydrating agent may be added at any stage of the reaction, but is preferably added before starting the reaction, i.e. at the time when placing reaction substrates in a reaction vessel. In the case where operations, e.g. heating, conducting pressure reduction, and conducting reaction in a stream of an inert gas, are required, as auxiliary operations for improving the dehydration efficiency of the dehydrating agent, any appropriate operations may be performed.

In the present invention, particularly in the second embodiment of the present invention, an organic compound providing a distillate containing water after distillation of a mixture of the organic compound and water under atmospheric pressure or reduced pressure, may preferably be used as a dehydrating agent.

Such an organic compound is added to a reaction mixture and is distilled off with water through a distillation operation under appropriate pressure and temperature conditions, to carry out dehydration of the reaction mixture. Examples of the organic compound that can be used include: an alcohol compound, e.g. methanol, ethanol, 1-propanol, 2-propanol, 1-butanol, cyclohexanol, 1-octanol, or methoxyethanol; a ketone compound, e.g. acetone or methyl ethyl ketone; an aromatic compound, e.g. benzene, toluene, anisol, chlorobenzene, or phenol; a heterocyclic compound, e.g. furfuryl alcohol, 2-methylpyridine, 1,4-dioxane, or tetrahydrofuran; a halogenated alkyl compound, e.g. chloroform or carbon tetrachloride; a nitro compound, e.g. nitromethane or nitroethane; and a nitrile compound, e.g. acetonitrile or propionitrile. The organic compound distilled off with water in distillation and exhibiting a dehydration effect may be: an organic compound forming an azeotropic mixture with water, e.g. ethanol or toluene (definition of the azeotropic mixture is described in "Kagaku Jiten", published by Tokyo Kagaku Dozin Co., Ltd., p. 349 (1994), and specific examples of the azeotropic mixture may be referred to the description in "Azeotropic Data-III", published by the American Chemical Society, p. 13-45 (1973)); or an organic compound forming no azeotropic mixture with water, e.g. methanol.

As the organic compound that is distilled off with water in distillation to exhibit a dehydration effect, preferably use may be made of an alcohol compound or an aromatic compound. More preferably use may be made of an organic compound whose boiling point as a single substance is 50 to 200° C. under atmospheric pressure, and further preferably 60 to 150° C. under atmospheric pressure. Particularly preferably use may be made of methanol, ethanol, 1-propanol, 2-propanol, 1-butanol, 2-butanol, 2-methyl-1-propanol, methoxyethanol, ethoxyethanol, 2-methoxy-1-propanol, 3-methoxy-1-propanol, 1-methoxy-2-propanol, toluene, xylene, or chlorobenzene.

One of the above organic compounds each of which is distilled off with water in distillation to exhibit a dehydration effect may be used singly, or a plurality of the above organic compounds may be used in combination. The dehydration operation may be performed any number of times. In the case where the dehydration operation is performed a plurality of times, the same dehydrating agent may be used or different dehydrating agents may be used. The dehydration operation is preferably performed 1 to 3 times, and a plurality of dehydrating agents are appropriately used. It is necessary to use this kind of dehydrating agent in an amount capable of removing water in a reaction mixture to a level improving the yield in a phthalocyanine production reaction, and a necessary amount of the dehydrating agent is determined by the amount of water in the reaction mixture and the dehydration efficiency of the dehydrating agent to be used. Thus, the necessary amount of the dehydrating agent is determined case by case, and cannot be defined uniformly. The amount of the dehydrating agent to be used is preferably 1 to 200% by volume, more preferably 10 to 100%, with respect to the volume of the reaction mixture except the dehydrating agent.

The dehydration operation through distillation off of the dehydrating agent may be conducted at any stage of the synthesis operation. It is preferable to conduct the operation in the order of: preparing a mixture of a phthalonitrile derivative, a reaction solvent, and a dehydrating agent (a carboxylic acid is added as required); performing a dehydration operation; and then adding an ammonium salt. In the case where operations under heating, reduced pressure, or a stream of an inert gas, are required, as auxiliary operations for improving the dehydration efficiency of the dehydrating agent, any appropriate operations may be performed. The dehydration operation is performed in the temperature range of preferably 50 to 200° C., more preferably 60 to 150° C., and particularly preferably 60 to 130° C.

Next, the ammonium salt compound that can be used in the present invention, particularly in the second embodiment of the present invention, will be described.

An ammonium salt referred to herein means to include: a salt of an amine compound (including ammonia) and an acid; and a quaternary ammonium salt of an acid. The amine compound may include an amine moiety in the molecule, as can be seen in an amino acid in which an amine structure is present in the molecule of the acid; or alternatively the amine compound may include no such a moiety in the molecule.

First, description will be made for the acid.

Examples of the acid which can be used herein include a carboxylic acid (e.g. an aliphatic carboxylic acid, an aromatic carboxylic acid, or a heterocyclic carboxylic acid), sulfonic acid (e.g. an aliphatic sulfonic acid, an aromatic sulfonic acid, or a heterocyclic sulfonic acid), sulfinic acid (e.g. an aliphatic sulfinic acid, an aromatic sulfinic acid, or a heterocyclic sulfinic acid), carbonic acid, sulfuric acid, hydrochloric acid, phosphoric acid, and phosphomolybdic acid. As the acid moiety, a carboxylic acid (e.g. an aliphatic carboxylic acid, an aromatic carboxylic acid, or a heterocyclic carboxylic acid) is preferable. Each of carboxylic acids of those salts may be a monocarboxylic acid or a dicarboxylic acid or polycarboxylic acid having two or more carboxyl groups, but is preferably a monocarboxylic acid.

A preferred example of the aliphatic carboxylic acid is a saturated or unsaturated, linear, branched, or cyclic, and substituted or unsubstituted aliphatic carboxylic acid having 1 to 30 carbon atoms (more preferably 1 to 10 carbon atoms). Specific examples thereof include formic acid, oxalic acid, acetic acid, propionic acid, butanoic acid, butyric acid, acrylic acid, and cyclohexanecarboxylic acid. A preferred example of the aromatic carboxylic acid is a substituted or unsubstituted aromatic carboxylic acid having 7 to 30 carbon atoms. Specific examples thereof include benzoic acid, toluic acid, and phthalic acid. A preferred example of the heterocyclic carboxylic acid is a saturated or unsaturated, and substituted or unsubstituted heterocyclic carboxylic acid having 1 to 30 carbon atoms (more preferably 3 to 10 carbon atoms). Specific examples thereof include nicotinic acid, isonicotinic acid, and 1-pyrrolecarboxylic acid.

Of these, the carboxylic acid is more preferably an aliphatic carboxylic acid or an aromatic carboxylic acid, further preferably a saturated aliphatic carboxylic acid having 1 to 6 carbon atoms or an aromatic carboxylic acid having 7 to 10 carbon atoms, and particularly preferably acetic acid or benzoic acid.

Next, description will be made for the amine compound.

Examples of the amine compound which can be used herein include ammonia, an amine compound (i.e. a primary amine compound, a secondary amine compound, or a tertiary amine compound), a hydroxyamine compound, and a hydrazine compound. Of those, ammonia or an amine compound (i.e. a primary amine compound, a secondary amine compound, or a tertiary amine compound) is preferably used; and ammonia, a primary amine compound, or a secondary amine compound is more preferably used. Ammonia or monoalkylamine (having 1 to 10 carbon atoms) is still more preferably used, and ammonia is particularly preferably used.

Each of the same acids as those described above is preferably used herein for the quaternary ammonium salt of the acid. Examples of the quaternary ammonium moiety which can be used include tetraalkyl ammonium, trialkylmonoaryl ammonium, dialkyldiaryl ammonium, and monoalkyltriaryl ammonium. A heterocycle having a quaternarized nitrogen atom can also be used herein. Of those, tetraalkyl ammonium or trialkylmonoaryl ammonium is preferably used. Tetraalkyl ammonium is more preferably used. Tetraalkyl ammonium having 4 to 50 carbon atoms in total is still more preferably used. Tetrabutyl ammonium, tetrapropyl ammonium, tetraethyl ammonium, tetramethyl ammonium, or benzyltrimethyl ammonium is particularly preferably used.

The ammonium salt that can be used in the present invention, preferable in the second embodiment of the present invention, is: preferably an ammonium salt of an aliphatic carboxylic acid, an ammonium salt of an aromatic carboxylic acid, or ammonium carbonate; more preferably an ammonium salt of a saturated aliphatic carboxylic acid having 1 to 6 carbon atoms, an ammonium salt of an aromatic carboxylic acid having 7 to 10 carbon atoms, or ammonium carbonate; furthermore preferably ammonium acetate, ammonium propionate, ammonium benzoate, or ammonium carbonate; and particularly preferably ammonium acetate or ammonium benzoate.

An action of the ammonium salt that can be used in the present invention, preferable in the second embodiment of the present invention, advances the reaction under mild conditions, and improves the yield of the reaction. Further, compared to a method employing a conventionally known base (e.g. a metal alkoxide, DBU, or DBN), the method of the present invention allows use of, as a substrate, a precursor, e.g. a phthalonitrile compound having an unstable functional group under basic conditions.

An amount to be used of the ammonium salt that can be used in the present invention, preferable in the second embodiment of the present invention, is generally in the range of 0.01 to 2,000 mol %, preferably 1 to 1,000 mol %, more preferably 20 to 500 mol %, and further preferably 50 to 400 mol %, with respect to the amount to be used of the phthalonitrile compound.

In the present invention, preferably in the second embodiment of the present invention, the reaction is preferably performed in the presence of an acid, in addition to the ammonium salt. The acid that can be used herein refers to an (aliphatic, aromatic, or heterocyclic) carboxylic acid, an (aliphatic, aromatic, or heterocyclic) sulfonic acid, or an (aliphatic, aromatic, or heterocyclic) phosphoric acid. The acid that can be used is preferably an (aliphatic, aromatic, or heterocyclic) carboxylic acid.

Next, the carboxylic acid that can be preferably used in the present invention, particularly in the second embodiment of the present invention, is described.

Preferred examples of the carboxylic acid include an aliphatic carboxylic acid, an aromatic carboxylic acid, and a heterocyclic carboxylic acid. The carboxylic acid may be a monocarboxylic acid, or a dicarboxylic acid or polycarboxylic acid having two or more carboxyl groups, but is preferably a monocarboxylic acid.

A preferred example of the aliphatic carboxylic acid is a saturated or unsaturated, linear, branched, or cyclic, and substituted or unsubstituted aliphatic carboxylic acid having 1 to 30 carbon atoms (more preferably 1 to 10 carbon atoms). Specific examples thereof include formic acid, oxalic acid, acetic acid, propionic acid, butanoic acid, butyric acid, acrylic acid, and cyclohexanecarboxylic acid. A preferred example of the aromatic carboxylic acid is a substituted or unsubstituted aromatic carboxylic acid having 7 to 30 carbon atoms. Specific examples thereof include benzoic acid, toluic acid, and phthalic acid. A preferred example of the heterocyclic carboxylic acid is a saturated or unsaturated, and substituted or unsubstituted heterocyclic carboxylic acid having 1 to 30 carbon atoms (more preferably 3 to 10 carbon atoms). Specific examples thereof include nicotinic acid, isonicotinic acid, and 1-pyrrolecarboxylic acid.

Of these, the carboxylic acid is preferably an aliphatic carboxylic acid or an aromatic carboxylic acid, more preferably a saturated aliphatic carboxylic acid having 1 to 6 carbon atoms or an aromatic carboxylic acid having 7 to 10 carbon atoms, further preferably a saturated aliphatic carboxylic acid having 1 to 6 carbon atoms, and particularly preferably acetic acid.

The amount to be used of the carboxylic acid is generally in the range of 0.001 to 1,000 mol %, preferably 0.01 to 100 mol %, and more preferably 0.01 to 50 mol %, with respect to the amount to be used of the phthalonitrile compound.

A solvent may be used, as required, when carrying out the synthesis method of the present invention, particularly the second embodiment of the present invention. Examples of the solvent that can be used include: an alcohol compound; an aromatic compound, e.g. trichlorobenzene, chloronaphthalene, or nitrobenzene; sulfolane; and a urea compound, e.g. urea. An arbitrary amount of the solvent may be used, but the amount of the solvent is preferably 1 to 100 times by mass, and more preferably 5 to 20 times by mass of that of the phthalonitrile compound. An alcohol compound is preferably used as a solvent, and an alcohol compound having a boiling point of 80° C. or higher is more preferably used. Further preferred examples of the solvent include butanol, pentanol, hexanol, octanol, ethylene glycol, 2-methoxy-1-propanol, diethylene glycol, triethylene glycol, polyethylene glycol (having an average molecular weight of 200 to 2,000), glycerin, 1,2-propanediol, polypropylene glycol (having an average molecular weight of 200 to 2,000), 1,3-propanediol, and 1,4-butanediol. Particularly preferred examples of the solvent include butanol, octanol, ethylene glycol, diethylene glycol, and triethylene glycol.

In synthesis of a metal phthalocyanine derivative in the present invention, particularly in the second embodiment of the present invention, the metal salt to be used in the reaction may be in the form of: a halide, an oxide, a hydroxide, an alkoxide, a carboxylate, a sulfonate, or an organometal compound; preferably a halide, a hydroxide, an alkoxide, a carboxylate, a sulfonate, or an organometal compound; more preferably a halide, an oxide, a carboxylate, or a sulfonate; further preferably a halide or a carboxylate; particularly preferably a chloride or an acetate; and most preferably a chloride.

Any amount of the metal salt may be used in the reaction as required, but for production of the compound represented by formula (13), metal salts corresponding to $M_1$ and $M_2$ are each used in an amount of preferably 20 to 300 mol %, and more preferably 30 to 100 mol %, with respect to the amount of the compound represented by formula (11) or (12). On the other hand, for production of the compound represented by formula (14), a metal salt corresponding to $M_3$ is used in an amount of preferably 10 to 200 mol %, and more preferably 15 to 100 mol %, with respect to the amount of the compound represented by formula (11) or (12).

The phthalocyanine synthetic reaction is performed in the reaction temperature range of preferably 70 to 300° C., more preferably 80 to 200° C., and further preferably 80 to 150° C. A reaction time is in the range of preferably 1 to 40 hours, and more preferably 2 to 15 hours.

In the case where pH of the reaction system should be adjusted, an acid or base required for the pH adjustment may be arbitrarily added. The acid may be the carboxylic acid described above, or an organic or inorganic acid except the carboxylic acid. Examples of the acid that can be preferably used include hydrochloric acid, sulfuric acid, and an organic sulfonic acid (e.g. methanesulfonic acid or toluenesulfonic acid).

Examples of the base that can be preferably used include ammonia, triethylamine, ammonium carbonate, sodium carbonate, sodium hydrogen carbonate, potassium carbonate, and sodium acetate.

The method of the present invention allows production of a metal phthalocyanine compound in high yield, and high purity, with favorable operability, and industrial stability.

The production method of the present invention allows synthesis of a variety of phthalocyanine compounds having various substituents efficiently in high yield.

The present invention will be described in more detail based on the following examples, but the invention is not intended to be limited thereto.

EXAMPLES

Compounds 2, 5 and the like (reactants) in the examples can be produced through the method described in JP-A-2004-2670, JP-A-2005-41856, Japanese Patent Application No. 2004-094413, or JP-A-2003-119415, and each of the compounds belong to the compound represented by formula (I), (II), (III) or (IV).

Example 1

Production of Dye Compound Containing Phthalocyanine Compound 1 as Main Component To 120 mL of diethylene glycol, 0.6 mL of acetic acid and 21.2 g of triethyl orthoacetate were added at room temperature. Then, 21.44 g of Compound 2 (water content 3%) and 8.29 g of Compound 5 (water content 1%) were subsequently admixed thereto, and the resultant mixture was heated to an inner temperature 100° C. After 3.0 g of $CuCl_2$ and 24.8 g of ammonium benzoate were added to the reaction mixture, the resultant mixture was stirred at an inner temperature 100° C. for 1.5 hours.

Then, the mixture was cooled to an inner temperature 90° C., and 7.7 mL of concentrated hydrochloric acid was added dropwise thereto. Then, 4.28 g of lithium chloride was added thereto, and the resultant mixture was stirred at an inner temperature 90° C. for 30 minutes. Thereafter, 360 mL of isopropanol was added dropwise to the mixture for crystallization. After stirring at an inner temperature 80° C. for 1 hour and then cooling to 30° C., precipitates were obtained through suction filtration, and the precipitates were washed with 500 mL of isopropanol by pouring the isopropanol upon the precipitates. Then, the resultant precipitates were dried, to thereby obtain 31.44 g of crude crystals.

After 30.0 g of the crude crystals were dissolved in 38.3 mL of ion-exchanged water and 90.7 g of methanol, a 2.5N—

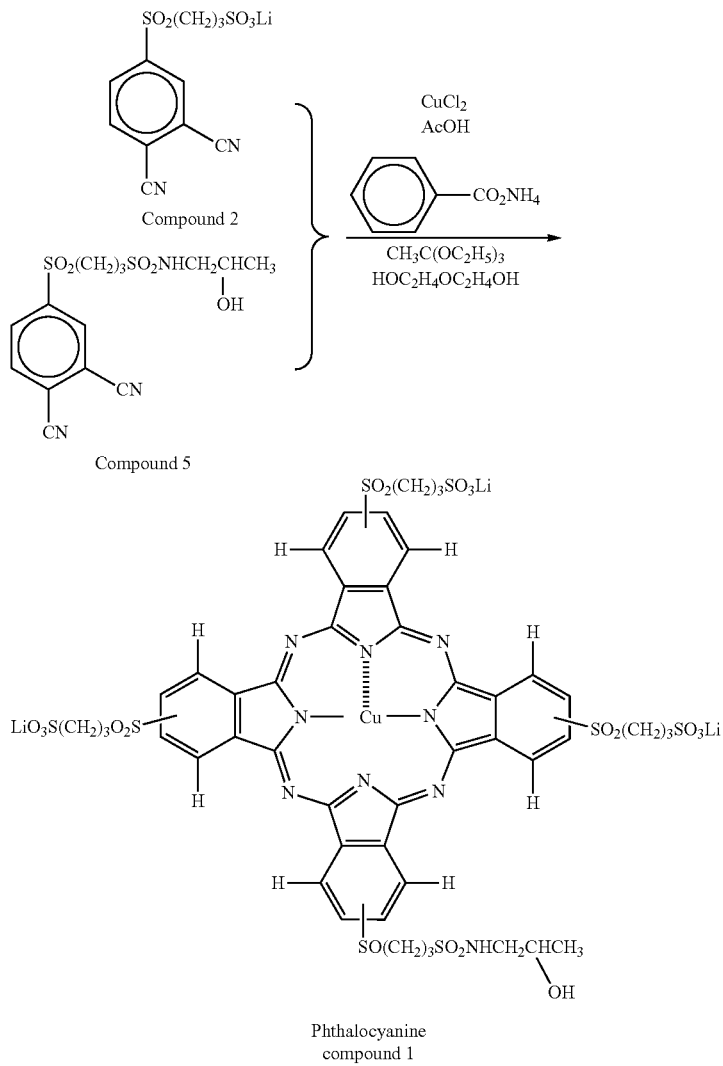

LiOH aqueous solution was added to the mixture at 50° C. until the pH reached 9.5. The mixture was stirred at 50° C. for 60 minutes, and impurities were removed through filtration. The resultant was heated to an inner temperature 90° C., and 450 mL of isopropanol was added dropwise thereto for crystallization. The mixture was cooled to an inner temperature 30° C., and purified crystals were obtained through suction filtration and washed with 250 mL of isopropanol by pouring the isopropanol upon the crystals. Yield 27.3 g (yield 91%) Solution absorption: λmax=624.7 nm, ε 59,000 ($H_2O$) (2.5 mg of Phthalocyanine compound 1/100 mL of ultrapure water)

Example 2

Production of Dye Compound Containing Phthalocyanine Compound 2 as Main Component

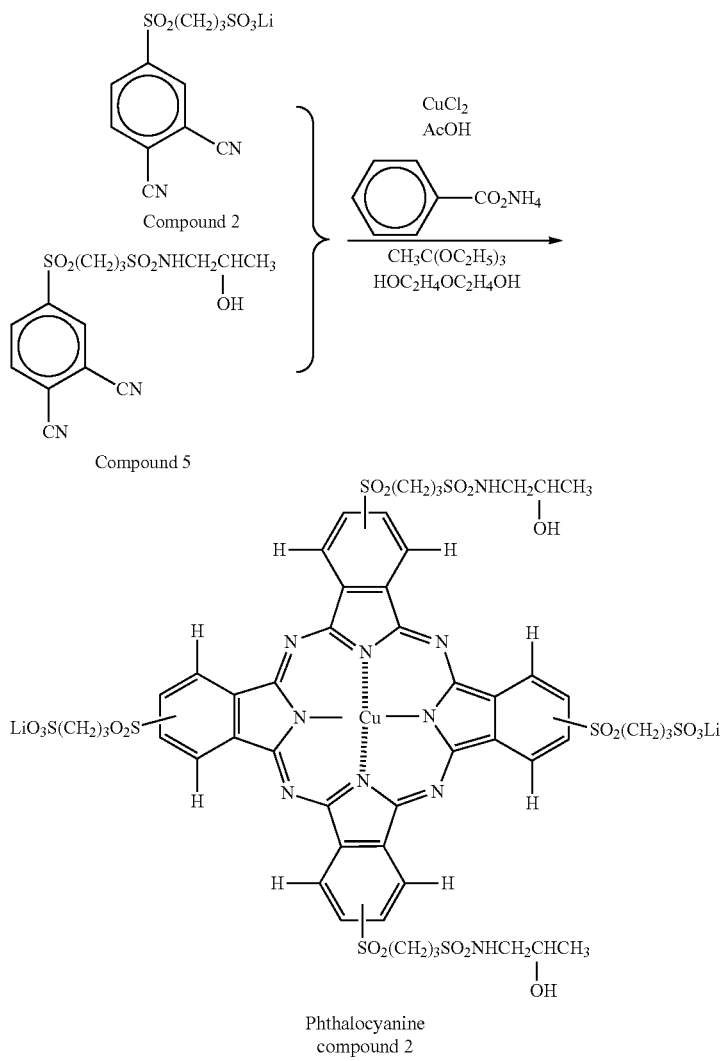

Phthalocyanine compound 2

To 120 mL of diethylene glycol, 0.6 mL of acetic acid and 21.2 g of triethyl orthoacetate were added at room temperature. Then, 14.29 g of Compound 2 (water content 3%) and 16.58 g of Compound 5 (water content 1%) were subsequently admixed thereto, and the mixture was heated to an inner temperature 100° C. After 3.0 g of $CuCl_2$ and 24.8 g of ammonium benzoate were added to the reaction mixture, the resultant mixture was stirred at an inner temperature 100° C. for 1.5 hours.

Then, the mixture was cooled to an inner temperature 90° C., and 7.7 mL of concentrated hydrochloric acid was added dropwise thereto. Then, 4.28 g of lithium chloride was added thereto, and the mixture was stirred at an inner temperature 90° C. for 30 minutes. Thereafter, 360 mL of isopropanol was added dropwise to the mixture for crystallization. After stirring at an inner temperature 80° C. for 1 hour and then cooling to 30° C., precipitates were obtained through suction filtration, and were washed with 500 mL of isopropanol by pouring the isopropanol upon the precipitates. Then, the resultant precipitates were dried, to thereby obtain 33.5 g of crude crystals.

After 30.0 g of the crude crystals were dissolved in 120 mL of a 0.1N—LiOH aqueous solution at 60° C., impurities were removed through filtration. The resultant was stirred at the same temperature for 30 minutes. After 30 mL of methanol was poured thereinto, a 1.0N—LiOH aqueous solution was added thereto at 50° C. until the pH reached 8.5. The resultant was heated to an inner temperature 60° C., and 6,000 mL of isopropanol was added dropwise thereto for crystallization. After cooling to an inner temperature 30° C., purified crystals were obtained through suction filtration and were washed with 300 mL of isopropanol by pouring the isopropanol upon the crystals. Yield 27.0 g (yield 90%)

Solution absorption: λmax=615.8 nm, ε 52,000 ($H_2O$) (2.4 mg of Phthalocyanine compound 2/100 mL of ultrapure water)

Example 3

Production of Dye Compound Containing Phthalocyanine Compound 3 as Main Component ammonium benzoate were added to the reaction mixture, the resultant mixture was stirred at an inner temperature 100° C. for 1.5 hours.

The inner temperature of the reaction solution was lowered to room temperature by cooling, and the solution was subjected to crystallization from 300 mL of a 1.0N-hydrochloric acid. The thus-obtained precipitates were filtered, washed with 800 mL of water, and dried, to thereby obtain 35.6 of crude crystals.

After 30 g of the thus-dried crude crystals were dissolved in 300 mL of methanol, impurities were removed through filtration. Then, 600 mL of isopropanol was added dropwise thereto for crystallization. The resultant mixture was subjected to suction filtration, and the thus-obtained solids were

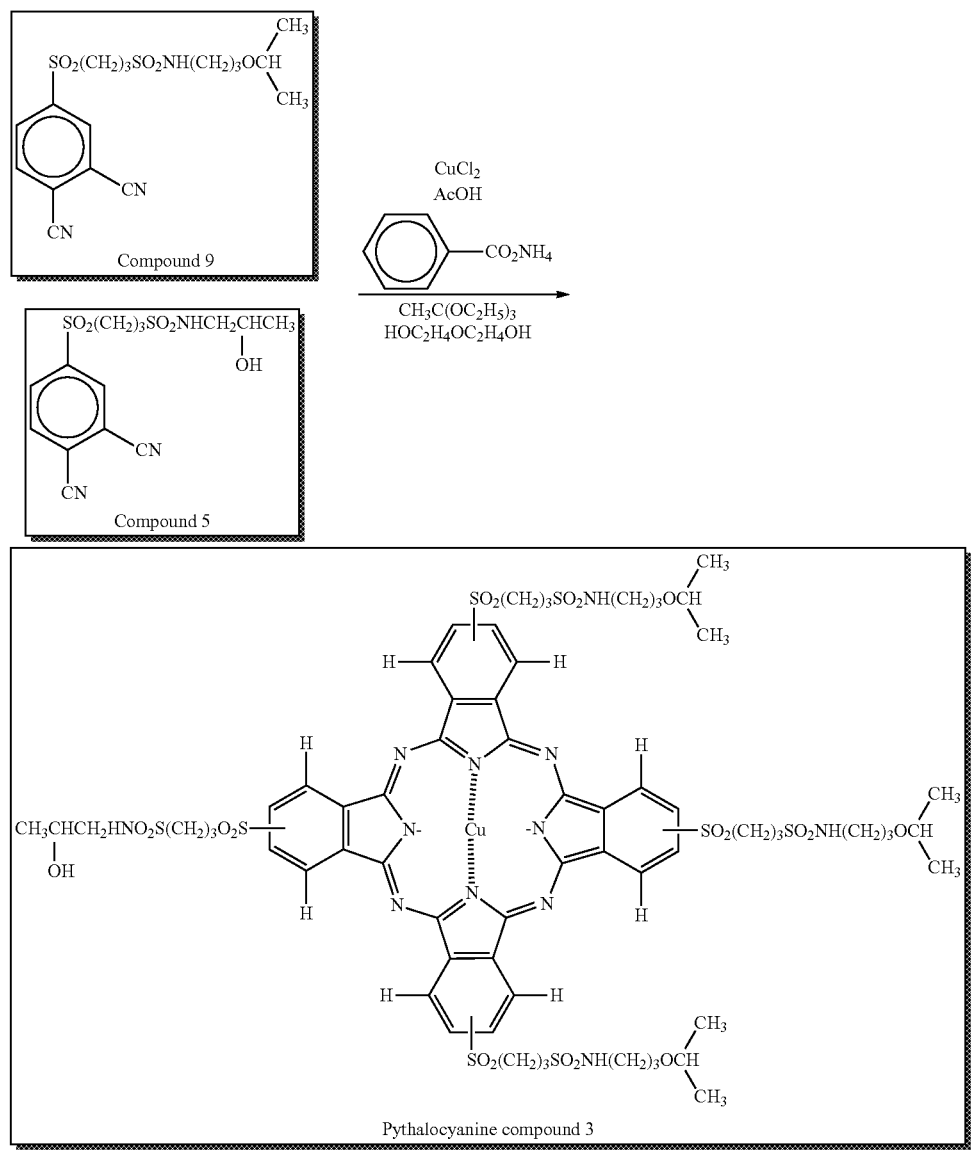

To 120 mL of diethylene glycol, 0.6 mL of acetic acid and 21.2 g of triethyl orthoacetate were added at room temperature. Then, 27.7 g of Compound 9 (water content 0.8%) and 8.29 g of Compound 5 (water content 1%) were subsequently admixed thereto, and the mixture was heated to an inner temperature 100° C. After 3.0 g of $CuCl_2$ and 24.8 g of washed with isopropanol by pouring the isopropanol upon the solids. Yield 27 g (yield 90.0%)

Solution absorption: λmax=595.6 nm, ε 35,200 (Ethyl acetate) (2.7 mg of Phthalocyanine compound 3/100 mL of ethyl acetate)

Examples 4 to 10

The following Table 1 collectively shows the results conducted in the same manner as in Example 1, except that the compounds represented by formula (I), (II), (III) or (IV), the base, and the like were changed.

Comparative Examples 1 to 10

Table 1 collectively shows the results conducted in the same manner as in Example 1, except that the compounds represented by formula (I), (II), (III) or (IV), the acid, the base, and the dehydrating agent were changed.

TABLE 1

| No. | Compound of formula (I), (II), (III) or (IV) (vs $CuCl_2$) | Reaction solvent | Reaction temperature | Reaction time | Acid | Base | Dehydrating agent | Yield Crude yield; (After purification) |
|---|---|---|---|---|---|---|---|---|
| Example 1 | Compound 2/Compound 5 = 3/1 (eq/eq) | $HOC_2H_4OC_2H_4OH$ | 100° C. | 1.5 hr | Acetic acid | Ammonium benzoate | $CH_3C(OC_2H_5)_3$ | 100%; (91%) |
| Example 2 | Compound 2/Compound 5 = 2/2 (eq/eq) | $HOC_2H_4OC_2H_4OH$ | 100° C. | 1.5 hr | Acetic acid | Ammonium benzoate | $CH_3C(OC_2H_5)_3$ | 102%; (90%) |
| Example 3 | Compound 9/Compound 5 = 3/1 (eq/eq) | $HOC_2H_4OC_2H_4OH$ | 100° C. | 1.5 hr | Acetic acid | Ammonium benzoate | $CH_3C(OC_2H_5)_3$ | 96%; (90%) |
| Example 4 | Compound 2/Compound 5 = 2/2 (eq/eq) | $HOC_2H_4OH$ | 100° C. | 1.5 hr | Acetic acid | Ammonium benzoate | $CH_3C(OC_2H_5)_3$ | 98%; (91%) |
| Example 5 | Compound 2/Compound 5 = 3/1 (eq/eq) | $HO(CH_2)_3OH$ | 100° C. | 1.5 hr | Acetic acid | Ammonium benzoate | $CH_3C(OC_2H_5)_3$ | 97%; (92%) |
| Example 6 | Compound 2/Compound 5 = 3/1 (eq/eq) | $HOCH_2CH(HO)CH_3$ | 100° C. | 1.5 hr | Acetic acid | Ammonium benzoate | $CH_3C(OC_2H_5)_3$ | 97%; (92%) |
| Example 7 | Compound 2/Compound 5 = 3/1 (eq/eq) | $HOC_2H_4OC_2H_4OH$ | 100° C. | 1.5 hr | Acetic acid | Ammonium acetate | $CH_3C(OC_2H_5)_3$ | 103%; (90%) |
| Example 8 | Compound 2/Compound 47 = 3/1 (eq/eq) | $HOC_2H_4OC_2H_4OH$ | 100° C. | 1.5 hr | Acetic acid | Ammonium benzoate | $CH_3C(OC_2H_5)_3$ | 96%; (90%) |
| Example 9 | Compound 2/Compound 48 = 3/1 (eq/eq) | $HOC_2H_4OC_2H_4OH$ | 100° C. | 1.5 hr | Acetic acid | Ammonium benzoate | $CH_3C(OC_2H_5)_3$ | 95%; (90%) |
| Example 10 | Compound 2/Compound 49 = 1/3 (eq/eq) | $HOC_2H_4OC_2H_4OH$ | 100° C. | 1.5 hr | Acetic acid | Ammonium benzoate | $CH_3C(OC_2H_5)_3$ | 93%; (89%) |
| Comparative example 1 | Compound 2/Compound 5 = 3/1 (eq/eq) | $HOC_2H_4OC_2H_4OH$ | 100° C. | 1.5 hr | None | Ammonium benzoate | $CH_3C(OC_2H_5)_3$ | 63%; (65%) |
| Comparative example 2 | Compound 2/Compound 5 = 3/1 (eq/eq) | $HOC_2H_4OC_2H_4OH$ | 100° C. | 1.5 hr | Acetic acid | None | $CH_3C(OC_2H_5)_3$ | 55%; (70%) |
| Comparative example 3 | Compound 2/Compound 5 = 3/1 (eq/eq) | $HOC_2H_4OC_2H_4OH$ | 100° C. | 1.5 hr | Acetic acid | Ammonium benzoate | None | 83%; (80%) |
| Comparative example 4 | Compound 2/Compound 5 = 3/1 (eq/eq) | $HOC_2H_4OC_2H_4OH$ | 100° C. | 8.0 hr | Acetic acid | Lithium acetate | None | 98%; (89%) |
| Comparative example 5 | Compound 2/Compound 5 = 3/1 (eq/eq) | $HOC_2H_4OC_2H_4OH$ | 100° C. | 1.5 hr | Acetic acid | None | None | 50%; (48%) |
| Comparative example 6 | Compound 2/Compound 5 = 3/1 (eq/eq) | $HOC_2H_4OC_2H_4OH$ | 100° C. | 1.5 hr | None | None | None | 30%; (33%) |
| Comparative example 7 | Compound 2/Compound 5 = 3/1 (eq/eq) | $HOC_2H_4OC_2H_4OH$ | 100° C. | 1.5 hr | None | None | $CH_3C(OC_2H_5)_3$ | 38%; (31%) |
| Comparative example 8 | Compound 2/Compound 5 = 2/2 (eq/eq) | $HOC_2H_4OC_2H_4OH$ | 100° C. | 1.5 hr | None | Ammonium benzoate | $CH_3C(OC_2H_5)_3$ | 60%; (58%) |
| Comparative example 9 | Compound 2/Compound 5 = 2/2 (eq/eq) | $HOC_2H_4OC_2H_4OH$ | 100° C. | 1.5 hr | Acetic acid | None | $CH_3C(OC_2H_5)_3$ | 50%; (67%) |
| Comparative example 10 | Compound 2/Compound 5 = 2/2 (eq/eq) | $HOC_2H_4OC_2H_4OH$ | 100° C. | 1.5 hr | Acetic acid | Ammonium benzoate | None | 80%; (72%) |

In Table 1, the phthalocyanine compound obtained in each of Examples 5 to 7 was the same as that of Example 1, and phthalocyanine compounds represented by formulae described below were obtained in Examples 8, 9, and 10. The yield after purification in Table 1 refers to the yield of each of the compounds represented by formulae described below.

Example 8
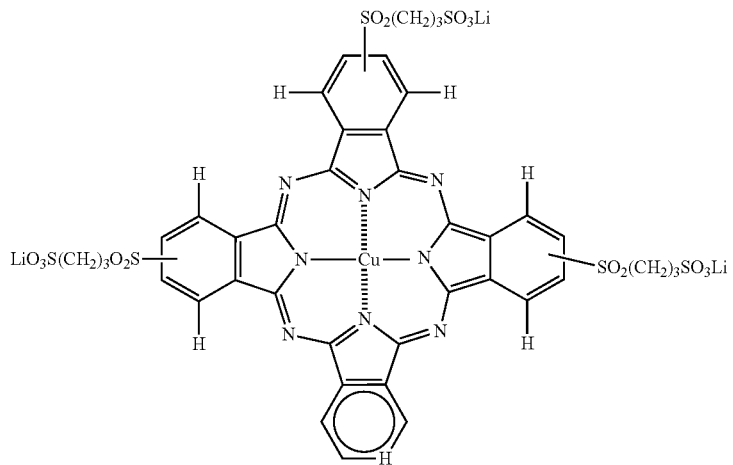
Example 9
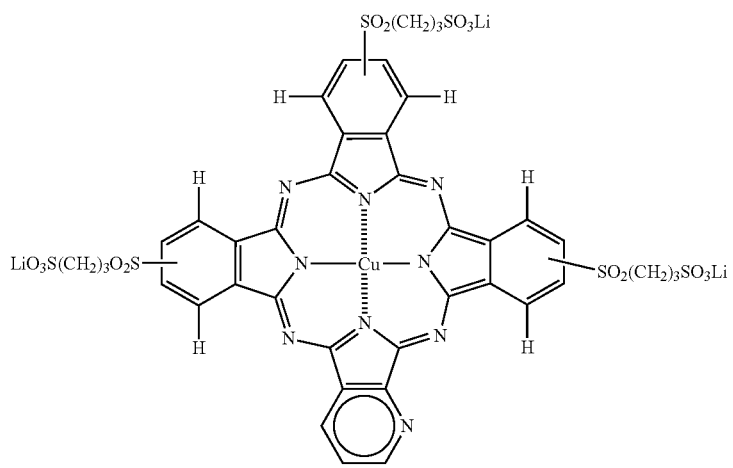
Example 10
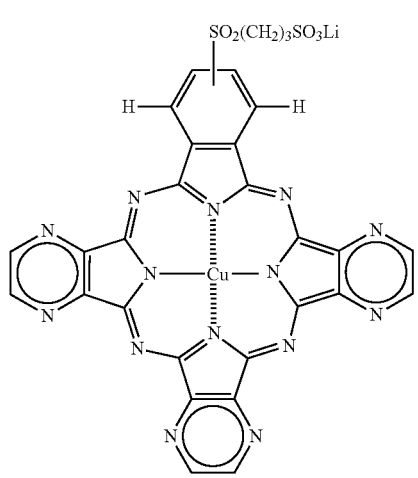

As is apparent from the above-mentioned results, the constituents of the present invention, particularly of the first embodiment of the present invention, allow production of a phthalocyanine compound with high yield and high purity, under mild conditions, in a short period of time.

Example 11

Synthesis of Phthalocyanine Compound 211

Phthalocyanine compound 211 was synthesized according to the following scheme.

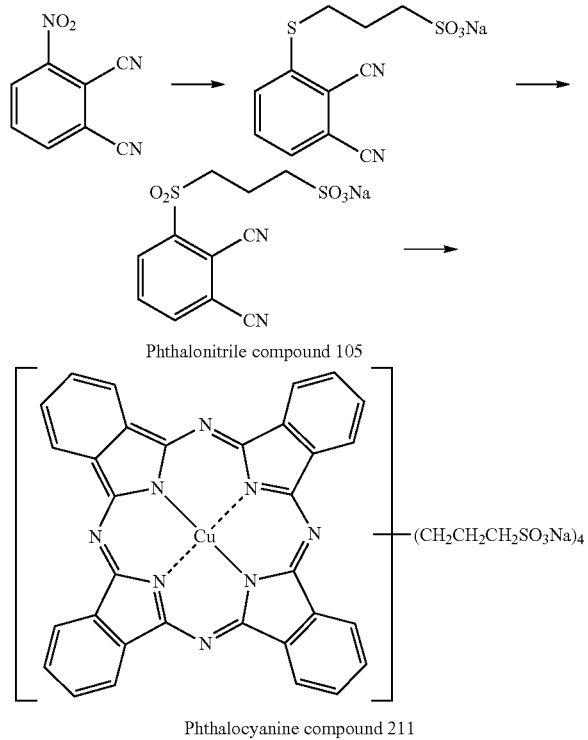

Phthalonitrile compound 105

Phthalocyanine compound 211

Synthesis of Phthalonitrile Compound 105

To a mixture of 3-nitrophthalonitrile (25 g, 0.144 mol), DMSO (200 ml), and sodium 3-mercaptopropanesulfonate (32 g, 0.18 mol), was added sodium carbonate (16.5 g, 0.156 mol), and the resultant mixture was heated to 60° C. followed by stirring for 3 hours. The reaction mixture was poured into a 10% brine (300 g), and the thus-precipitated solids were collected through filtration and washed with a mixed liquid of isopropanol/water (3/1). To the thus-obtained solids, were added water (200 ml), acetic acid (3 ml), and $Na_2WO_4$ (2 g), and then a 31% hydrogen peroxide aqueous solution (50 ml) was added thereto. The resultant mixture was heated to 60° C. followed by stirring. Thus, the reaction mixture was stirred for 4 hours, and then poured into isopropanol (500 ml). The thus-precipitated solids were collected through filtration, and washed with a mixed liquid of isopropanol/water (3/1). The thus-obtained solids were dried, to thereby obtain Phthalonitrile compound 105 (24 g, yield 49% from 3-nitrophthalonitrile).

Synthesis of Phthalocyanine Compound 211

Phthalonitrile compound 105 (10.7 g, 29.4 mmol, water content 6%), diethylene glycol (40 ml), triethyl orthoacetate (14.2 g, 87.6 mmol), and acetic acid (0.21 g, 3.5 mmol) were mixed, and the mixture was heated to 100° C. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 211 (9.4 g, yield 90%). FIG. 1 shows an IR spectrum of the thus-obtained phthalocyanine compound.

Example 12

Phthalocyanine compound 211 was obtained (8.3 g, yield 80%) in the same manner as in Example 11, except that tetramethylammonium benzoate (11.6 g, 59.5 mmol) was used instead of the ammonium benzoate.

Example 13

Phthalocyanine compound 211 was obtained (6.2 g, yield 60%) in the same manner as in Example 11, except that ammonium carbonate (5.7 g, 59.5 mmol) was used instead of the ammonium benzoate.

Example 14

Phthalonitrile compound 105 (10.7 g, 29.4 mmol, water content 6%), diethylene glycol (40 ml), toluene (10 ml), and acetic acid (0.21 g, 3.5 mmol) were mixed, and the mixture was subjected to pressure reduction from atmospheric pressure to 95 kPa, and followed by heating at an outer temperature 110° C. The heating was continued until an inner temperature reached 100° C., to thereby distill off the toluene. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 211 (6.2 g, yield 60%).

Example 15

Phthalonitrile compound 105 (10.7 g, 29.4 mmol, water content 6%), diethylene glycol (40 ml), 1-propanol (10 ml), and acetic acid (0.21 g, 3.5 mmol) were mixed, and the mixture was subjected to pressure reduction from atmospheric pressure to 95 kPa, and heated to an outer temperature 110° C. The heating was continued until an inner temperature reached 100° C., to thereby distill off the 1-propanol. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 211 (6.6 g, yield 65%).

Comparative Example 11

Phthalocyanine compound 211 was obtained (2.9 g, yield 28%) in the same manner as in Example 11, except that sodium benzoate (8.36 g, 59.5 mmol) was used instead of the ammonium benzoate.

Comparative Example 12

Phthalocyanine compound 211 was obtained (0.5 g, yield 5%) in the same manner as in Example 11, except that DBU (9.06 g, 59.5 mmol) was used instead of the ammonium benzoate.

Comparative Example 13

Phthalocyanine compound 211 was obtained (1.0 g, yield 10%) in the same manner as in Example 11, except that no triethyl orthoacetate was added.

The comparison between Comparative examples 11 to 13 and Examples 11 to 15 revealed that the use of the ammonium salt, in addition to the dehydrating agent, remarkably improves the reaction yield.

Example 16

Synthesis of Phthalocyanine Compound 277

Phthalocyanine compound 277 was synthesized according to the following scheme.

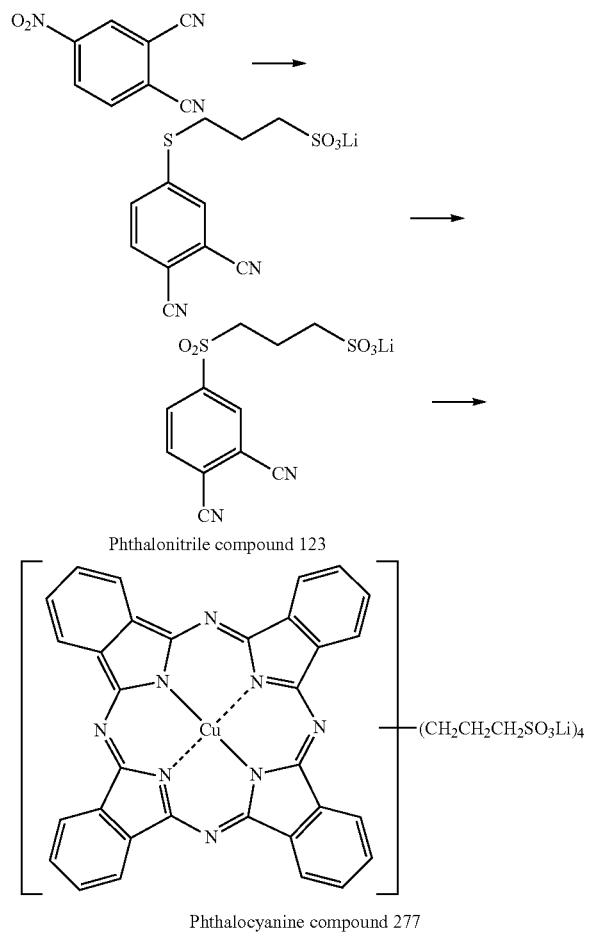

Phthalonitrile compound 123 was synthesized in the same manner as in Example 11, except that 4-nitrophthalonitrile was used instead of the 3-nitrophthalonitrile used in Example 11, and that operation of salt-exchange from a sodium salt into a lithium salt was further conducted.

Figure 2:
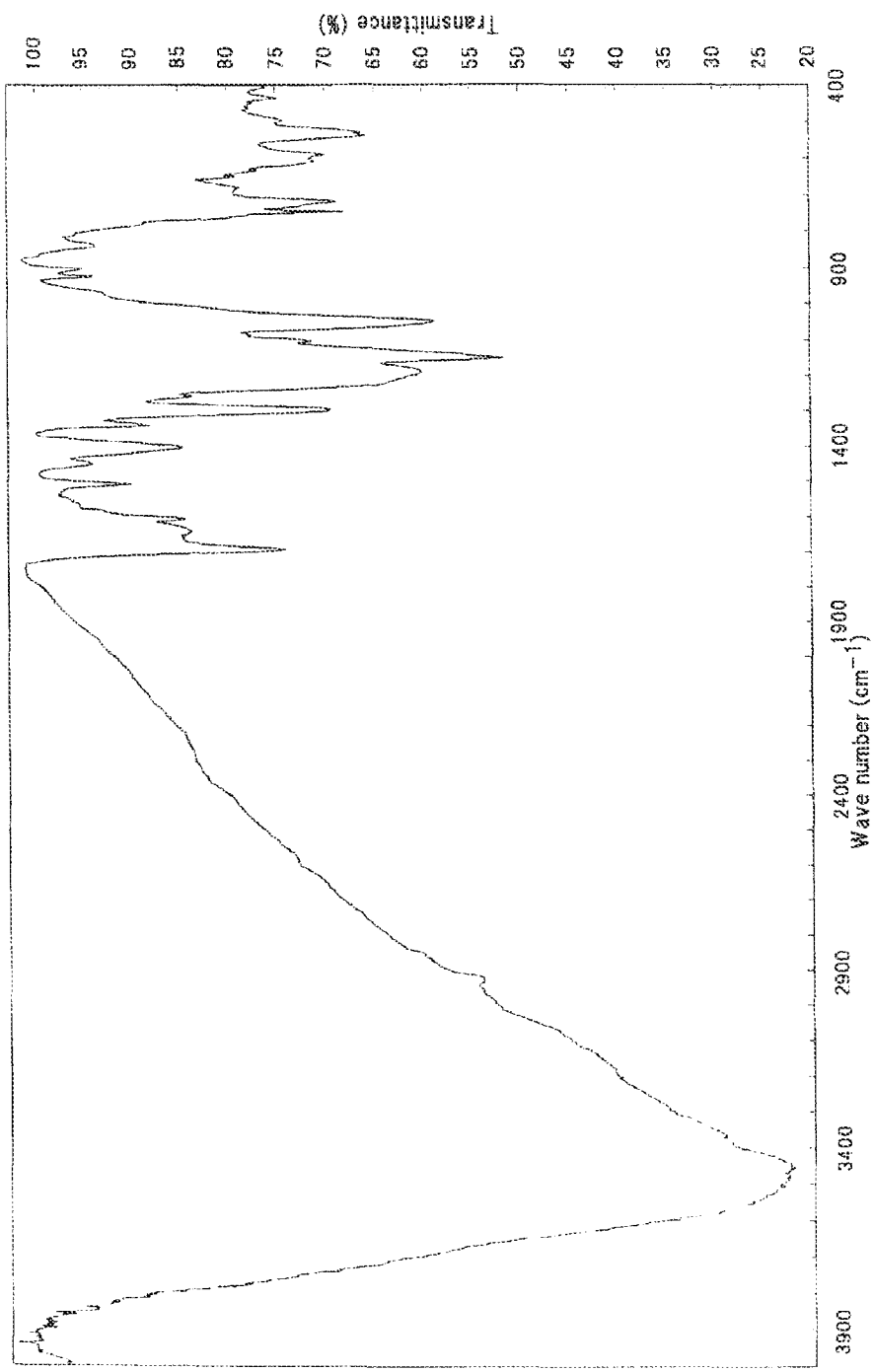
FIG. 2 is an IR spectrum of the phthalocyanine compound 277 obtained in Example 16.

Phthalonitrile compound 123 (9.9 g, 29.4 mmol, water content 5%), diethylene glycol (40 ml), triethyl orthoacetate (14.2 g, 87.6 mmol), and acetic acid (0.21 g, 3.5 mmol) were mixed, and the mixture was heated to 100° C. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 277 (9.9 g, yield 100%). FIG. 2 shows an IR spectrum of the thus-obtained phthalocyanine compound.

Example 17

Phthalonitrile compound 123 (9.9 g, 29.4 mmol, water content 5%), diethylene glycol (40 ml), toluene (10 ml), and acetic acid (0.21 g, 3.5 mmol) were mixed, and the mixture was subjected to pressure reduction from atmospheric pressure to 95 kPa, and followed by heating to an outer temperature 110° C. The heating was continued until an inner temperature reached 100° C., to thereby distill off the toluene. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 277 (8.9 g, yield 90%).

Example 18

Phthalonitrile compound 123 (9.9 g, 29.4 mmol, water content 5%), diethylene glycol (40 ml), 1-propanol (10 ml), and acetic acid (0.21 g, 3.5 mmol) were mixed, and the mixture was heated under an atmospheric pressure to an outer temperature 110° C. The heating was continued until an inner temperature reached 100° C., to thereby distill off the 1-propanol. $CuCl_2$ (1 g, 7.43 mmol) and ammonium benzoate (8.27 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 277 (9.1 g, yield 92%).

Comparative Example 14

Phthalonitrile compound 123 (9.9 g, 29.4 mmol, water content 5%), diethylene glycol (40 ml), triethyl orthoacetate (14.2 g, 87.6 mmol), and acetic acid (0.21 g, 3.5 mmol) were mixed, and the mixture was heated to 100° C. $CuCl_2$ (1 g, 7.43 mmol) and lithium benzoate (7.6 g, 59.5 mmol) were added to the reaction mixture, and the whole was stirred at 100° C. for 10 hours. The reaction mixture was added to isopropanol (100 ml), and the thus-precipitated crude crystals were collected through filtration. The thus-obtained crude crystals were washed with isopropanol/water (3/1), to thereby obtain Phthalocyanine compound 277 (7.9 g, yield 80%).

Comparative Example 15

Phthalocyanine compound 277 (7.7 g, yield 78%) was obtained in the same manner as in Example 16, except that no triethyl orthoacetate was added.

The comparison between Comparative examples 14 and 15 and Examples 16 to 18 revealed that use of the ammonium carbonate salt, in addition to the dehydrating agent, remarkably improves the reaction yield.

Example 19

Synthesis of Phthalocyanine Compound 340

Phthalocyanine compound 340 was synthesized according to the following scheme.

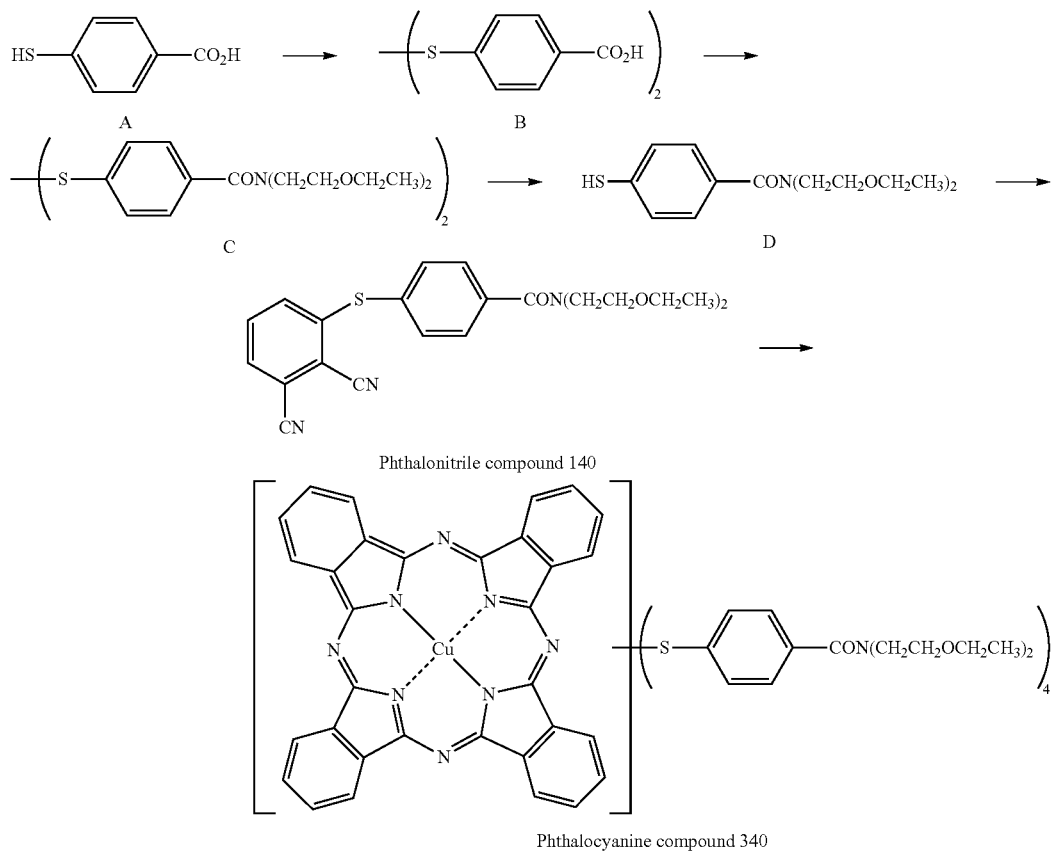

Phthalonitrile compound 140

Phthalocyanine compound 340

Synthesis of B

Compound A (25.0 g, 0.162 mol) was dissolved in methanol (100 ml) and triethylamine (23 ml). Then, to the resultant mixture, a 30% hydrogen peroxide aqueous solution (9 ml) was added dropwise, over 10 minutes, under cooling to 5° C. to 25° C. under stirring. The reaction liquid was stirred at 25° C. for additional 30 minutes, and concentrated hydrochloric acid (15 ml) was added dropwise into the reaction liquid cooled to 5° C. to 25° C. under stirring. Then, water (200 ml) was added thereto, and the whole was stirred at 25° C. for 1 hour. The thus-precipitated crystals were filtered and sufficiently washed with water. The thus-obtained crystals were dried, to thereby obtain white crystals of B (24.7 g, yield 99.5%).

Synthesis of C, D, and Phthalonitrile Compound 140

Toluene (100 ml) and dimethylacetamide (0.25 mol) were added to Compound B (17.5 g, 0.114 mol), and then to the resultant mixture was added dropwise thionyl chloride (25 ml) under reflux over 10 minutes. The mixture was refluxed under heating for additional 1 hour, and then concentrated under reduced pressure, to thereby obtain a viscous liquid. Separately, dimethylacetamide (10 ml) and acetonitrile (100 ml) were added to diethoxyethylamine (38.0 g, 0.235 mol), and to the resultant mixture the aforesaid viscous liquid was added dropwise over 15 minutes under stirring at 10° C. to 15° C. The mixture was stirred for additional 30 minutes, and was poured into water (100 ml) and ethyl acetate (100 ml), to thereby separate the ethyl acetate layer. The ethyl acetate layer was washed twice with water (100 ml). The ethyl acetate layer was dried with magnesium sulfate, and ethyl acetate was distilled off under reduced pressure, to thereby obtain a pale yellow viscous liquid of C. To this pale yellow viscous liquid of C, were added water (50 ml), ethanol (200 ml), and zinc powder (12 g), and to the resultant mixture was added, dropwise, a solution containing sulfuric acid (10 ml) diluted with water (40 ml) under reflux by heating, over 20 minutes. The mixture was stirred under heating for additional 30 minutes, and then cooled, and an insoluble substance was separated through filtration. To the thus-obtained solution, were added a saturated brine (50 ml) and ethyl acetate (100 ml), to thereby separate the ethyl acetate layer. The ethyl acetate layer was washed twice with water (100 ml). The ethyl acetate layer was dried with magnesium sulfate, and then the ethyl acetate was distilled off under reduced pressure, to thereby obtain a pale yellow viscous liquid of D. Separately, 3-nitrophthalonitrile (19.7 g, 0.113 mol), dimethylacetamide (70 ml), and potassium carbonate (15 g, 0.108 mol) were stirred at 20° C. to 25° C. under a stream of nitrogen, and to the resultant mixture was added the aforesaid pale yellow viscous liquid of D over 10 minutes. The mixture was stirred for additional 30 minute, and was then poured into water (300 ml) under stirring. The thus-precipitated crystals were filtered, and sufficiently washed with water. The thus-obtained crystals were recrystallized from methanol (70 ml). The precipitated crystals were filtered, washed with cold methanol (30 ml), and dried, to thereby obtain white crystals of Phthalonitrile compound 140 (35.0 g, yield 72.6%).

Synthesis of Phthalocyanine Compound 340

To Phthalonitrile compound 140 (34.4 g, 0.081 mol), were added 2-methoxy-1-propanol (75 ml) and diethylene glycol (75 ml), and then 15 ml of the solvent was distilled off under a stream of nitrogen at an inner temperature 120° C. over 30 minutes. Then, to the resultant solution, were added ammonium benzoate (11.3 g, 0.081 mol) and copper chloride (2.7 g, 0.02 mol), followed by stirring under heating for 5 hours. The reaction liquid was poured into ethyl acetate (150 ml) and water (150 ml), to thereby separate the ethyl acetate layer. The ethyl acetate layer was washed twice with a brine (200 ml). The ethyl acetate layer was dried with magnesium sulfate, and ethyl acetate was distilled off under reduced pressure. The thus-obtained solid was purified on silica gel column chromatography, to thereby obtain a powder of Phthalocyanine compound 340 (34.2 g, yield 93%).

Physical property data: $\lambda$max 652 nm (ethyl acetate solution (containing 1% chloroform))

Comparative Example 16

2-Methoxy-1-propanol (75 ml) and diethylene glycol (75 ml) were added to Phthalonitrile compound 140 (34.4 g, 0.081 mol), and the mixture was heated to an inner temperature 120° C. under a stream of nitrogen. Then, to the resultant solution, were added ammonium benzoate (11.3 g, 0.081 mol) and copper chloride (2.7 g, 0.02 mol), and the mixture was stirred under heating for 5 hours. The reaction liquid was poured into ethyl acetate (150 ml) and water (150 ml), to thereby separate the ethyl acetate layer. The ethyl acetate layer was washed twice with a brine (200 ml). The ethyl acetate layer was dried with magnesium sulfate, and ethyl acetate was distilled off under reduced pressure. The thus-obtained solid was purified on silica gel column chromatography, to thereby obtain a powder of Phthalocyanine compound 340 (23.2 g, yield 63%).

The comparison between Example 19 and Comparative example 16 revealed that the dehydration operation upon distilling off the dehydrating agent improves the yield.

Example 20

Synthesis of Phthalocyanine Compound 296

Phthalonitrile compound 139 (30 g, 120 mmol), triethyl orthoacetate (1.2 ml, 6.5 mmol), acetic acid (0.6 ml, 10 mmol), ammonium benzoate (35.1 g, 252 mmol), and $CuCl_2$ (4.0 g, 30 mmol) were suspended in diethylene glycol (120 ml), and the whole was stirred under heating at 100° C. for 5 hours. The suspension was cooed to room temperature. Then, concentrated hydrochloric acid (35 ml), water (60 ml), and methanol (90 ml) were added thereto, and the whole was stirred for 1 hour. Thus, blue precipitates were collected through filtration, to thereby obtain Phthalocyanine compound 296 (22.72 g, yield 71%).

Physical property data: $\lambda$max 676 nm (chloroform solution)

Comparative Example 17

Phthalocyanine compound 296 (17.6 g, yield 55%) was obtained in the same manner as in Example 20, except that no triethyl orthoacetate was added.

Comparative Example 18

Phthalocyanine compound 296 was obtained (15.4 g, yield 48%) in the same manner as in Example 20, except that DBU (38.4 g, 59.5 mmol) was used instead of the ammonium benzoate.

The comparison between Comparative examples 17 and 18 and Example 20 revealed that the combination use of the dehydrating agent and the ammonium carbonate salt remarkably improves the yield.

Industrial Applicability

The method of the present invention allows production of a metal phthalocyanine compound in high yield, and high purity, with favorable operability, and industrial stability.

Further, the production method of the present invention allows synthesis of a variety of phthalocyanine compounds having various substituents efficiently in high yield.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A method of producing a metal phthalocyanine compound, comprising:
   conducting a reaction between at least two compounds (i) and (ii) selected from the group consisting of Compounds A to F represented by formula (I), and a metal compound, in a buffer solution of an organic base or an inorganic base and an acid, in the presence of a dehydrating agent:

Formula (I)

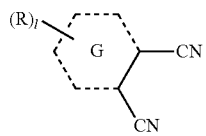

Compound A

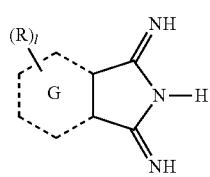

Compound B

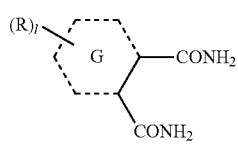

Compound C

Compound D

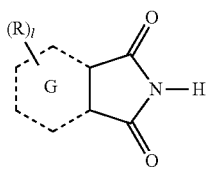

Compound E

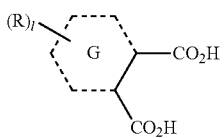

Compound F

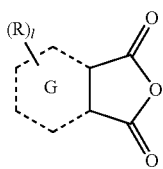

wherein R represents a hydrogen atom or a substituent; l represents an integer of 0 to 4; a plurality of Rs may be the same or different from each other when l is 2 to 4; and G represents a group of atoms necessary for forming at least one of a 6-membered aromatic ring and a 6-membered hetero ring;

wherein the compound (i) has the 6- membered aromatic ring as G, and compound (ii) has the 6-membered hetero ring as G.

2. The method of producing a metal phthalocyanine compound according to claim 1, wherein the Compounds A to F represented by formula (I) are Compounds G to L represented by formula (II):

Formula (II)

Compound G

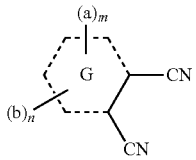

Compound H

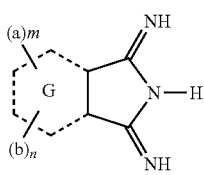

Compound I

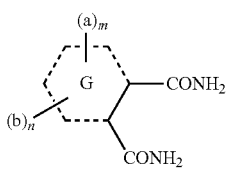

Compound J

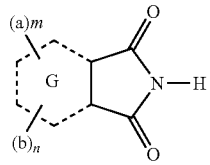

Compound K

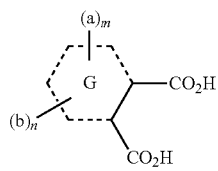

Compound L

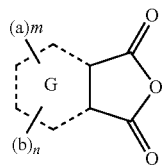

wherein a and b each independently represent a substituent; a total Hammett's constant σp value of the substituents is 0.20 or more; m and n each represent an integer satisfying $0 \leq m \leq 4$, $0 \leq n \leq 3$, and $0 \leq (m+n) \leq 4$; and G represents a group of atoms necessary for forming at least one of a 6-membered aromatic ring and a 6-membered hetero ring.

3. The method of producing a metal phthalocyanine compound according to claim 1, wherein the Compounds A to F represented by formula (I) are Compounds M to R represented by formula (III):

Formula (III)

Compound M

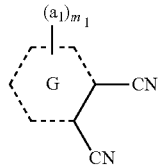

Compound O

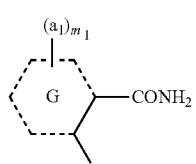

Compound Q

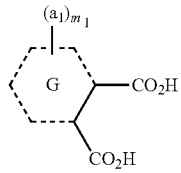

wherein $a_1$s each independently represent a sulfinyl group, a sulfonyl group, a sulfamoyl group, an acyl group, or a carbamoyl group, each of which may have a substituent; $m_1$ represents an integer of 0 to 2; and G represents a group of atoms necessary for forming at least one of a 6-membered aromatic ring and a 6-membered hetero ring.

4. The method of producing a metal phthalocyanine compound according to claim 1, wherein the Compounds A to F represented by formula (I), are Compounds S to X represented by formula (IV):

Formula (IV)

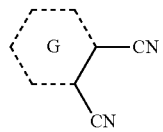

Compound W wherein G represents a group of atoms necessary for forming a 6-membered nitrogen-containing hetero ring;
wherein the compound (i) is selected from Compounds S to V, and the compound (ii) is selected from Compounds W and X.

5. The method of producing a metal phthalocyanine compound according to claim 1, wherein at least one selected from the group consisting of compounds represented by formula (V) and glycerin is used as a reaction solvent:

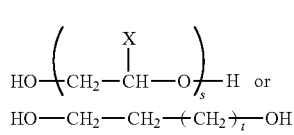

Formula (V)

wherein s and t each independently represent a positive integer; and X represents a hydrogen atom or a methyl group.

6. The method of producing a metal phthalocyanine compound according to claim 1, wherein the dehydrating agent is selected from the group consisting of an acetal compound, an orthoester compound, an alkenyl ether compound, an alkenyl ester compound, an epoxide compound, and an oxetane compound.

7. The method of producing a metal phthalocyanine compound according to claim 1, wherein at least one salt selected from the group consisting of an alkali metal salt, ammonium salt, or tertiary amine salt of a carboxylic acid is used as the base.

8. The method of producing a metal phthalocyanine compound according to claim 1, wherein at least one compound selected from among compounds represented by formula (VI) is used as the base:

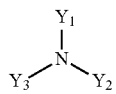

Formula (VI)

wherein $Y_1$, $Y_2$, and $Y_3$ each independently represent a hydrogen atom, an alkyl group, an alkenyl group, an alkynyl group, a cycloalkyl group, a cycloalkenyl group, an aryl group, or a hetero ring; $Y_1$, $Y_2$, and $Y_3$ may bond to form a condensed cyclic organic base; and $Y_1$, $Y_2$, and $Y_3$ may each further have a substituent.

9. The method of producing a metal phthalocyanine compound according to claim 1, wherein the hetero ring represented by G is a pyridine ring, a pyrazine ring, a pyrimidine ring, or a pyridazine ring.

10. The method of producing metal phthalocyanine compound according to claim 2, wherein the hetero ring represented by G is a pyridine ring, a pyrazine ring, a pyrimidine ring, or a pyridazine ring.

11. The method of producing a metal phthalocyanine compound according to claim 3, wherein the hetero ring represented by G is a pyridine ring, a pyrazine ring, a pyrimidine ring, or a pyridazine ring.

12. The method of producing metal phthalocyanine compound according to claim 4, wherein the hetero ring represented by G is a pyridine ring, a pyrazine ring, a pyrimidine ring, or a pyridazine ring.

\* \* \* \* \*